United States Patent [19]

Skolnick et al.

[11] Patent Number: 5,265,030
[45] Date of Patent: Nov. 23, 1993

[54] SYSTEM AND METHOD FOR DETERMINING THREE-DIMENSIONAL STRUCTURES OF PROTEINS

[75] Inventors: Jeffrey Skolnick, Encinitas; Andrzej Kolinski, San Diego, both of Calif.

[73] Assignee: Scripps Clinic and Research Foundation, La Jolla, Calif.

[21] Appl. No.: 932,282

[22] Filed: Aug. 19, 1992

Related U.S. Application Data

[63] Continuation of Ser. No. 803,678, Dec. 3, 1991, abandoned, which is a continuation of Ser. No. 513,918, Apr. 24, 1990, abandoned.

[51] Int. Cl.$^5$ .................. G06F 15/60; G06F 15/42
[52] U.S. Cl. ........................ 364/496; 364/578; 436/89
[58] Field of Search ............... 364/496-499, 364/578, 579; 395/119; 436/86, 89

[56] References Cited

U.S. PATENT DOCUMENTS

| | | | |
|---|---|---|---|
| 4,378,218 | 3/1983 | Fletterick . | |
| 4,704,692 | 11/1987 | Ladner | 364/498 |
| 4,853,871 | 8/1989 | Pantoliano et al. | 364/496 |
| 4,881,175 | 11/1989 | Ladner | 364/496 |
| 4,908,773 | 3/1990 | Pantoliano et al. | 364/496 |
| 4,939,666 | 7/1990 | Hardman | 364/496 |
| 4,982,338 | 1/1991 | Fujita | 364/496 |
| 4,985,827 | 1/1991 | Hamanaka et al. | 364/200 |
| 5,008,831 | 4/1991 | Feldman | 364/578 |

OTHER PUBLICATIONS

Bowie, et al., Deciphering the Message in Protein Sequences: Tolerance to Amino Acid Substitutions, Science 247: 1306 (1990).
Coghlan, et al., Determination of Proteinic Structures: An Experimentation Program, Comp. Phys. Comm. 36: 391 (1985).
Fraga, et al., Theoretical Studies of Protein Structures: Prediction of Antigenic Determinants, J. Mol. Struc. 120: 213 (1985).
Friedrichs, et al., Toward Protein Tertiary Structure Recognition by Means of Associative Memory Hamiltonians, Science 246: 371 (1989).
Hopp, et al., Prediction of Protein Antigenic Determinants from Amino Acid Sequences, PNAS USA 78: 3824 (1981).
Hopp, et al., A Computer Program for Predicting Protein Antigenic Determinants, Mol. Immunol. 20: 483 (1983).

(List continued on next page.)

Primary Examiner—Kevin J. Teska
Attorney, Agent, or Firm—Knobbe, Martens, Olson & Bear

[57] ABSTRACT

A computer system and method are disclosed for determining a protein's tertiary structure from a primary sequence of amino acid residues. The system uses a dynamic Monte Carlo method with Metropolis sampling criterion, and a selected (2,1,0) lattice model, to simulate protein folding during the transition of the protein from an unfolded (denatured) state to its native, folded state. The system generates, for display, a folding trajectory representing successive three-dimensional images of the protein at a level of two Angstrom resolution as it folds to its native conformation. The system permits interaction between all proximate pairs of sidechains of the protein and provides faster processing through the use of the lattice.

The system comprises an input means such as a keyboard for specifying (entering) selected amino acid sequences and other data such as temperature and fold preferences, a RAM (random access memory) for storing such data, a ROM (read-only memory) with a stored program, a CRT (cathode ray tube) display unit and/or printer, an optional auxiliary disc storage device for storage of relevant data bases, and a microprocessor for processing the entered data, for simulating, under control of the stored program, the folding of the protein from its unfolded state to its folded (tertiary) state, and for displaying via the display unit (or printer) tertiary conformations of the protein in three dimensions.

24 Claims, 15 Drawing Sheets

OTHER PUBLICATIONS

Keen, et al., Structural Modelling of Glasses Using Reverse Monte Carlo Simulation, Nature 344: 423 (1990).

Jonathan King, Deciphering the Rules of Protein Folding, C&EN, pp. 32–54 (Apr., 1989).

Kolinski, et al., Static and Dynamic Properties of a New Lattice Model of Polypeptide Chains, J. Chem. Phys. 94:3978–3985 (1991).

Padmanabhan, et al., Relative Helix-Forming Tendencies of Nonpolar Amino Acids, Nature 344: 268 (1990).

Roger Pain, Shuffling on this Mortal Coil, Nature 344: 198 (1990).

Skolnick, et al., Computer Simulations of Globular Protein Folding and Tertiary Structure, Ann. Rev. Phys. Chem. 40: 207 (1989).

Skolnick, et al., *Simulations of the Folding of a Globular Protein*, Science 250: 1121–1125 (1990).

William Taylor, Prediction of Protein Structure and the Principles of Protein Conformation, Fasman (ed.), Plenum, N.Y., 1989, pp. 285–322 (Chapter 12).

(SIDE VIEW)

(TOP VIEW)

T=591.800

T=591.950

T=592.000

T=592.100

T=592.150

T=592.250

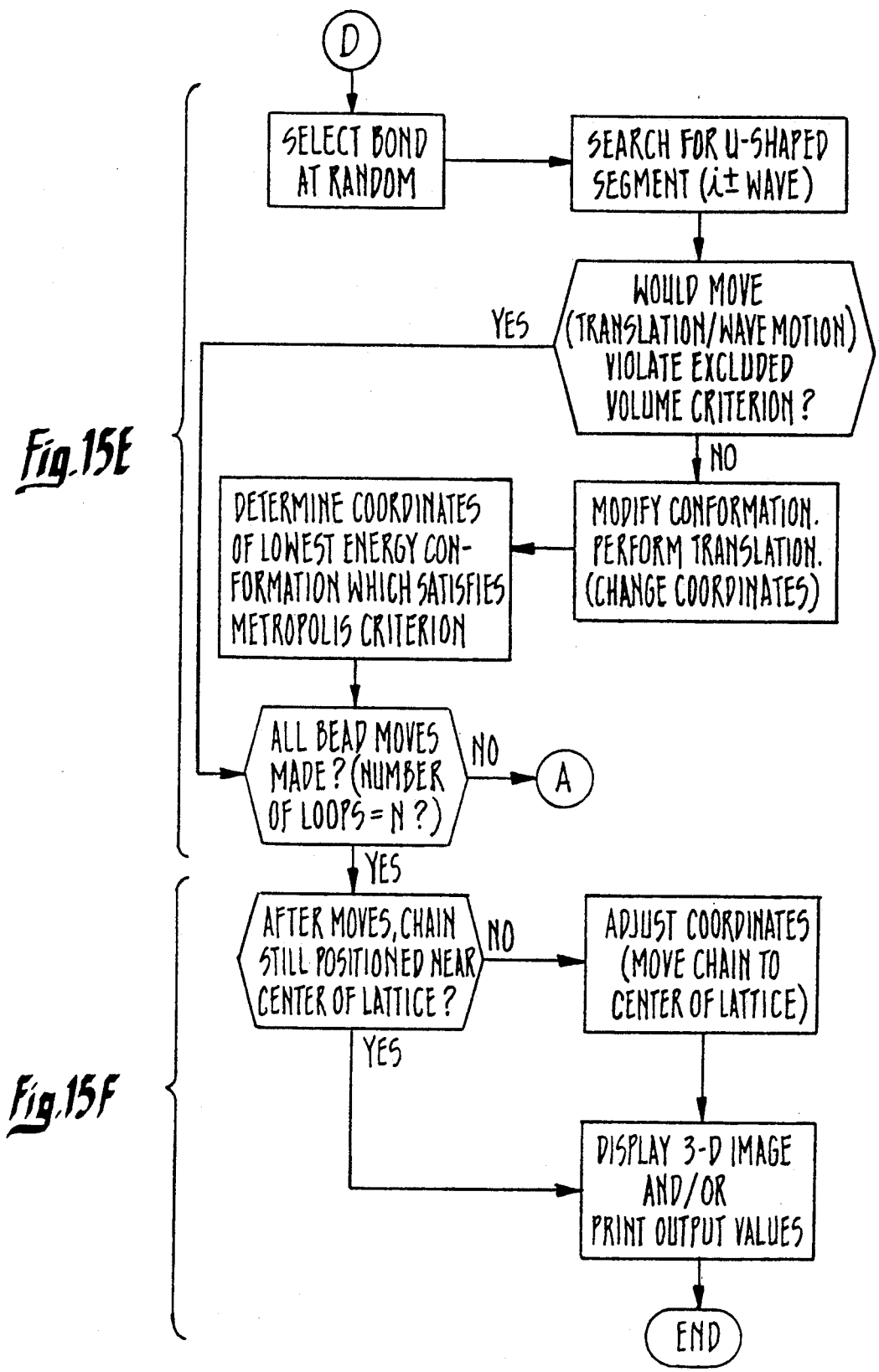

SYSTEM AND METHOD FOR DETERMINING THREE-DIMENSIONAL STRUCTURES OF PROTEINS

This invention was made with government support under National Institutes of Health Contract GM-37408. The government has certain rights in the invention.

This application is a continuation of application Ser. No. 07/803,678, filed Dec. 3, 1991, which is a continuation of U.S. Ser. No. 07/513,918, filed Apr. 24, 1990 both abandoned.

BACKGROUND OF THE INVENTION

This invention relates to modeling systems generally, and particularly to computer-based simulation systems used in determining three-dimensional structures (tertiary native conformations) of globular protein molecules.

The value of determining structure or conformation of proteins is well known. For example, in 1961 a Nobel Prize was awarded to Max Perutz for his work in determining the structure of the hemoglobin protein in blood. From this discovery, we now understand more about sickle cell hemoglobin and how drugs can be designed to treat patients with this disorder.

The prediction of antigenic determinants also is based on the prediction of protein tertiary structure. One such scientific work is reported, for example, by Hopp and Woods in "Prediction of protein antigenic determinants from amino acid sequences", Proceedings of the National Academy of Science USA 78, pp. 3824-3828 (1981), and in "A Computer Program for Predicting Protein Antigenic Determinants", *Molecular Immunology* Vol. 20, No. 4, pp. 483-489 (1983).

The structure (native conformation) of the protein, particularly the conformation of the outer sites or sidechains (which are linked to the backbone and inner structures of the protein) often determines the capacity of the protein to interact with other proteins. One factor which directly influences conformation is protein folding. Deciphering the rules through which the building blocks (amino acid sequences) of the protein affect folding promises significant improvements in the design of proteins, many with a host of new catalytic functions useful, for example, in the chemical, food processing, pharmaceutical, and other industries.

As a tool, computer systems are sometimes used to combine and display protein structures. One such system, used to convert two polypeptide chains to a single polypeptide chain, is described for example in U.S. Pat. No. 4,704,692, entitled "Computer Based System and Method for Determining and Displaying Possible Chemical Structures for Converting Double- or Multiple-Chain Polypeptides to Single-Chain Polypeptides", issued Nov. 3, 1987 to inventor Robert C. Ladner. Computer systems have also been used to investigate protein structures and predict protein folding. A few of such uses have been reported in Protein Folding by N. Go et al., pp. 167-81, ed. by N. Jaenicke, Amsterdam, Holland (1980); *Biopolymers* by S. Miyazawa et al., 21:1333-63, (1982); and *Journal of Molecular Biology*, by M. Levitt, 104:59-107 (1976).

These systems often (a) cannot process a full sequence of amino acid residues of a protein or protein segment (i.e., cannot process or otherwise represent the interactions of all the residues of the protein or protein segment; this task often becomes intractable, the system generally becomes unduly burdened by the many degrees of freedom of the residues), (b) cannot complete the folding process (because of inability of the system to recognize false, local energy—minima conditions), (c) cannot represent tertiary conformations in three dimensions, (d) cannot represent interactions between sidechains, (e) do not display the pathway taken by a protein in folding, or (f) do not permit free (unconstrained) interactions between residues for more realistic simulation of real proteins.

What is needed and would be useful, therefore, is a computer-based system that would eliminate the above-mentioned deficiencies, and provide a faster way of determining protein structures, thereby increasing the productivity of many scientists and encouraging the undertaking of many more needed investigations, including investigation of structures of protein sequences obtained from mapping of the human genome.

SUMMARY OF THE INVENTION

Accordingly, an improved computer-based system is provided that is capable of processing a full sequence of amino acid residues of a protein (e.g., plastocyanin), representing free (unconstrained) interactions between residues and between sidechains, tracking an entire folding operation (pathway) from the protein's unfolded (denatured) state to its fully folded (native) state, and displaying tertiary conformations of the protein in three dimensions.

The system comprises an input means such as a keyboard for specifying (entering) selected amino acid sequences and other data such as temperature and fold preferences, a RAM (random access memory) for storing such data, a ROM (read-only memory) with a stored program, a CRT (cathode ray tube) display unit and/or printer, an optional auxiliary disc storage device for storage of relevant data bases, and a microprocessor for processing the entered data, for simulating, under control of the stored program, the folding of the protein from its unfolded state to its folded (tertiary) state, and for displaying via the display unit (or printer) tertiary conformations of the protein in three dimensions.

A novel lattice is employed for representing (framing) the various conformations of the protein as it folds from an unfolded sequence of amino acid residues to a tertiary structure. The model comprises a cubic arrangement of 24-nearest-neighbor lattice sites, with adjacent sites located a unit distance from each other, and adjacent $\alpha$-carbons located a distance of $\sqrt{5}$ units from each other. The $\alpha$-carbons represent a chain or backbone of the protein. Each $\alpha$-carbon is shown to occupy a central cubic lattice side plus six adjacent cubic lattice sites defining a surface of interaction (e.g., an area or volume having a surface of finite size). Each sidechain is represented as being embedded in the lattice and occupying a selected number (four) of lattice sites located relative to the central site, the number of sites occupied by the sidechain being proportional to the number of sites defining the surface of interaction.

In response to specification of temperature and the amino acid sequence of the protein, the system determines the tertiary conformation of the protein using Monte Carlo dynamics with an asymmetric Metropolis sampling criterion. The system, (a) generates a three-dimensional representation of an unfolded conformation consisting of an $\alpha$-carbon backbone and sidechains, (b) produces (in accordance with local conformational preferences of the residues, and the lowest total energy of interactions between close sidechain pairs which satisfies the criterion) successive likely conformations at the temperature, according to the total energy of each conformation, (c) selects from the successive likely conformations the lowest total-free-energy tertiary conformation which satisfies said criterion, and (d) determines the coordinates of the selected tertiary conformation for display. In producing successive likely conformations, the system modifies each conformation by moving randomly selected residues (beads) and inter-residue bond vectors to different selected lattice sites by performing various type moves (single-bead jump-type moves, two-bead end-flip moves, chain-rotation type moves, and translation wave-type moves).

By the method employed by this system, simulation of protein folding and prediction of tertiary structure are not only performed with greater success and accomplished faster than by many existing methods, but the simulation itself becomes more manageable (tractable).

BRIEF DESCRIPTION OF THE DRAWINGS

FIGS. 15A-15F are block diagrams (flow charts) showing a method employed by the system of FIG. 3 in simulating protein folding.

DETAILED DESCRIPTION OF THE INVENTION

Figure 1:
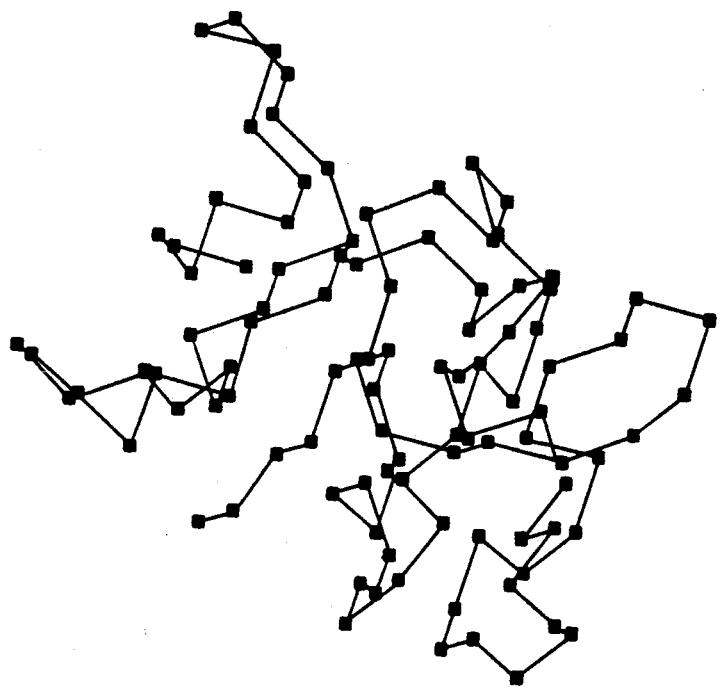
FIG. 1 is a diagramatic illustration of a globular protein in its native folded conformation.
Figure 2:
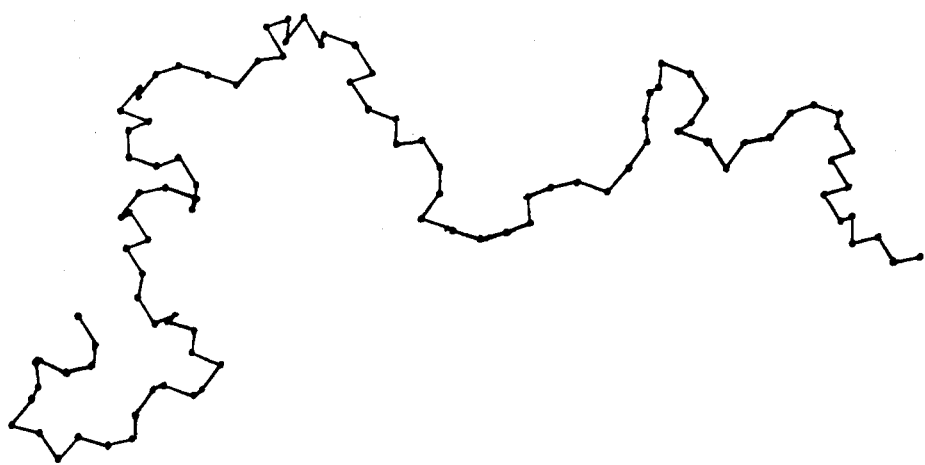
FIG. 2 is a diagramatic illustration of a full sequence of amino acid residues of which the protein represented in FIG. 1 is comprised.

A simplified representation of a globular protein (e.g., plastocyanin) in its native (natural, folded) form is shown in FIG. 1. A simplified representation of a full sequence of amino acid residues of which the protein is comprised is shown in FIG. 2. The protein becomes unfolded (denatured) when it is heated to an elevated temperature, and it refolds to its native form when the temperature is lowered to a selected level. Temperature may be specified in any unit (whether fahrenheit, centigrade, or Kelvin) and at any level or value (whether in or outside the transition range of the protein) as explained hereinafter. Generally, depending on the native biological conditions of the particular protein molecule being investigated, the temperatures that are specified are those in and bordering the transition region of the protein (typically, in and above 35° C.–45° C.).

Given a sequence of amino acid residues of a known or unknown protein, it would be useful, for example in the designing of a drug, to know to what protein form (structure, conformation) the sequence would fold if selected residues were changed (modified).

Figure 3:
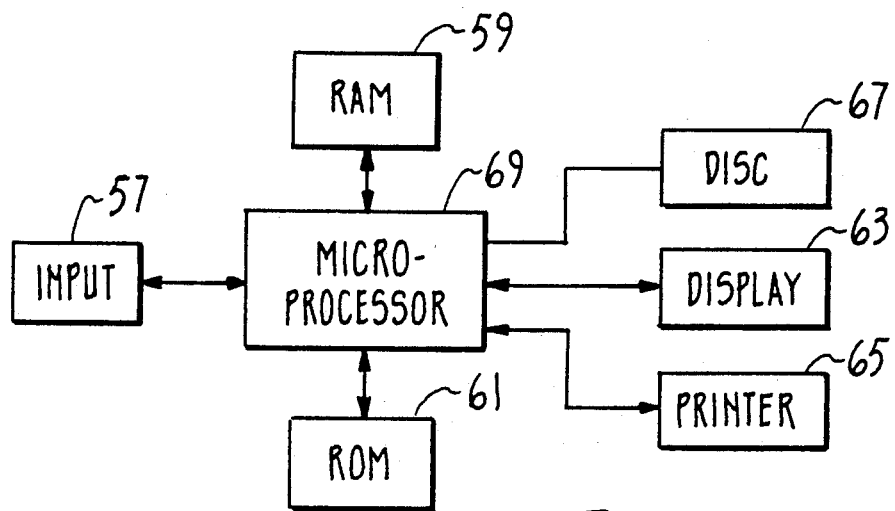
FIG. 3 is a block diagram of the system of the present invention.
Figure 4:
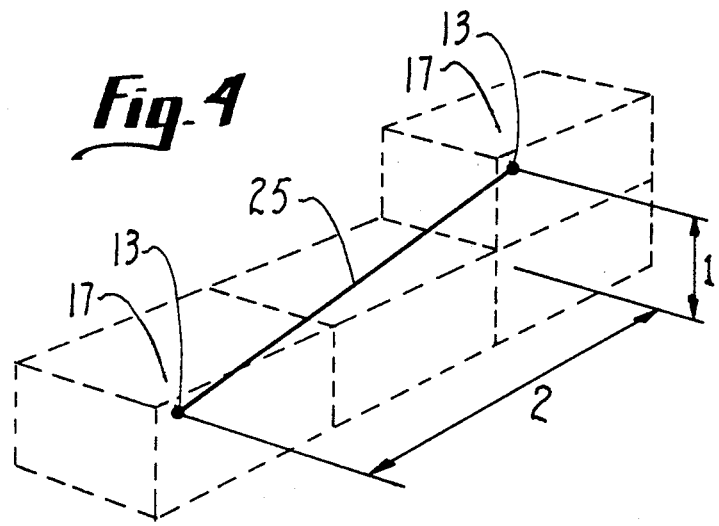
FIG. 4 is a block diagram showing a perspective view of a cubic lattice model employed in the system of FIG. 3.

To determine the probable tertiary structure (three-dimensional conformation) to which a given sequence or modified sequence would fold, a simulation of the folding operation could be performed on a computer system of the type shown in FIG. 3. The system uses a "210" lattice model, as shown in FIG. 4. The system is described in detail hereinafter. Prior to description of the system, however, to facilitate understanding of the invention, other aspects of the invention (such as lattice arrangement, types of movement of segments (residues) of protein within the lattice, orientational states of a segment, and inter-residue interaction) are described below.

Lattice Model, and Positioning of Protein Conformation

Figure 5:
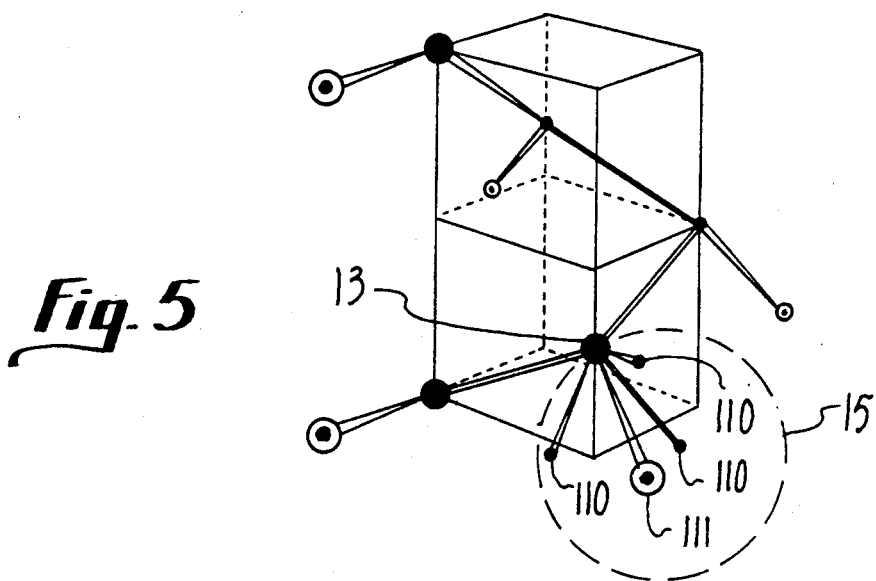
FIG. 5 is a block diagram showing a segment of a protein model comprising an α-carbon and sidechain in a cubic lattice of the type shown in FIG. 4.

Referring now to FIG. 5, a section or segment 11 of a full sequence (e.g., a sequence of a protein much like that depicted in FIG. 2) is shown in stick form (without associated residues or atomic structure). The section 11 includes an α-carbon segment 13 and a sidechain (β-carbon) segment 15 representative of each amino acid residue of the protein.

Figure 6:
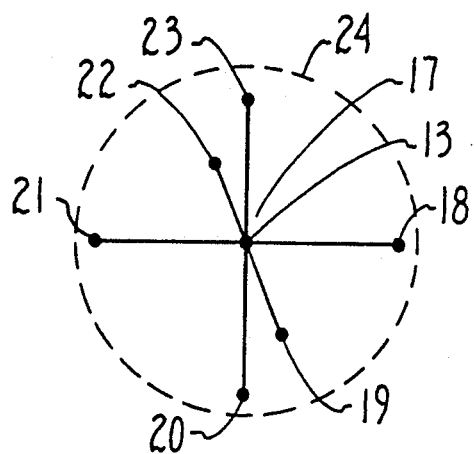
FIG. 6 is a diagramatic illustration of an α-carbon backbone of a protein segment.
Figure 7:
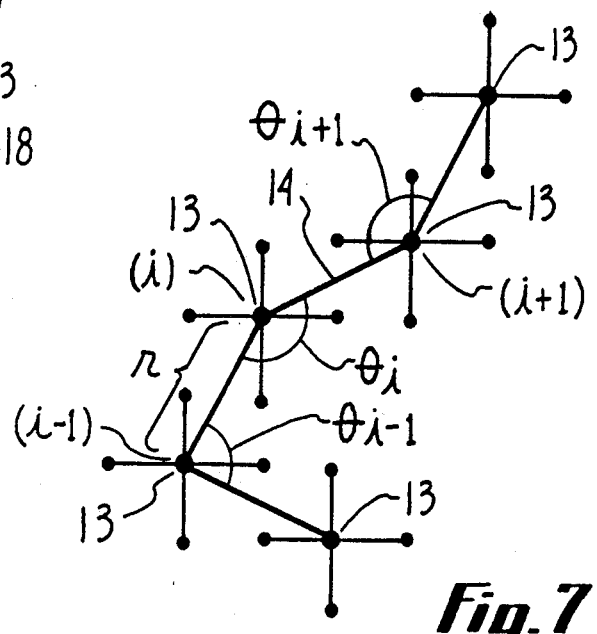
FIG. 7 is a diagramatic illustration of an α-carbon of the protein backbone segment shown in FIG. 6.

The protein segments may be viewed as embodied within a cubic reference framework or lattice model (FIG. 4), constructed from vectors of the type (1,0,0), (0,1,0), (0,0,1), the distance between any two adjacent points being unity. The α-carbon atoms 13 when linked as shown in FIG. 6 form the backbone 14 of the protein. As shown in FIGS. 4 and 7, each α-carbon 13 may be viewed as occupying a central cubic site 17 plus six adjacent cubic sites 18-23, defining a finite surface of interaction. Adjacent α-carbon centers may be viewed as linked by a 210-type lattice vector 25, as shown in FIG. 4.

The backbone 14 (FIG. 6) represents a structure of finite thickness about which a somewhat inflexible, hard core envelope of a chain of residues develop. The conformation of the backbone at the $i^{th}$ α-carbon is specified in terms of $r^2_{\Theta i}$, the square of the distance between adjacent α-carbons (i−1 and i+1) and $\Theta$ represents a bond angle that one of the α-carbons make with respect to the other, as shown in FIG. 6. In model units, the distance between consecutive α-carbons equals $\sqrt{5}$ units. Selected values of $r^2_\Theta$ are 6, 8, 10, 12, 14, 16, and 18, expressed in model units, indicating various accessible bond angle states. These values represent internal orientational states corresponding to actual (known) physical conformations.

Figure 8A:
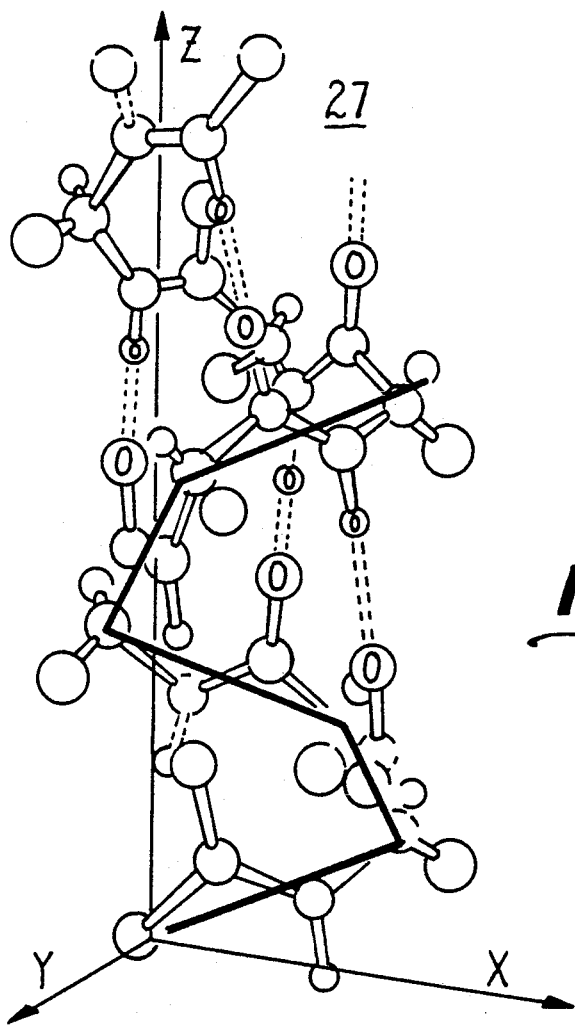
FIGS. 8A-8C are diagramatic illustrations of selected simple arrangements of an α-carbon backbone and associated sidechains.
Figure 8B:
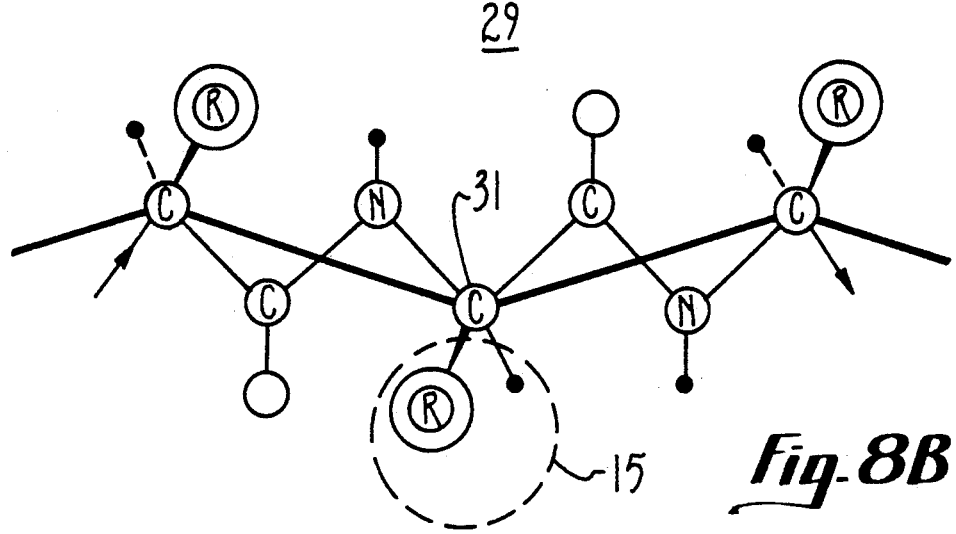
Figure 8C:
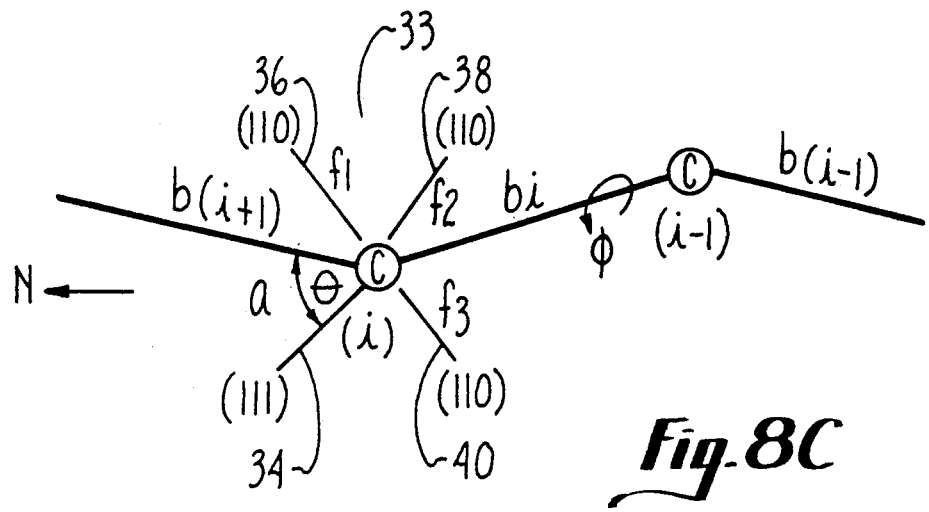

As shown in FIGS. 5 and 8, each $\alpha$-carbon has attached to it a sidechain 15, constructed for example in a helix conformation 27, or in a $\beta$-strand conformation 29. From the central vertex portion 31 of the $\alpha$-carbon, the sidechain 15 is formed, comprising four lattice vector points (1,1,0), (1,1,0), (1,1,0), and (1,1,1) 33. Three points represent fcc-type (face center cubic) lattice vectors, i.e., vectors of the type ($\pm 1$, $\pm 1$, 0). The fourth point represents a diamond lattice vector of the type ($\pm 1$, $\pm 1$, $\pm 1$). This latter vector serves as the center of hydrophobic or hydrophilic interactions (explained hereinafter). The orientation of the sidechain depends on the backbone conformation, i.e., depends on $r^2_\Theta$. At least two of the three fcc vectors comprising the sidechain are shown in an L-conformation (i.e., with left-handed chirality). The diamond lattice-type vector is always shown in the L-conformation. (For a more detailed description of lattice rules which should be followed when constructing conformations, refer to Appendix A.) For the calculations described hereinafter, either the residues are glycine, in which case there is no sidechain, or the residues have a sidechain of uniform size.

Interactions Between Residues

The following is a description of how the 210 lattice model (FIG. 4) is used to denote interactions between elements (residues) of a given backbone conformation, and to denote the energy of such interactions. To specify the conformation of the backbone of a chain, composed of n residues on an $\alpha$-carbon representation, n−2 bond angles ($\Theta$) and n−3 torsional angles ($\phi$) must be specified. To determine the conformation of the first and last residues, a virtual residue is appended to each end of the chain. These virtual residues are represented as inert. They occupy space but are devoid of sidechains. Thus, with the addition of the two fictitious (virtual) residues, n bond angles and n−1 torsional angles can now be used to specify the backbone conformation of the chain. (For convenience in denoting segments, the residues of the chain may be numbered from 1 to n.)

With respect to expressing (representing) a preference for a given conformation, any intrinsic preference of the protein model for a particular conformation may be represented by the individual preferences of the respective residues for the various bond angle states. In the description that follows, the term local conformational preferences shall mean the relative preferences which each local group of residues (i.e., a selected residue plus two flanking (adjacent) residues on either side of the selected residue) exhibit for the different conformational states. As indicated previously, these states are represented by the value $r^2_\Theta$ of the lattice model. Since for every residue i there are seven distinct values of $r^2_\Theta$, corresponding to 18 distinct local conformational states, the local energetic preference (denoted as parameter $\epsilon_\Theta(r^2_{\Theta i})$) for each of the states ($r^2_\Theta$ values) must be specified. If it is desired to reduce the number of such adjustable parameters (that is, parameters requiring specification), the conformations (except conformations where $\epsilon_\Theta(r^2_{\Theta i})=0$) may be made isoenergetic and assigned the value $\epsilon_\Theta > 0$.

In addition to bond angle, the torsional (dihedral angle) potential of a residue (i.e., its tendency to undergo an angle of rotation or twist) must be specified. The torsional potential associated with the $i^{th}$ residue is specified in terms of residues (i−1) through (i+2). Actually, a dihedral angle potential must be specified in the model for all residues from residue 2 (corresponding to real residue 1) to residue n−2 (corresponding to real residue n−1). Because the model is confined to a lattice, it is convenient to describe the torsional potential associated with the $i^{th}$ residue in terms of: (a) $r^2_\Theta$, $r^2_{\Theta i+1}$, the bond angle states i and i+1, (b) $r^2_\phi$, the square of the distance between $\alpha$-carbons i−1 and i+2, and (c) the handedness of the dihedral angle, $\chi = +1$ for right-handed chirality (R) or $\chi = -1$ for left-handed chirality (L). For example, a planar state having $\phi = 0$ is specified by (16, 16, 37, −1). That is, the square of the distance between $\alpha$-carbons i−1 and i+1 is 16, between $\alpha$-carbons i and i+2 is 16, and between $\alpha$-carbons i−1 and i+2 is 37. (For definiteness in the calculation, a dihedral angle of 0 is taken to be left-handed. This conformation could also be specified by the vectors $b_i$, $b_{i+1}$, $b_{i+2}$ as shown in FIG. 8). As many as 324 rotational states exist for each internal bond. These rotational states are all assigned a relative energy value $\epsilon_\phi$ ($r^2_{\Theta i}$, $r^2_{\Theta i+1}$, $r^2_{\phi i}\chi$). Generally, all such rotational states are statistically weighted. Where the majority of the conformations are taken to be isoenergetic (with a small bias toward a small subset of conformations that are native), the short and intermediate range energetic preferences may be represented as $\epsilon(r^2_{\Theta,i}, r^2_{\Theta i+1}, r^2_{\phi i})$.

The seven lattice sites that define the $\alpha$-carbon (FIG. 7) and the four lattice sites (FIG. 5) that define the surface 24 of the sidechain interact repulsively (i.e., with strong, hard core repulsion) with all the other $\alpha$-carbons and their respective sidechains. In other words, no more than one sidechain or $\alpha$-carbon can simultaneously occupy a given lattice site. (This is generally referred to as the excluded volume criterion.) Such a model may be viewed as having a backbone of finite thickness. In addition to the hard core repulsion, described above, there is a weak (soft core) repulsive interaction between non-bonded $\alpha$-carbon backbone centers located within a distance of $\sqrt{5}$ model units of each other. If $r_{kl}$ represents the distance between the $k^{th}$ and $l^{th}$ such centers, then the soft core repulsive energy $\epsilon_{rep}$ between the pair may be expressed as:

$$\epsilon_{rep} = \begin{bmatrix} \infty; & r^2_{kl} = 0, 1, 2, 4 \\ \epsilon_{rep}; & r^2_{kl} = 3 \\ 3\epsilon_{rep}; & r^2_{kl} = 5 \\ 0; & \text{otherwise} \end{bmatrix}$$

($\epsilon_{rep}$ typically takes on the value of 6 in the calculations that follow.)

Following description of the lattice, bond angle, bond angle states, and torsional angles, a description of tertiary interactions between the residues in a three-dimensional setting is presented next. To represent the effect of hydrogen bonding and dipolar-type interactions, a cooperative interaction energy parameter $E_c$ is introduced which allows for secondary structure stabilization when any part of the $\alpha$-carbon hard core envelope of the l$^{th}$ residue is at a distance of 3 units from the α-carbon center of the k$^{th}$ residue.

If a pseudodot product between two vectors is defined as:

$$dot(b_k, b_l) = \begin{bmatrix} 1; & \text{if } b_k = \pm b_l \\ 0; & \text{otherwise} \end{bmatrix}$$

then, the cooperative interaction energy $\epsilon_{ckl}$ may be given by:

$$\epsilon_{ckl} = \epsilon_c \begin{pmatrix} dot(b_k, b_l) + dot(b_{k+1}, b_l) + \\ dot(b_k, b_{l+1}) + dot(b_{k+1}, b_{l+1}) \end{pmatrix}$$

where, $\epsilon_c$ represents an energetic preference parameter which is applied, uniformly, to all residue pairs independent of their conformation.

Sidechain Interactions

In the preceding section, the subject of interactions relating to backbone conformation was discussed. In the following section, the subject of interactions between sidechains is discussed. Sidechain interactions are treated as being independent of backbone conformation. Interactions between any pair of side chains is allowed if the interacting sidechain sites lie at a distance of $\sqrt{2}$ from each other. Sidechains may be hydrophobic, hydrophilic or inert. Pairs of hydrophobic sidechains interact with an attractive potential of mean force; hydrophobic/hydrophilic pairs interact with a repulsive potential of mean force; and hydrophilic pairs interact weakly (i.e., weakly attractive or repulsive with no change in quality to behavior).

With respect to the calculation of sidechain-sidechain interaction energy, the following rules (scales) were employed in one calculation: glycines were assumed to lack sidechains and were assigned a hydrophobicity index $h(i)=0$. Hydrophobic residues were assigned a negative hydrophobicity index $h(i)<0$, and hydrophilic residues were assigned a positive hydrophobicity index $h(i)>0$. For all sidechains that were greater than two residues apart down the chain, the sidechain-sidechain interaction matrix $am(i,j)$, representing the interaction energy between the i$^{th}$ and the j$^{th}$ pair of sidechains, was given in the form:

$$am(i,j) = -h(i) \cdot h(j) \cdot \epsilon$$

where $\epsilon = \epsilon_{phobe\text{-}phobe} > 0$, if h(i) and h(j) were both negative (that is, if both were hydrophobic). $\epsilon = \epsilon_{phobe\text{-}phil} > 0$ if one residue is hydrophobic and the other hydrophilic, and $\epsilon = -\epsilon_{phil\text{-}phil}$, (with $\epsilon_{phil\text{-}phil} > 0$), if both h(i) and h(j) are positive, that is, if both sidechains are hydrophilic. The subscripts phobe-phobe mentioned above represent interaction between two hydrophobic residues, phobe-phil represents interaction between a hydrophobic residue and a hydrophilic residue, and phil-phil represents interaction between two hydrophilic residues. (As indicated above and in the program listing shown in Appendix D, tertiary interactions between any spatially close pair of sidechains are implemented using a modified Miyazawa-Jernigan (MJ) hydrophobicity scale. Based on the frequency of occurrence of contacts between sidechain pairs in protein crystal structures, the MJ scale is used to determine effective inter-residue contact energies.

As used below, short-range interactions shall mean interactions between adjacent residues in the chain and does not include effects of their neighbors (i.e., neighboring residues in the chain). Medium-range interactions shall mean interactions between first, second, and third nearest-neighbor residue groups in the chain. Long-range interactions shall mean interactions between residues (not α-carbons) which are positioned greater than three nearest neighbors apart down the chain but which are spatially close (i.e., within 3° A of each other).

Both native and non-native interactions are allowed between non-bonded pairs of residues that are specially close enough to interact. No criterion or constraint is imposed to drive the simulation towards any predetermined native conformation. Based on long or short interactions, a native conformation may comprise one of a number of isoenergetic states. It is the juxtaposition of short-medium-and-long-range interactions, together with other factors described herein that produce the final result, namely a stable, folded conformation.

As described hereinafter, all of the energetic parameters, $\epsilon_\Theta$, $\epsilon_\phi$, $\epsilon_{rep}$, $\epsilon_{phobe\text{-}phobe}$, $\epsilon_{phobe\text{-}phil}$, $\epsilon_{phil\text{-}phil}$ are uniformly scaled by a reduced temperature factor, T.

With respect to specifying other characteristics of the primary sequence of amino acid residues, the following conventions are used. In a simplified model, the term $B_i(k)$ is used to represent the i$^{th}$ stretch of k residues in the sequence. The k residues are represented as having identical $\epsilon_\Theta$ and $\epsilon_\phi$ values and a marginal (short and intermediate range) preference for β-state conformation. Consistent with β-sheet formation, $B_i(k)$ also represents an alternating odd/even pattern of hydrophilic and hydrophobic residues.

Where a sequence of k residues are locally indifferent to whether they are in an α-helix or in a β-sheet, the term $AB_i(k)$ may be used to denote the i$^{th}$-stretch in the amino acid sequence containing k residues in an alternating hydrophobic/hydrophilic pattern, such that $\epsilon_\Theta(12) = \epsilon_\Theta(16)$ for all k residues. Where a sequence of k residues has an alternating hydrophobic/hydrophilic pattern and locally prefers α-helical state conformation, such that $\epsilon_\Theta(12) = 0$ and $\epsilon_\Theta(16) > 0$, this is denoted by the shorthand notation $A_i(k)$.

Putative band regions are denoted by $b_i(j)$, and consist of j residues located at the interface between putative β-stretches i and i+1.

Chain Dynamics. Modification of Conformations

The dynamics of the chain are simulated by a (pseudo) random sequence of conformational rearrangements (moves) (i) through (iv) described below. In all such moves, the bead (amino acid residue) on which the move is performed is chosen at random.

Figure 9:
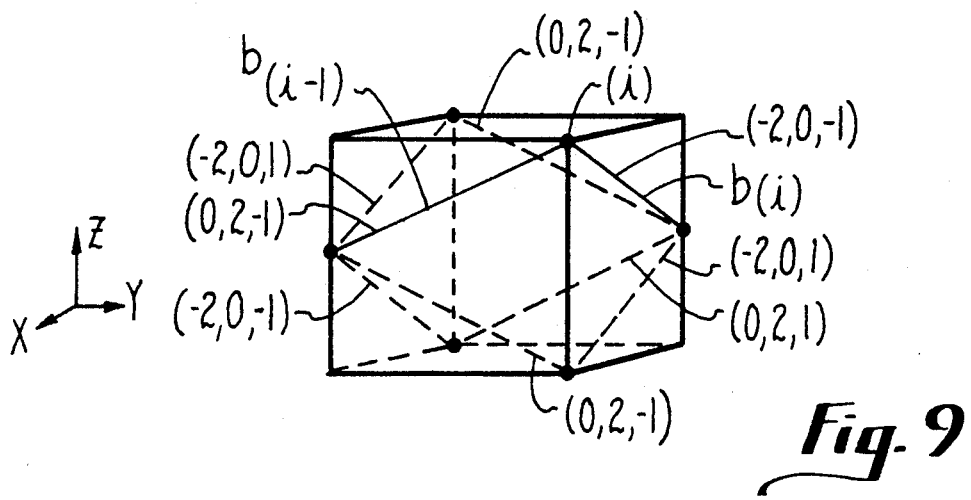
FIG. 9 is a diagramatic illustration of a jump-type move made by a randomly selected residue (bead) within the lattice of FIG. 4, effecting a change in conformation of the protein model.

(i) Examples of single bead jumps (also referred to as flips, spike or kink moves) are shown in FIG. 9. Also, a representative set of single-bead modifications is listed in Table I. These moves are constructed by conserving the vector $b_{i-1}+b_i$ (i.e., not changing the magnitude nor direction of imaginary vector $(b_{i-1}+b_i)$) The moves are made in a manner which maintains the bond angle associated with the i$^{th}$ residue but changes the bond angles of the i−1 and i+1 residues yielding five distinct possible outcomes (associated with $r^2_{\Theta i} = 12$), each of the moves is coded with five outcomes, some of which are degenerate (i.e., their conformations, each has the same energy). A clock is used to sequentially choose the particular outcome. New conformations of jumps (kinks) are also generated at random. After a move has been selected, it is only accepted if the adjacent bond angles are allowed (i.e., $r^2\theta_{i+1}$, and $r^2\theta_{-1}$ must lie in the range 6-18). If the move satisfies these local geometric constraints, then the sites (seven backbone sites plus four sidechain sites) into which the bead will jump are checked to insure that they are unoccupied. Otherwise, the move is rejected (not made).

A list of sample single-bead, modified vector values is presented in Table I.

TABLE 1

Sample Single Bead Modification Data

| CONFOR-MATION $r^2\theta$ | EXAMPLE SEQUENCE OF INITIAL VECTORS | POSSIBLE MODIFICATIONS |
|---|---|---|
| 2 (excluded) | — | — |
| 4 (excluded) | — | — |
| 6 | (2, −1, 0) (0, 2, 1) | a. (0, 2, 1), (210) |
| | | b. (2, 0, −1), (0, 1, 2) |
| | | c. (0, 1, 2), (2, 0, −1) |
| 8 | (1, 2, 0), (−1, 0, 2) | a. (−1, 0, 2), (1, 2, 0) |
| | | b. (1, 0, 2), (−1, 2, 0) |
| | | c. (−1, 2, 0), (1, 0, 2) |
| 10 | (1, 2, 0) (2, −1, 0) | a. (2, −1, 0), (1, 2, 0) |
| 12 | (1, 2, 0), (1, 0, 2) | a. (1, 0, 2), (1, 2, 0) |
| | | b. (2, 1, 0), (0, 1, 2) |
| | | c. (0, 1, 2), (2, 1, 0) |
| | | d. (2, 0, 1), (0, 2, 1) |
| | | e. (0, 2, 1), (2, 0, 1) |
| 14 | (2, −1, 0), (0, −2, 1) | a. (0, −2, 1), (2, 1, 0) |
| 16 | (1, 2, 0), (−1, 2, 0) | a. (−1, 2, 0), (1, 2, 0) |
| | | b. (0, 2, 1), (0, 2, −1) |
| | | c. (0, 2, −1), (0, 2, 1) |
| 18 | (−1, 2, 0 , (0, 2, 1) or | a. (0, 2, 1), (−1, 2, 0) |
| | (−2, 1, 0), (−1, 2, 0) | a. (−1, 2, 0), (−2, 1, 0) |
| 20 (excluded) | — | — |

(ii) With respect to two-bead end flips (in which the two end bonds are transformed to a new set of vectors), the set of two vectors is chosen at random from the twenty-four possible orientations of the lattice vectors. In this case, the two new end bond vectors must satisfy the allowed local bond angle criteria. If they do not, the move is rejected. Further, the two end residues in their new conformation must not violate excluded volume constraints.

The above-mentioned moves (i) and (ii) satisfy the correct dynamics for the athermal random coil state in the absence of hydrodynamic interactions.

Figures 10, 11:
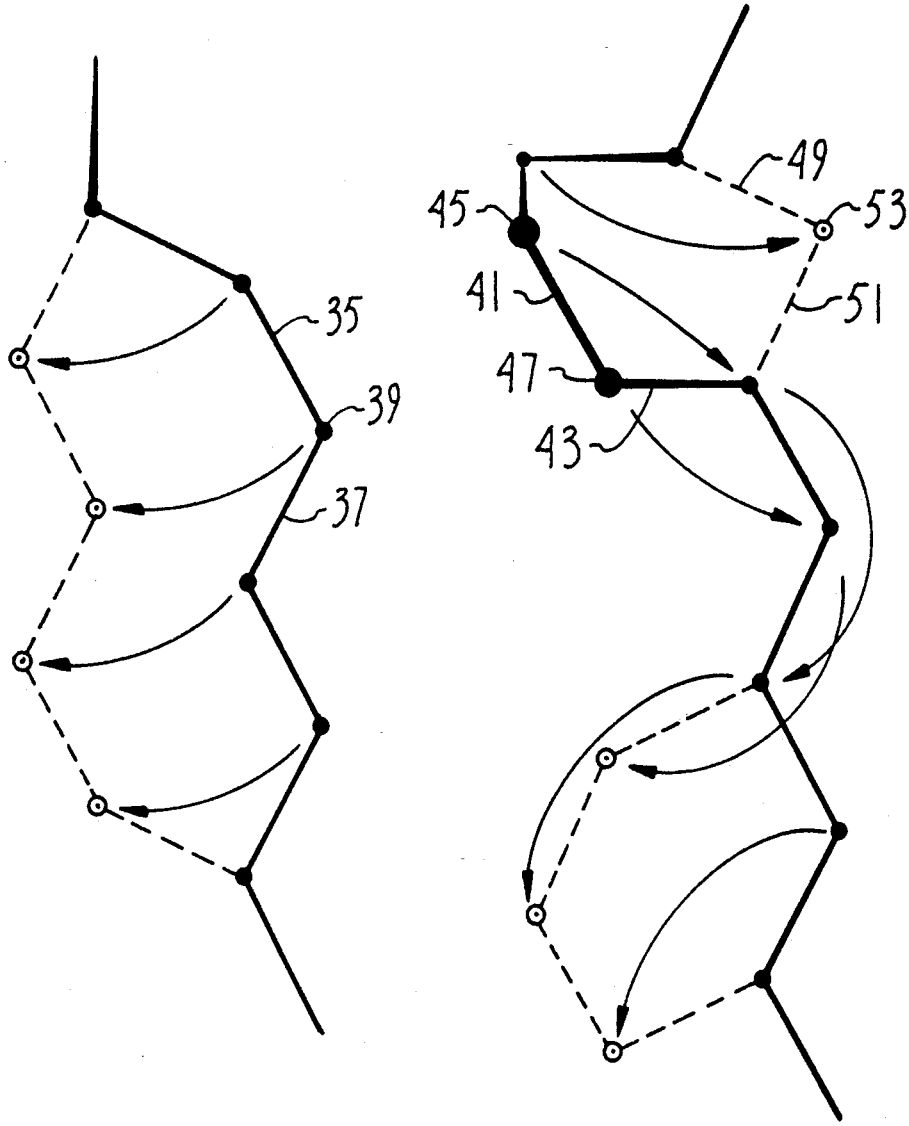
FIG. 10 is a diagramatic illustration of a rotation-type move made by a pair of randomly selected bond vectors within the lattice of FIG. 4, effecting a change in conformation of the protein model.
FIG. 11 is a diagramatic illustration of a translation-type (wave-type) move made by a U-shaped segment within the lattice of FIG. 4, effecting a change in conformation of the protein model.
Figure 12A:
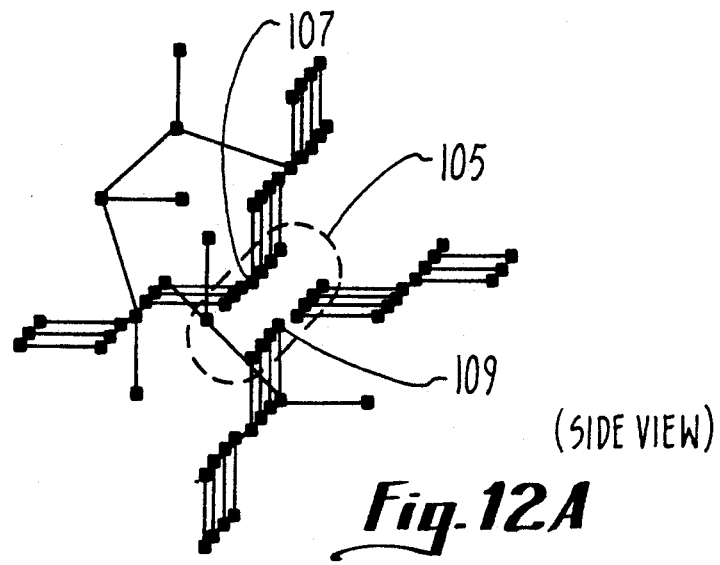
FIGS. 12A-12D are diagrammatic illustrations of the folding of a selected segment of a protein to a β-barrel conformation.
Figure 12B:
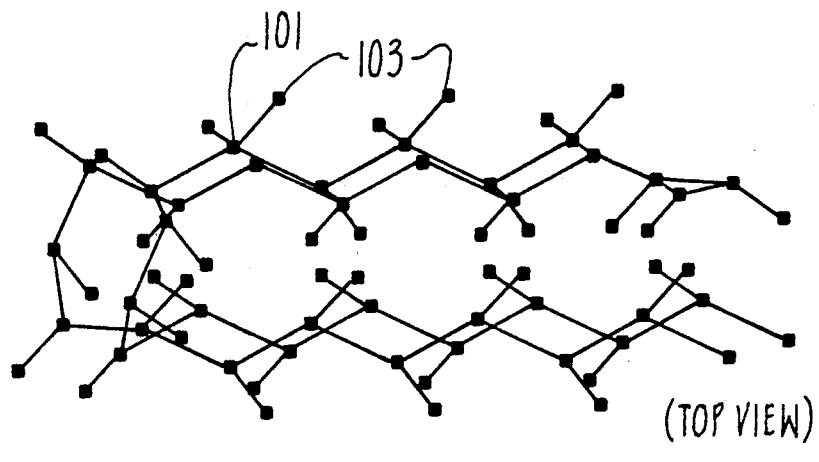
Figure 12C:
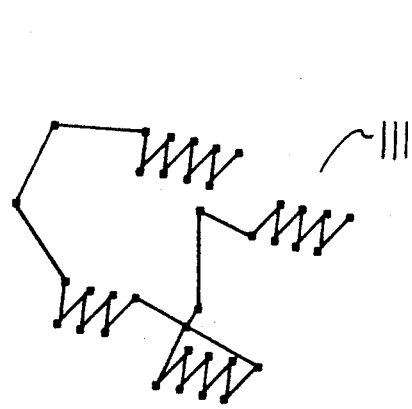
Figure 12D:
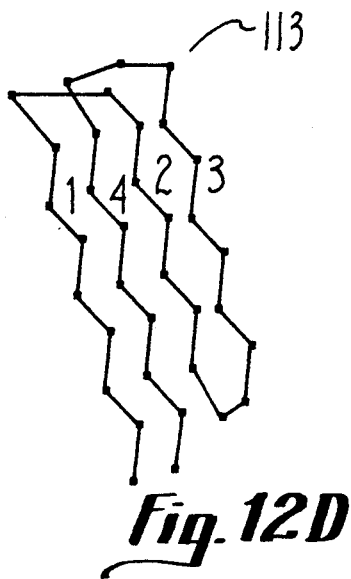

(iii) Turning now to chain rotations, an example of this type of move is shown in FIG. 10. The minimum size unit selected for rotation consists of three beads, and the maximum size unit is 2+wave. (The value of the parameter "wave" is generally 4, it is chosen so that the size of the unit undergoing the rotation is the size of a mean element of secondary structure.) The particular size of the unit ($\delta+1$) undergoing the attempted rotation is chosen by the value of an external clock parameter, and sequentially varies from the minimum to maximum size. A particular bead I, at one end of the rotating unit, is chosen at random. For beads less than n/2, the unit undergoing the rotation is $I-\delta$. For beads greater than n/2, the unit undergoing rotation is $I+\delta$. If ib represents the first residue at the beginning of the rotating unit, and iend represents the residue at the end of the rotating unit, then if the bond angle state between the vectors $b_{ib}$ and $b_{iend-1}$ is a 14-18 state, the rotation is attempted. (The range of values of $r^2\theta_i$ is chosen so that the rotation is physically possible.) The rotation is implemented by interchanging the two bond vectors (e.g., vectors 35, 37 joining randomly selected bead 39 shown in FIG. 10). The initial set of bond vectors joining residues ib to iend is ($b_{ib}$, $b_{ib+1}$, . . . . $b_{iend-2}$, $b_{iend-1}$). The final set of bond vectors is ($b_{iend-1}$, $b_{ib+1}$, . . . $b_{iend-2}$, $b_{ib}$). The new conformation is checked to insure that it can join the remainder of the chain without violating bond angle restrictions and excluded volume restrictions.

(iv) Internal wave-like motions such as are shown in FIG. 11 are also performed. These moves serve to propagate defects down the subchain by deleting a defect at one end of the subchain and creating the defect at the other end of the subchain. The defect propagation procedure is performed by the system as follows. I denotes a bead chosen at random. The system first determines if a U-shaped defect exists (i.e., does $b_I = -b_{I+3}$?). If not, attempt at wave-like motion is abandoned. If a defect exists, the system then picks a place where the defect should be inserted. The chosen point is at $JJ = I + 2 \pm (5+\delta)$, with $\delta$ varying between 0 and wave-1. About half of the time, the defect insertion point lies to the left of I, and the other half the time it lies to the right of it. As mentioned before, typically, the value 4 is selected for wave. As shown in FIG. 11, the bond vectors $b_I$ 41 and $b_{I+3}$ 43 are then sliced out of the chain, thereby deleting two beads 43 and 47, provided that $b_{I+1}$ 49 and $b_{I+2}$ 51, which will form the new bond angle state or vertex I+1 53, satisfy the local geometric constraints of the chain. Next, two bonds 49, 51 are inserted into the chain. If the original vectors associated with beads JJ−1 and JJ are $b_{JJ-1}$ and $b_{JJ}$, the new set of four vectors are (v, $b_{JJ-1}$, $b_{JJ}$, −v), where the vector v is chosen at random. Note that the intervening bond factors between I+4 and JJ−2 are left unchanged. A new conformation is then generated by renumbering the residues so that their identity is conserved. As before, both excluded volume and local bond angle criteria must be satisfied in order for the conformation to be accepted.

After each of the elemental moves (i)-(iv), described above, the energy of the new conformation, $E_{new}$, is calculated and compared to the energy of the old conformation $E_{old}$. $E_{new}$ represents the sum of the individual energies, and is expressed as:

$$E_{new} = E_\theta + E_\phi + E_c + E_s$$

where $$E_\theta = \sum_N \epsilon_\theta$$

$$E_{100} = \Sigma_{tor}$$

$$E = \sum_{i,j} \epsilon_{ckl}$$

and $E_s$ (also referred to as $E_{side}$) = $\frac{1}{2}_{i,j} \Sigma$ am(i,j)

(The term $E_{old}$ represents the initial total value, then successive previous total values with which $E_{new}$ is compared.)

With respect to free energy (as distinct from total energy), the system attempts to find a free energy minimum, given as:

*Free energy = Total energy − TS* where T represents temperature, and S represents entropy.

If $E_{new}$ is less than $E_{old}$, then the conformation is accepted. Otherwise, a Metropolis sampling criterion is applied (as described for example in *Monte Carlo Methods in Statistical Physics* 2nd ed. by K. Binder, Springer-Verlag, Berlin, New York, 1986). In which event, a random number R uniformly distributed between 0 and 1 is generated. If R is less than the probability P, where $$P = \mathrm{EXP}^{\frac{-(E_{new}-E_{old})}{K_BT}}$$

then the conformation is accepted; otherwise, it is rejected. Here, $k_B$ represents Boltzmann's constant and T represents the absolute temperature of the protein. Thus, a standard asymmetric Metropolis sampling scheme (criterion) is employed. As described below, the sampling scheme or criterion is applied in conjunction with a dynamic Monte Carlo technique (as described for example in *Monte Carlo Methods in Statistical Physics* by K. Binder, cited above).

A single Monte Carlo dynamics time step consists of N attempts at move type (i) (jump-type move) mentioned above, two attempts at move type (ii) where each of the chain ends are subjected to move type (ii), one attempt at move type (iii), and one attempt at move type (iv). In the simulation, the protein model is started out in a randomly generated high temperature (T) state. It is then cooled down, equilibrated, cooled further, until collapse to a folded conformation occurs. For each simulation run in the transition region between unfolded and folded states, at least $1.25 \times 10^6$ Monte Carlo time steps are sampled. The set of elemental moves employed in the simulation satisfies the well known stochastic kinetics master equation describing the dynamics of the system. (Refer, for example, to Appendix B.) In the limit (after a large number of steps), an equilibrium distribution of states is generated.

With respect to the thermodynamics of folding, a detailed explanation is presented below. By restricting the protein to the lattice, it may be treated as a rotational isometric state model of the protein. First, the transition from the denatured to the native state is treated in the context of a two-state model. The free energies of the denatured state $A_D$, and the native state $A_N$ are calculated as follows: $A_D$ is calculated by neglecting all tertiary interactions in the denatured state (although pentane-like effects are included). In the calculation of $A_D$, long range excluded volume effects are neglected. For the calculation of $A_N$, small local fluctuations about the native state are neglected, and $A_N$ is approximated by the energy of the native state $E_N$.

In the context of a two-state model for folding, the fraction of molecules in the native state, $f_N$, is given by $$f_N = \exp\{-(E_N - A_D)\}/[1 + \exp\{-(E_N - A_D)\}]. \quad (2)$$

where $A_D$ is given as:

$$A_D = K_B T \ln(Z_D) \quad (3)$$

(The term $Z_D$ may be expressed as $Z_D = J\pi^{N-1} V_{D,i} J$, as defined in Appendix C.)

In the context of the two-state model, the mean square radius of gyration $<S^2>$, defined as $$<S^2> = \frac{\sum_{i=1}^{N}(r_i - r_{cm})^2}{N} \quad (4)$$

with $|r_i - r_{cm}|$ representing the distance of the $i^{th}$ bead from the center mass $r_{cm}$, may be expressed as $$<S^2> = f_N <S_N^2> + (1-f_N)<S_D^2> \quad (5)$$

where $<S_N^2>$ and $<S_D^2>$ are the mean square radii of gyration in the native and denatured state, respectively.

The above explanation may be used to select appropriate temperature values for use in the simulation. Substantial computer time can be saved by avoiding high temperatures associated with the denatured state. Also, temperatures that are too low can drastically quench the system.

Conformational Transitions

As shown below, conformational transitions can be approximated by a two-state model, or can be determined directly from folding trajectories.

In the following paragraphs, the requirements for folding to a unique conformation (e.g., a four-member $\beta$-barrel state) are described. FIGS. 12A-D show a segment with backbone $\alpha$-carbons 101 and interacting sidechain sites 103. Also shown in the top view are hydrophobic core 105 with the interdigitating sidechains 107, 109. Also shown are the corresponding conformations 111, 113 with $\alpha$-carbons alone.

The first of the three native turns is shown to involve the eight through eleventh residues with backbone bond angle conformations 18, 8, 18, and 10, respectively. The central turn is shown to involve a crossover connection between the two anti-parallel $\beta$-strands, and involves the eighteenth through twentieth residues with backbone bond angle conformations 14, 10, and 18. The remaining outer turn is shown to involve residues the twenty-sixth through twenty-ninth residues in bond angle conformations 12, 14, 14 and 8. The remainder of the bond angle states are all 16-type states. Thus, a planar $\beta$-sheet is assumed. Within an anti-parallel $\beta$-hairpin, the $\alpha$-carbons are shifted with respect to each other by one lattice unit. This allows for the interdigitation of the side chains mentioned above. In the fully native conformation, there are twenty contacts between neighboring sidechains (i.e., twenty pairs of sidechain interacting sites that are a distance of $\sqrt{2}$ from each other).

In the conformation considered here, the pattern of hydrophobic and hydrophilic residues is the same. The model chain consists of N=37 residues. In each of the strands, all of the even (odd) residues are hydrophobic (hydrophilic). The first strand consists of the first through eighth residue. The ninth through eleventh turn residues are all hydrophilic. The second strand runs from the twelfth to the eighteenth residue, with all the even (odd) residues hydrophobic (hydrophilic). The nineteenth and twentieth turn residues are, respectively, hydrophilic and hydrophobic. The third strand runs from the twenty-first to the twenty-sixth residue. The twenty-seventh through twenty-ninth are turn residues, all of which are hydrophilic. The fourth strand runs from the thirtieth to the thirty-seventh residue. The first and last residues (one and thirty-seven) are virtual residues (i.e., they are devoid of sidechains, but they do occupy excluded volume). They may be regarded as capping the two ends, and are included so that the bond angle state for the real residues (the second and thirty-sixth residue) may be defined.

Turning now to the subject of equilibrium folding, the requirements for equilibrium folding of a region of the chain to its unique, native structure (e.g., the four-member β-barrel structure) is described. The interplay of an intrinsic native turn propensity and a short- and medium-range preference for β-sheet formation is described.

In one simulation operation, for the sequence $B_1(7)b_1(4)B_2(6)b_2(3)B_3(5)b_3(4)B_4(8)$ the parameter $\epsilon_\Theta(16)$ was found equal to zero for the $B_i$ state and $-0.25/T$ for all the other states. For the $B_i$ state the parameter $\epsilon_\phi(16,16,37) = 0.6/T$, and is zero for all other states. For the turns $b_i$: $\epsilon_\Theta = 0$ for the native conformation, and $\epsilon_\Theta = 0.25/T$ for all other conformations. Similarly, $\epsilon_\phi = 0.6(1.75)/T = -1.05/T$. $\epsilon_{phil-phil} = 0.25/T$, $\epsilon_{phil-phob} = 1/T$, and $\epsilon_{phob-phob} = -0.75/T$. The cooperativity parameter $\epsilon_c = -0.15/T$. In the native conformation, the total short range free energy $E_\Theta = 0$, the total torsional energy $E_{tor} = -25.8/T$, the total sidechain interaction free energy arising from hydrophobic interactions $E_{side} = -14.25/T$, and the cooperative interaction free energy $E_c = -11.25/T$. Thus, the total energy of the native state $E_N = -51.3/T$. A summary of the conformational properties of this sequence, as well as all the other types of primary sequences, is presented in Table II. The primary sequence is designated by a shorthand notation $\epsilon_\alpha > \epsilon_\beta, 1, 1.75$. This notation indicates that, based on bond angle preferences, β-conformations are locally preferred for the $B_i$ portions of the primary sequence, and that the torsional angle preference $\epsilon_\phi$ (for native-like conformations in the $B_i$ region) is locally favored by a ratio of 1:1.75 over that in the turn region.

TABLE II
Compilation of Selected Folding Results

| Sequence | No. of Folding Attempts | No. of Successful Folds | Intrinsic Turn Probability |
|---|---|---|---|
| $\epsilon_\alpha > \epsilon_\beta; 1; 1.75$ | 5 | 5 | 0.0046 |
| $\epsilon_\alpha > \epsilon_\beta; 1; 1.5$ | 6 | 4 | 0.0021 |
| $\epsilon_\alpha = \epsilon_\beta; 1; 1.5$ | 6 | 6 | 0.0025 |
| $\epsilon_\alpha = \epsilon_\beta; 0.5; 1.5$ | 7 | 5 | 0.0093 |
| $\epsilon_\alpha = \epsilon_\beta; 0; 1.5$ | 11 | 5 | 0.063 |
| $\epsilon_\alpha = \epsilon_\beta; 0; 1.75$ | 10 | 10 | 0.14 |
| $\epsilon_\alpha < \epsilon_\beta; 1.6; 0.05$ | 11 | 11 | 0.036 |
| $\epsilon_\alpha = \epsilon_\beta; 1; 0$ | 14 | 0 | $5 \times 10^{-5}$ |

In the absence of long-range interactions, there is a negligible intrinsic preference for the native conformation. To address this point, reference is made to equations 2-5. Using equations 2-5, the transition midpoint (including tertiary interactions) is predicted to be near $T = 0.576$. Employing equation (3), it is found that at this temperature $A_D = -88.44$, and that $E_N$ (without tertiary interactions) equals $-44.79$. The fraction of molecules in the native conformation which would be present if all tertiary interactions are turned off (that is, the equilibrium population based on short and medium range interactions embodied in $E_\Theta$ and $E_{tor}$ alone) is given by $$f^o_N = \exp(-E_{tor}) / \exp(-A_D) \quad (6)$$

Using equation 6, $f^o_N$ is found to have the value:

$$f^o_N = 1.11 \times 10^{-19}.$$

Thus, there appears to be a negligible preference for the native state in the absence of long range interactions, suggesting that finding of the native conformation is by no means guaranteed by the above choice of short and medium range interaction parameters. Rather, this chain will thrash about until it finds the native state.

Figure 13A:
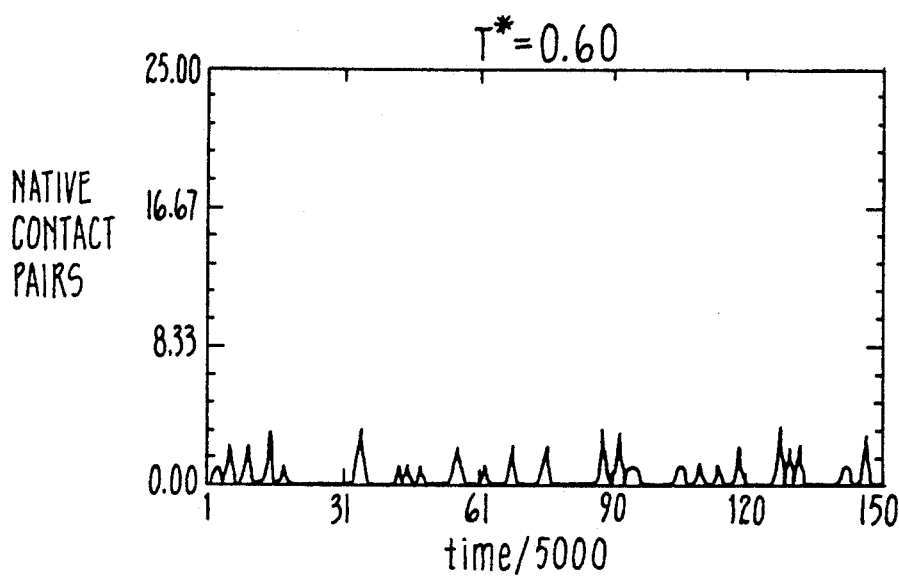
FIGS. 13A-13C are graphs showing an average number of native contact pairs between sidechains versus time.
Figure 13B:
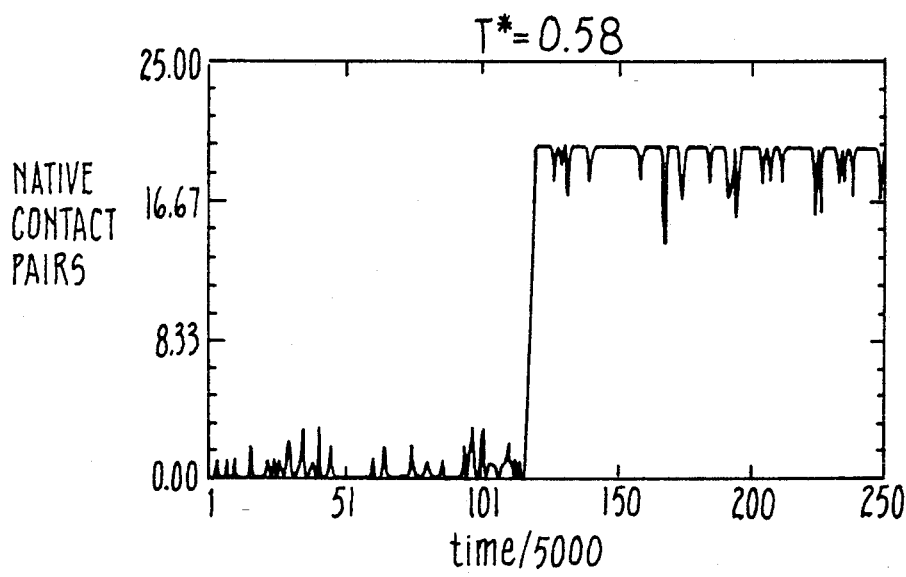
Figure 13C:
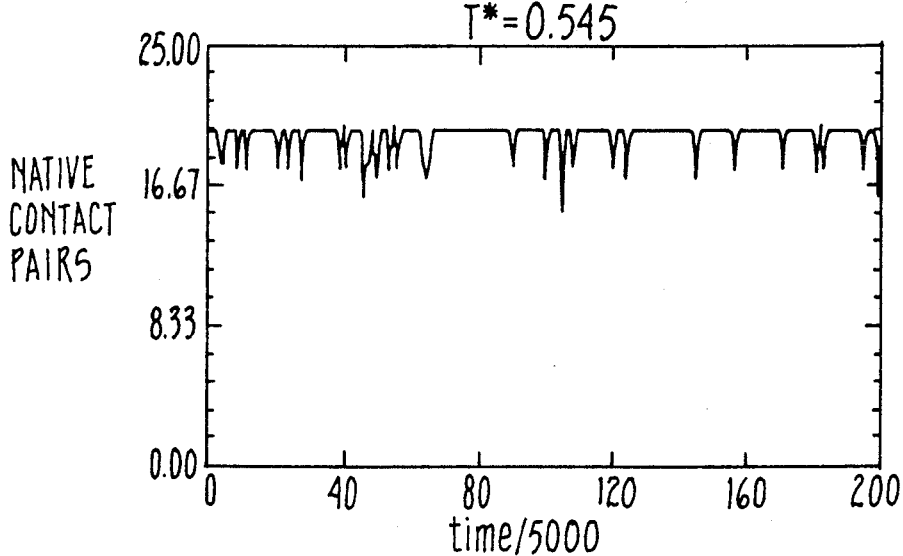

The next subject described below is the nature of the conformational transition itself. In FIGS. 13A–C, the average number of native contact pairs between sidechains ($N_c$) versus time, is plotted for a chain under denaturing conditions at $T = 0.6$, in the thermal transition region at $T = 0.58$, and under strongly renaturing conditions at $T = 0.545$. The times indicated in the Figure are in units of 500 Monte Carlo steps, and the fully native molecule contains twenty contact pairs. Under denaturing conditions, $N_c$ fluctuates around zero, characteristic of a relatively short, unfolded chain. In the transition region, the system starts out unfolded, and then around $t/5000 = 118$, it undergoes a rapid transition in about 6,500 Monte Carlo time steps to the fully native molecule. For the remainder of the time, it stays in the native state. Other conformational properties (not shown), such as the energy, the instantaneous value of the radius of gyration, the total number of contact pairs $N_{c,tot}$ also undergo sharp changes in value that is a characteristic of an all-or none transition (i.e., a transition where the intermediates between the denatured and fully folded states are marginally populated). On further cooling to $T = 0.545$, the chain becomes fully native, with minor oscillations in $N_c$ arising from the fluctuations of the ends residues of the chain.

Decreasing the turn propensity for native-like states decreases the stability of the native conformation and decreases the transition temperature. In the transition region, however, not only are native in-register four member β-barrels observed, but so are out-of-register conformations in which one of the exterior strands is two residues out-of-register, shifting the native contact between sidechains two and thirty-six to a non-native contact of residues two through thirty-four in one case, and to a non-native sidechain contact of residues four through thirty-six in the other case. In the former case, the outer turn began at residue twenty-five instead of residue twenty-six, thus, pushing the outer strand beyond the end of the barrel; and in the latter case, the turn began at residue twenty-eight and involved five residues, producing a bulge. Out of a total of six conformational transitions to a folded state, four folded directly to the native conformation, and two produced the out-of-register states described above.

The out-of-register state associated with residues four through thirty six occurred at relatively high temperature and folded in about 65,000 Monte Carlo steps. It remained folded for 315,000 time units before unfolding in about 165,000 time units.

Many out-of-register conformations have the same number of contacts between hydrophobic sidechains as in the native state; they differ in the cooperative free energy between the strands and in the local conformational preferences. Dropping the turn preference, increases the population of these out-of-register states. It is seen, therefore, that in the absence of some intrinsic preference for secondary structure, many in-register and out-of-register conformations can be generated, and it is the marginal intrinsic turn propensities which act to select from among them one conformation as the unique folded form. Based on tertiary interactions between hydrophobic sidechains alone, many otherwise degenerate conformations can be generated. Here, a marginal preference for $\beta$-strand secondary structure plus the presence of turn neutral regions are required for folding to occur to a unique native state. Here, turn propensities of 1% or lower (see below, and Table II) are sufficient to yield folding to the native barrel of FIG. 12.

It has been found that as the local propensity for $\beta$-states decreases, there is an increasing population of non-native turns and out-of-register states, even though the native turn population increases as T decreases. To fold the system to the global free energy minimum that corresponds to the native conformation, therefore, the free energy of out-of-register conformations should be increased relative to in-register conformations. As the local preference for $\beta$-states decreases, it becomes easier to form non-native turns; this appears to be the origin of the out-of-register states. Therefore, since the number of contacts between sidechains is approximately the same for the in-register and out-of-register cases, what determines the native conformation is the number of cooperative-type interactions, $\epsilon_c$, plus the differences in local conformational preferences. Where the local preference difference is decreased, a number of out-of-register states that are in deep local minima is observed.

For a primary sequence of the type $\epsilon_\alpha = \epsilon_\beta$; 0, 1.5 (which is similar to the above cases, except that the torsional potential in the putative $\beta$-strand is disregarded), the $\beta$- and $\alpha$-states are locally isoenergetic. The particular sequence of the $AB_i$ stretches are induced by tertiary interactions. In all cases, the folded conformations turn out to be $\beta$-barrels. Thus, tertiary interactions taken with local turn propensities provide for selection of $\beta$-collapsed states. Where the transition temperature is reduced, the native turn populations become greater. For example, the calculated turn population of native turn one is about 10% at T=0.40. Based on tertiary interactions alone, the unique native state is not achieved. This is most likely due to the degeneracy in sidechain contacts between the in-register and the two residue out-of-register conformers. If native turn propensity is sufficiently augmented, it appears that tertiary interactions plus intrinsic turn propensities are sufficient to yield the unique native state. Further, if the short-range interactions favoring $\beta$-strand formation are decreased, turn formation at a non-native location becomes more likely and, thus, the intrinsic turn propensity must be augmented (see Table II) to insure the recovery of a unique conformational state.

Next examined were sequences of the type $A_1(7)b_1(-4)A(6)b_2(3)A_3(5)b_3(4)A_4(8)$; that is, molecules having the sequence $\epsilon_\alpha < \epsilon_\beta$; 0, 1.6; 0.05, where the nature of the conformational transition for model proteins whose $\beta$-strands in the denatured state locally favor $\alpha$-helix conformation, but whose amino acid pattern still consists of alternating hydrophobic and hydrophilic residues. For $A_i$, it has been found that $\epsilon_\Theta(12)=0$, $\epsilon_\Theta(16)=0.05/T$, and for all the others $\epsilon_\Theta=0.25/T$. Furthermore, it was found that $\epsilon_\phi=0$ for all the residues in $A_i$. These systems (where the local preference is for an $\alpha$-helix conformation but the global free energy minimum conformation is that of a $\beta$-strand) spend substantial time trapped in relatively deep local minima. As the local preference for helical conformations is increased in the putative $\beta$-strand forming regions, while the unique four-member $\beta$-barrel is sometimes obtained, the chain generally thrashes about for over many millions of time steps (e.g., over 50 million) without finding a unique folded form.

An important indication from these simulation results is that a marginal local turn preference plus tertiary interactions are sufficient to produce unique native conformations, even in the extreme situation where the local conformational preference is for helices rather than $\beta$-sheet. If the native conformation is in thermodynamic equilibrium, then it is deemed to be at the lowest free energy state (conformation), independent of how the free energy is divided. That is, while it is conceptually convenient to divide the free energy into short-, medium- and long-range interaction contributions, it is the sum of these contributions, i.e., the total free energy, that determines the equilibrium conformation. The approach taken by the simulations show that the local minima problem can be surmounted to recover the lowest free energy structure, which overrides local considerations if there is a marginal turn propensity for native-like turns. Thus, turns appear to play an extremely important role in determining the ability to recover a unique native conformation.

Folding Pathway (Trajectory)

Figure 14A:
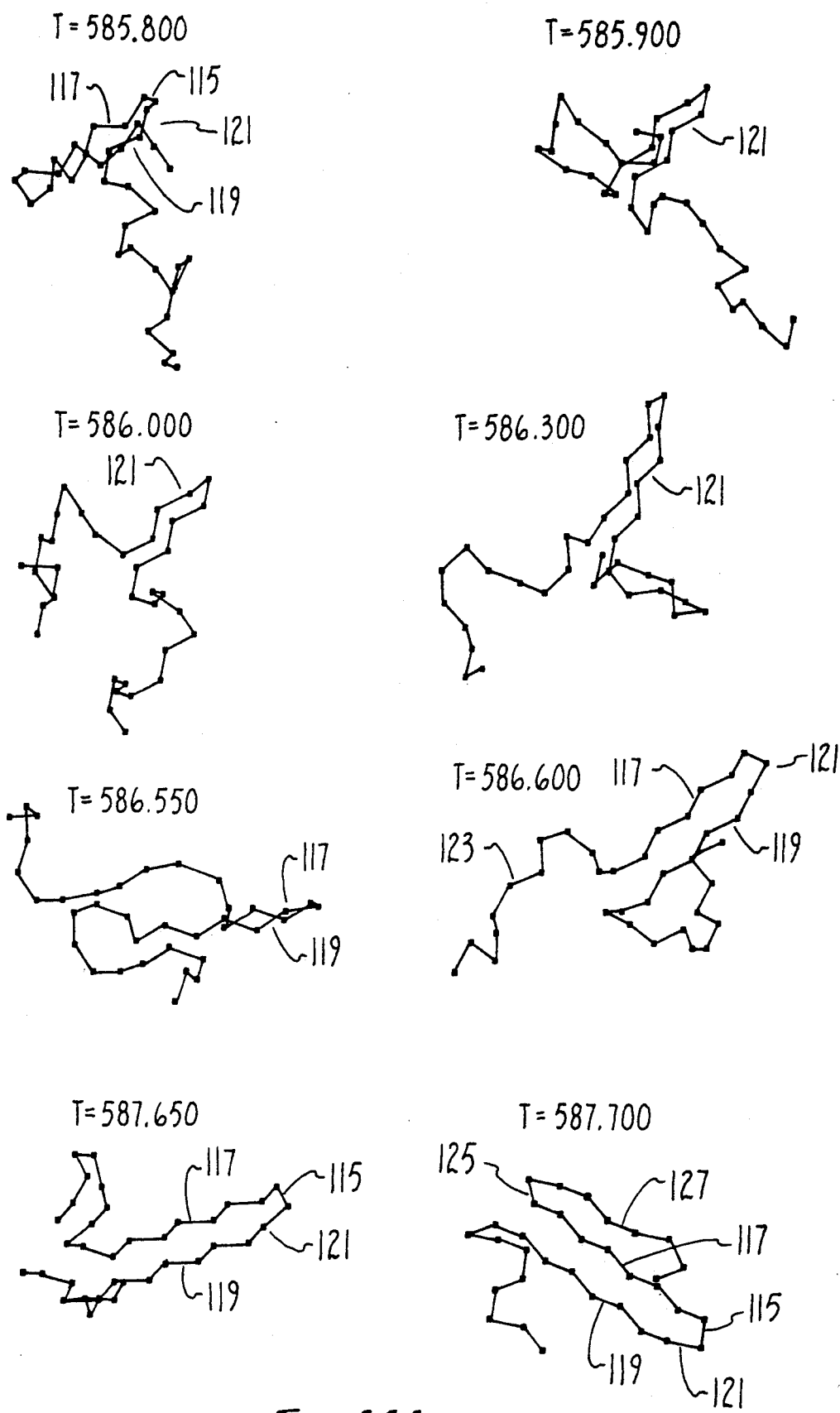
FIGS. 14A and 14B are graphical illustrations of a folding pathway defined by a sequence as it folds from an unfolded state to a folded (native) state.
Figure 14B:
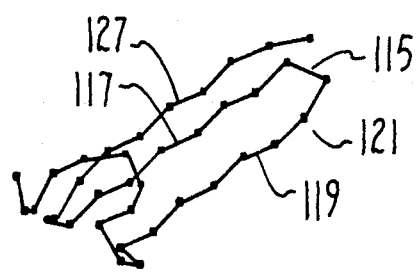
Figure 14B:
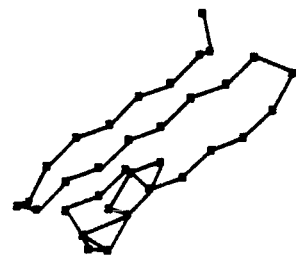
Figure 14B:
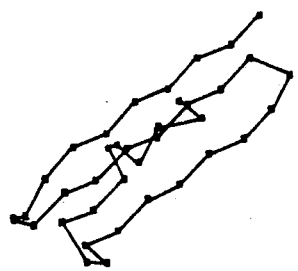
Figure 14B:
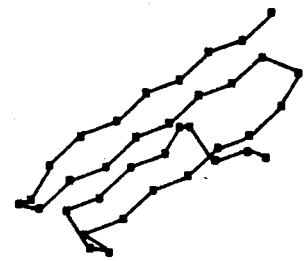
Figure 14B:
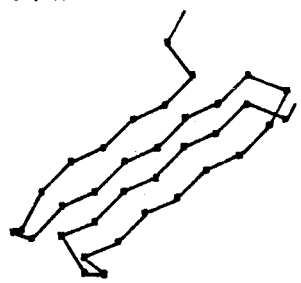
Figure 14B:
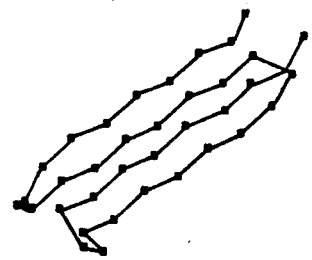
Figure 15A:
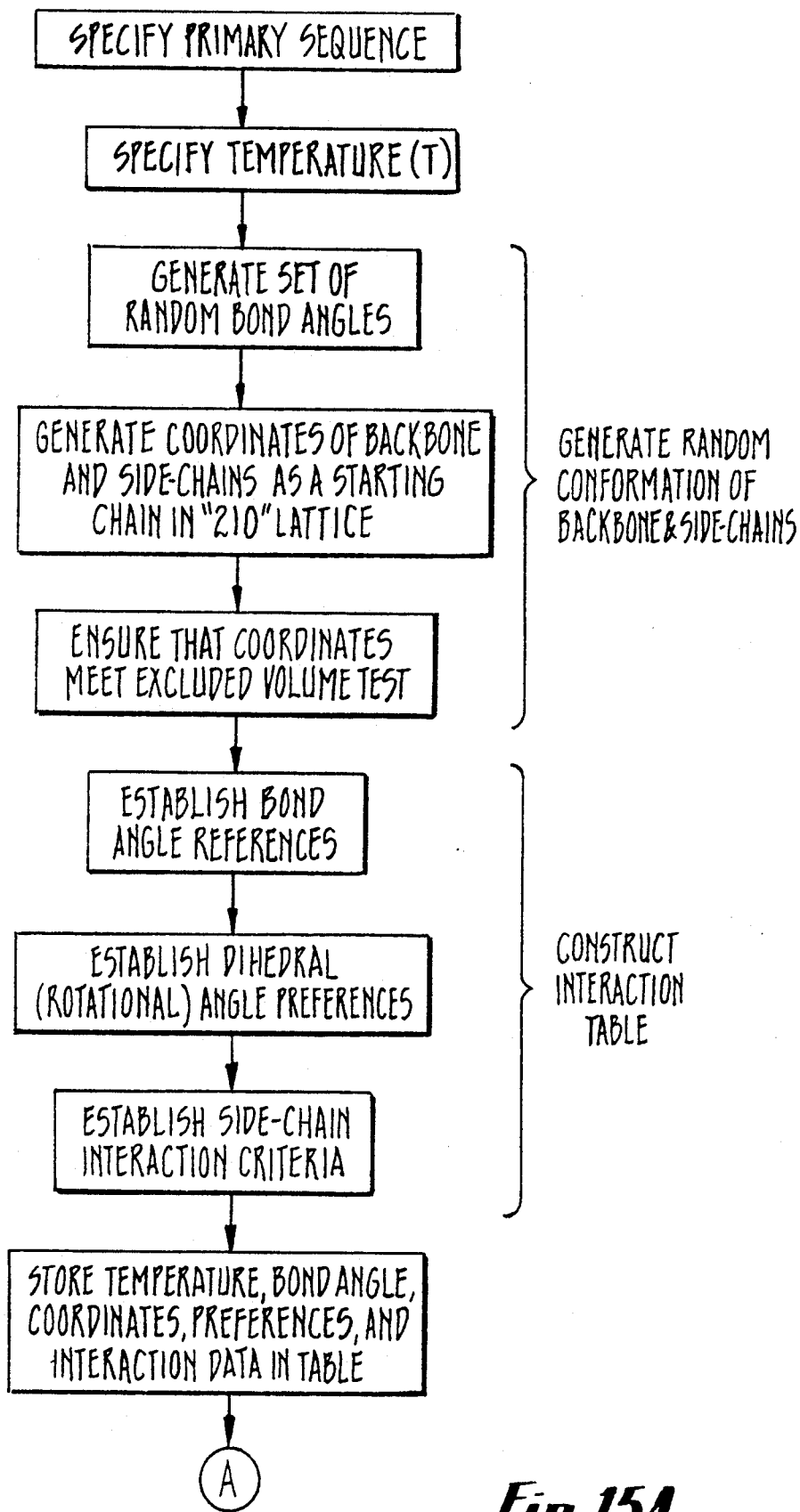
Figure 15B:
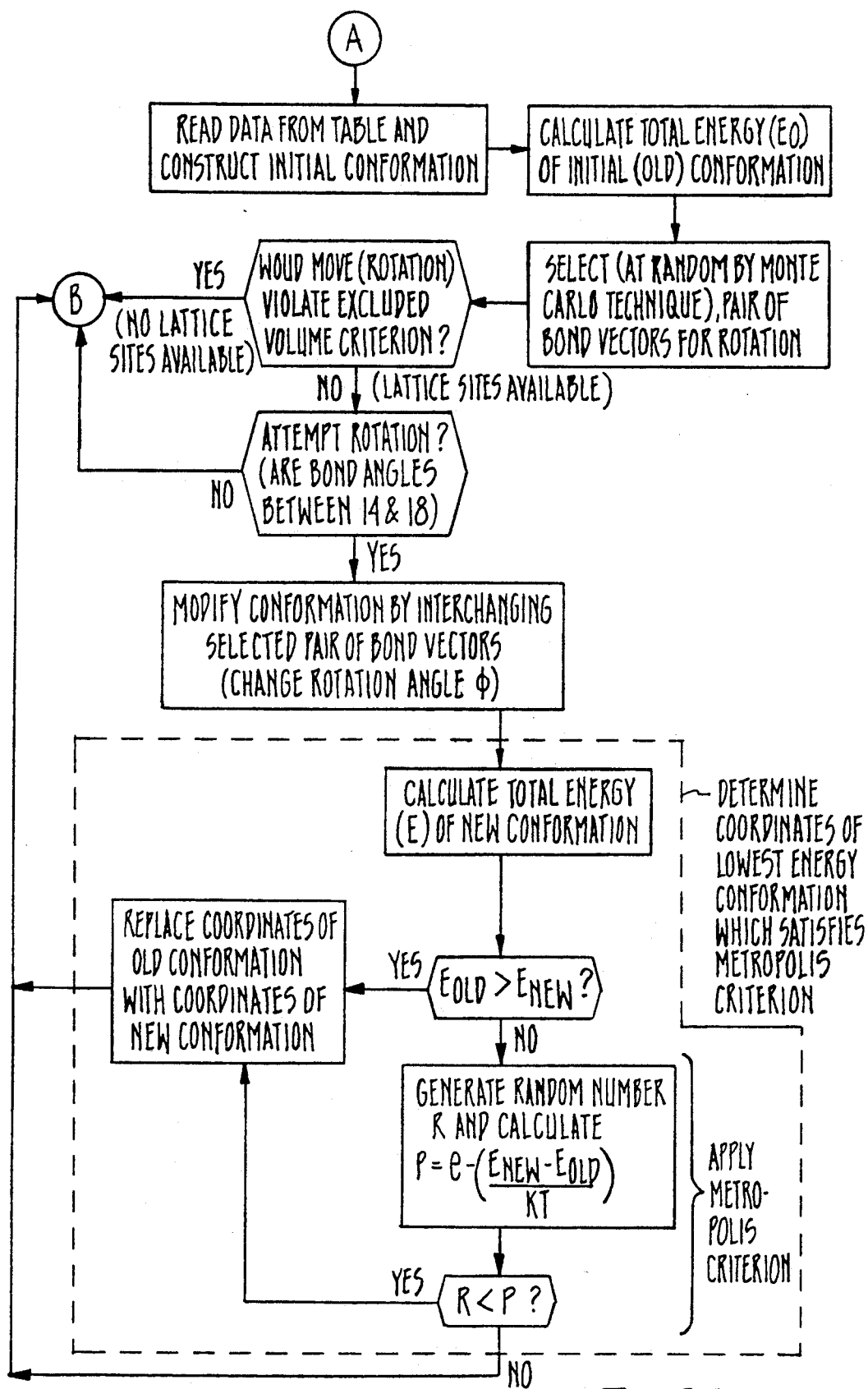
Figure 15C:
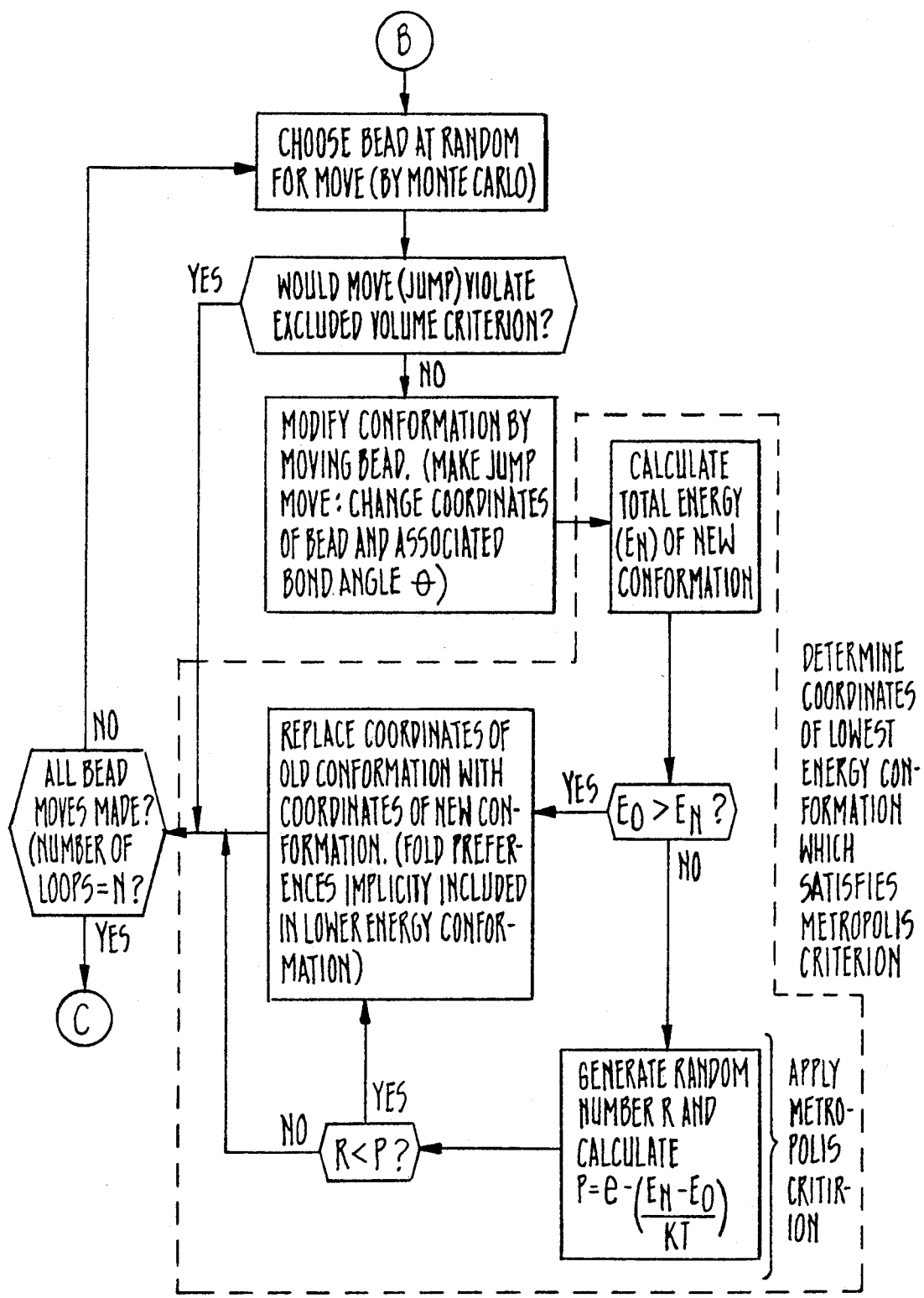
Figure 15D:
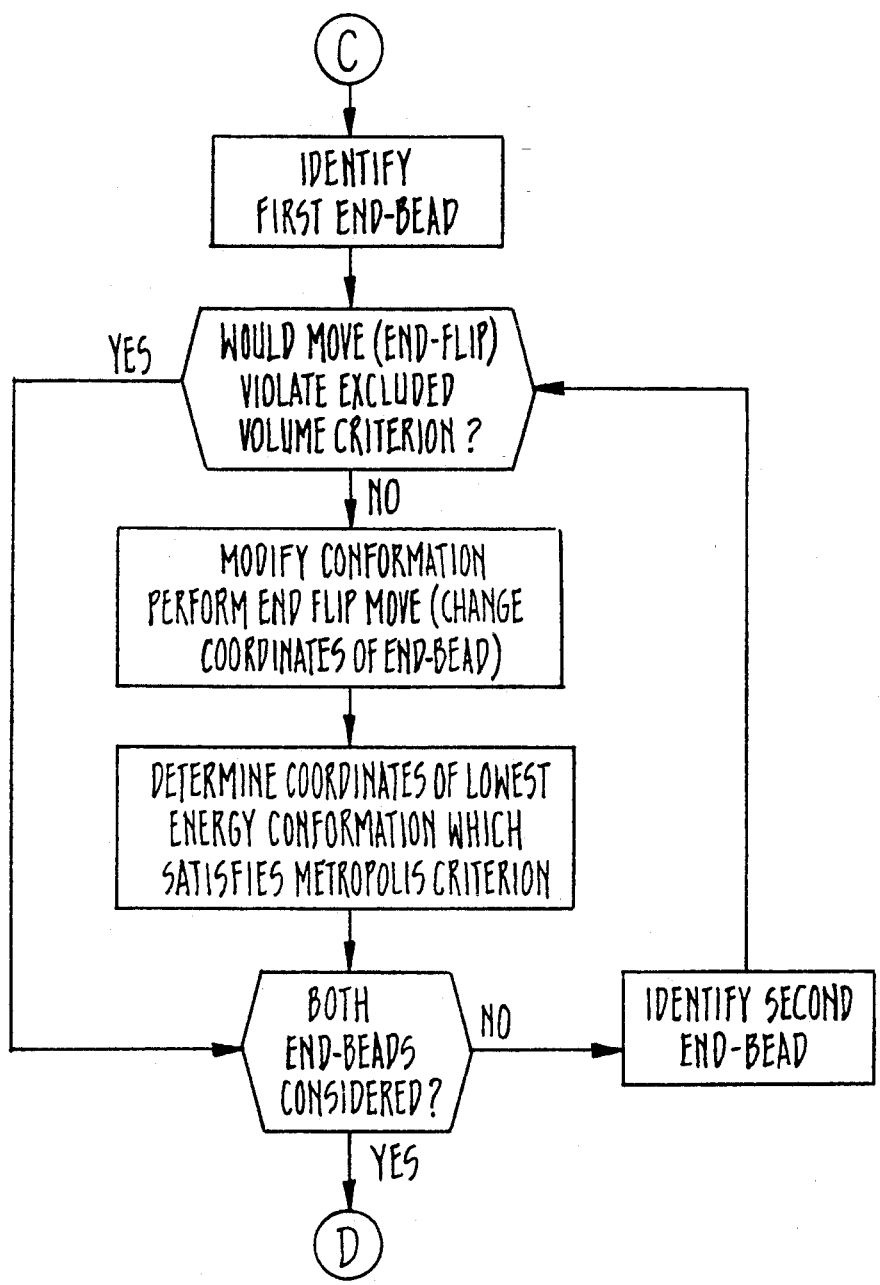

Turning now to a discussion of the folding pathway, it is seen that the sequence defines an observable pathway (trajectory) as it folds and makes the transition from its denatured (unfolded) conformation state to its native (folded) conformation state. A trajectory of a sample having the primary sequence $\epsilon_\alpha > \epsilon_\beta$, 1, 1.75, is shown in FIGS. 14A–B. The conformations at different times, are shown at different orientations that aid in the visualization of the folding process. At t=585,800 Monte Carlo time units, folding is seen to initiate from the central turn 115 between the $\beta$-hairpin composed of strands two 117 and three 119. (Folding is not unidirectional. $\beta$-strands may dissolve, as well as form, during the course of assembly.) If the conformation at t=585,900 is compared with that at t=586,000, it will be seen that a slight dissolution of the $\beta$-hairpin 121 has occurred. By t =586,300, the first $\beta$-hairpin 121 is almost fully assembled. However, by t=586,550, the majority of one of the two strands in the $\beta$-hairpin dissolves and, then, reforms at t=586,600. Then, there is a pause as the random coil tail 123 thrashes about, until the next native-like turn 125 forms. By t - 587,700, three of the four $\beta$-strands 117, 119, 127 are essentially in place. Thus, assembly to the three-member $\beta$-barrel intermediates takes 1,900 time steps from the beginning of folding. Throughout this process, the excluded volume of the chain hinders assembly. Most of the configurations of the denatured tail are nonproductive; the tail thrashes about until t=591,800 when it works its way into a position(s) that permits native state assembly. After which, the assembly becomes more rapid and, by t=592,250, the fully folded molecule forms. Thus, the three-member $\beta$-barrel is the long-lived intermediate, living for 4,550 time steps or 71% of the total elapsed time from the start of folding. The mechanism of assembly is best described as punctuated, on-site construction.

With respect to unfolding of a tertiary structure, in all instances unfolding is the reverse of folding. Typically, unfolding starts with either one of the external strands becoming denatured or an internal stand closest to the denatured tail becoming unfolded.

Computer System and Method

Referring now to FIGS. 3 and 15, a system and method are shown and described for simulating protein folding and determining three-dimensional (tertiary) structures of proteins.

The system comprises an input means 57 such as a keyboard for specifying (entering) selected amino acid sequences and other data such as temperature and fold preferences, a RAM (random access memory) 59 for storing such data, a ROM (read-only memory) 61 with a stored program, a CRT (cathode ray tube) display unit 63 and/or printer 65, an optional auxiliary disk storage device 67 for storage of relevant data bases, and a microprocessor 69 for performing, under control of the stored program, the steps of processing the entered data, simulating the folding of the protein from its unfolded state to its folded (tertiary) state, and displaying via the display unit (or printer) tertiary conformations of the protein in three dimensions.

A user enters the amino acid sequence data file from the auxiliary storage unit). In response to entry of the sequence data, the system inputs (specifies) the data for processing, stores the data in memory then processes it as shown in FIGS. 15A-F. Sample data of the type which may be input to the system is shown in Appendix E. In processing the data, the system generates a tertiary interaction matrix as shown in Appendix E and produces, in addition to a display of the protein's tertiary structure, a sample output as shown in Appendix E for tracking the simulation. As indicated above, the system operates under the control of a stored program. A listing of the program is shown in Appendix D.

Turning now to FIGS. 15A-F, in response to the specified data the system generates a random conformation of backbone and sidechain elements (residues). It does this by generating a set of random bond angles, then generating the coordinates of the backbone and sidechains as a starting chain in a 210 lattice (FIG. 4). The system then checks to determine if the excluded volume criterion is met, after which, it constructs an interaction table, a sample of which is shown in Appendix E. It proceeds to construct the interaction table by first establishing respective bond angle preferences, then establishing dihedral (rotational) angle preferences followed by establishing side-chain interaction criteria. The system then stores the temperature, bond angle, lattice coordinates, preferences, and interaction data in a table or matrix like that shown in Appendix E. Thereafter, the system reads the data from the table and constructs, by means of Monte Carlo simulation, a random conformation; following which, the system calculates the total energy of the conformation represented as ($E_{old}$). Thereafter, the system selects (at random by Monte Carlo simulation) a pair of bond vectors for rotation. It then checks if the rotation would violate the excluded volume criterion. If it would, the rotation is not attempted, and the system proceeds to the next step. If it would not violate the excluded volume criterion, another check is made to determine if the bond angles subtended by the bond vectors are between 14 and 18; if they are, it attempts the rotation. Otherwise, it does not attempt the rotation and proceeds to the next step. In performing rotation, the system modifies the conformation by interchanging a randomly selected pair of bond vectors. In other words, it proceeds to change the rotation angle $\phi$. Thereafter, the system proceeds to determine the coordinates of lowest energy conformation which satisfy the Metropolis criterion. It does this by first calculating the total energy ($E_{new}$) of the new modified conformation then comparing the total energy $E_{new}$ with the total energy of the old conformation $E_{old}$. If $E_{old}$ is greater than $E_{new}$, then the coordinates of the old conformation are replaced with the coordinates of the new conformation. The system then proceeds to the next step (step B) which is be described below. If $E_{old}$ is not greater than $E_{new}$ then, in compliance with the Metropolis criterion, a random number R is generated and the probability $$P = e^{\frac{-(E_{new} - E_{old})}{K_BT}}$$

is calculated. That probability is compared with the random number R. If R is less than P, the coordinates of the old conformation is replaced with the coordinates of the new conformation and the system proceeds to the next step (step B). If, however, R is not less than P, the system directly proceeds to the next step (Step B). At the next step, the system proceeds to choose a bead at random to move within the lattice. Before moving the bead, the system tests if the move (which is a jump-type move) would violate the excluded volume criterion. If no, it proceeds with the move. If yes, it does not proceed with the move, and proceeds instead to choose the next bead until all the beads in the chain have been checked for modification (movement). If the move would not violate the excluded volume criterion, the conformation is modified by moving the bead to a new lattice site. In other words, the bead would make a jump move which would change its coordinates and associated bond angle $\Theta$. After the move is made and the conformation is modified thereby, the system calculates the total energy of the new conformation, that is, the total energy $E_{new}$ in a similar manner as indicated earlier. $E_{new}$ is then compared with $E_{old}$, the energy of the previous conformation before the move. If $E_{old}$ is greater than $E_{new}$, then the coordinates of the old conformation are replaced with the coordinates of the new, and the next bead move is checked. If $E_{old}$ is greater than $E_{new}$, then the Metropolis criterion is applied (and the random number R is generated, and the probability P is calculated in the same manner as indicated earlier, as shown in FIG. 15A-F), and the random number R is compared with the probability P. If R is less than P, the coordinates of the old conformation are replaced with the coordinates of the new and the next bead move is checked. If R is not less than P, the next bead move is checked and the loop is repeated until all bead moves (i.e., the moves of all n beads) have been checked, at which time if all bead moves have been checked the system proceeds to the next step (step C). At this next step, the system proceeds to process the two end beads. It identifies the first end bead then checks if an end flip-type move would violate the excluded volume criterion. If no, it proceeds with the move. Otherwise, it aborts the move and proceeds to check the second end bead. In the event the move of the first end bead would not violate the excluded volume criterion, the system proceeds to modify the conformation by performing an end-flip move that changes the coordinates of the end bead. It then proceeds to determine the coordinates of the lowest energy conformation which satisfies the Metropolis criterion in the same manner as it did for the rotational and jump-type moves. After determining the coordinates of the lowest energy conformation which satisfy the Metropolis criterion, the system checks if both end beads are processed. If the second end beads remain to be processed, the system identifies the second end bead and proceeds to check whether an end flip move of the second end bead would violate the excluded volume criterion. If it would violate the criterion and both end beads have been considered, it then proceeds to the next step (step D). If it does not violate the criterion, then the system proceeds to modify the conformation by performing an end-flip move of the second end bead changing the coordinates of the second end bead. It then proceeds to determine the coordinates of the lowest energy conformation which satisfy the Metropolis criterion, after which it proceeds to the next step (step D). At this next step, the system selects a bond at random then searches for a U-shaped segment. It then checks, after finding the U-shaped segment, whether a move of a translation (wave motion) type move would violate the excluded volume criterion. If not, it proceeds with the modification. If it does violate the excluded volume criterion, it aborts the move and proceeds to check if all the jump-type moves were made. If all were made, it proceeds to the next step (step E). However, if the move would not violate the excluded volume criterion, the system proceeds to modify the conformation by performing the translation/wave-motion-type move changing the coordinates of the beads defining the U-shaped segment. The system then determines the coordinates of lowest energy conformation which satisfy the Metropolis criterion, after which it proceeds to check if all the jump-type moves were made. If all the jump-type moves are not made (completed), it starts the loop again. One complete loop is represented by one rotational move, n jump-type moves, two end-flip moves, and one U-shaped move. After the loops have been completed and all moves made and/or aborted, the system checks to determine if the chain is still positioned near the center of the lattice. If it isn't, it moves the chain to the center of the lattice and adjusts its coordinates accordingly. Thereafter, the system displays a three-dimensional representation of the protein structure and repeats the process (processing) for a predetermined number of times. However, if upon checking whether the chain is still positioned near the center of the lattice, it finds that it remained at the position near the center of the lattice, the system immediately proceeds to displaying the three-dimensional representation of the protein, then repeats the process. After the three-dimensional coordinates of the tertiary protein structure are generated for display, a graphics program such as SYBYL (which is commercially available from Tripost Associates Corporation of St. Louis, Mo.) is used by the system to display the tertiary structure corresponding to the coordinates. Sample display output is presented in FIG. 1. Sample printed output is presented in Appendix E.

Figure 16:
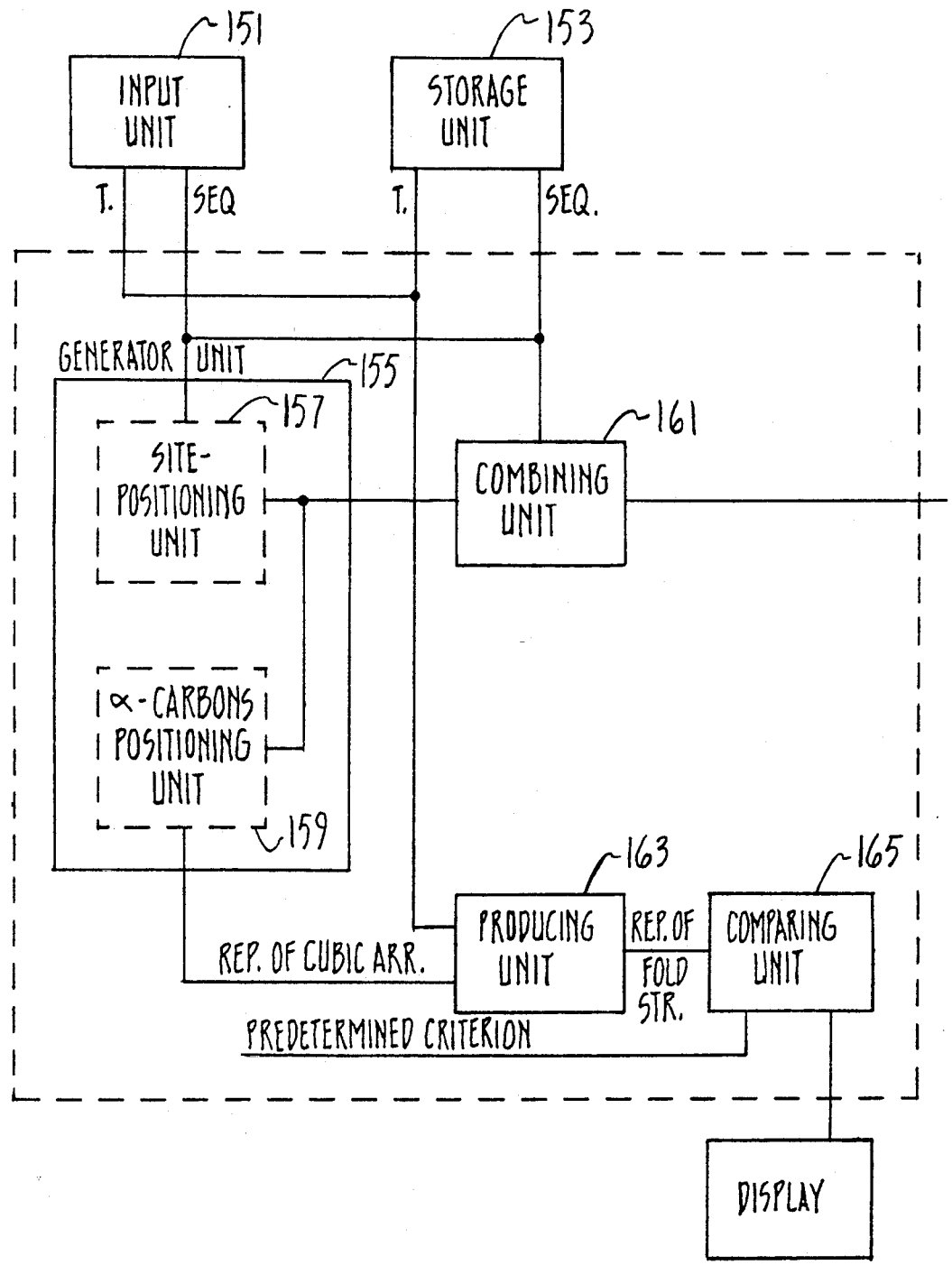
FIG. 16 is a block diagram showing an alternate embodiment of the processor of FIG. 15.

An alternative embodiment of the system is presented in FIG. 16 comprising a keyboard 151 for entering data representing temperature and amino acid sequences, a RAM 153 for storing the entered data, and a unit 155 for generating a representation of a lattice, including unit 157 for positioning lattice sites, and unit 159 for positioning α-carbons relative to the lattice sites. The system includes a unit 161 for combining the generated lattice representation and the sequence of residues, a unit 163 for producing representations of protein structures, and a unit 165 for comparing the protein structure representations to a predetermined criterion and for selecting one of the protein structure representations for display.

APPENDIX A

The following is a description of various lattice model rules which must be followed for constructing conformations of various sidechains linked to various backbone configurations.

As shown in FIG. 8, let the $i^{th}$ bond vector $b_i$ connect α-carbons $(i-1)$ and $(i)$. Then, for a given backbone conformation, $r^2_\Theta$ may be defined as follows:

$$r^2_\Theta = (b_i + b_{i+1})^2$$

On the 210 lattice, the allowed values of $r^2_\Theta$ are 6,8,10,12,14,16 and 18. Any other value of $r^2_\Theta$ is rejected as not realistic or not representable on the 210 lattice. For a given backbone conformation, four sidechain vectors are constructed. The center of sidechain interaction is located at the site defined by a diamond lattice vector d 34, of the type $(\pm 1, \pm 1, \pm 1)$, which points from the center of the α-carbon to the point $(\pm 1, \pm 1, \pm 1)$. The other three vectors $f_1$, $f_2$ and $f_3$ 36,38,40 are of the fcc type, whose sum is twice that of the diamond lattice vector d 34. The vector d has left-handed chirality (L). With respect to the backbone, vector d points toward the N-terminus of the sequence. The orientation angle is generally not less than 60°.

Pseudovector p is defined as the cross-product of $b_{i+1}$ and $b_i$:

$$p = b_{i+1} < b_i$$

and w is defined as:

$$w = b_i - b_{i+1}$$

The general procedure for the calculation d, $f_1$, $f_2$ and $f_3$ is given as follows: If $d = (d_x, d_y, d_z)$, then $$f_1 = (d_x, d_y, 0)$$

$$f_2 = (d_x, 0, d_z)$$

$$f_3 = (0, d_y, d_z).$$

In the following, use is made of the function isgn(x), where:

$$isgn(x) = \begin{array}{l} 1 x \geq 0 \\ -1 x < 0. \end{array}$$

If $r^2_\Theta = 14$, then $$d_x = isgn(p_x)$$

$$d_y = isgn(p_y)$$

$$d_z = isgn(p_z)$$

If $r^2_\Theta = 8, 12$ or $16$, then $$d_x = isgn(p_x - 2b_{x,i+1})$$

$$d_y = isgn(p_y - 2b_{y,i+1})$$

$$d_z = isgn(p_z - 2b_{z,i+1})$$

where $$b_{i+1} = (b_{x,i+1}, b_{y,i+1}, b_{z,i+1}).$$

If $r^2\Theta = 6$ or $10$, then $$d_x = isgn(p_x + w_x)$$

$$d_y = isgn(p_y + w_y)$$

$$d_z = isgn(p_z + w_z)$$

And, if $r^2\Theta = 18$, and if $p_x \cdot p_y \neq 0$, then $$d_x = isgn(p_x)$$

$$d_y = isgn(p_y)$$

$$d_z = isgn(p_z).$$

Otherwise, $$d_x = isgn(p_x + w_x)$$

$$d_y = isgn(p_y + w_y)$$

$$d_z = isgn(p_z + w_z).$$

APPENDIX B

A generalized master equation is shown below:

$$\frac{\delta p(\{i\}, t)}{\delta t} = \sum_{\{i'\}} \cdots \Sigma k_f p(\{i\}|\{i'\})q(\{r_i\}) - k_b p(\{i'\}|\{i\})q(\{r'_i\}) \quad (1)$$

where
- $\{i\}$ represents a first set of vectors;
- $\{i'\}$ represents a second set of vectors;
- $p(\{i\}, t)$ represents the probability of finding a set of vectors $\{i\}$ at a time t;
- $k_f$ represents rate of increase of the set $\{i\}$ in size (membership) due to move of bead from set $\{i,\}$ to set $\{i\}$;
- $k_b$ represents rate of decrease of the set $\{i\}$ in size due to move of bead to set $\{i'\}$ from set $\{i\}$;
- $\{r_i\}$ and $\{r'_i\}$ represent coordinates of the set of bond vectors $\{i\}$ and $\{i,\}$;

$q(\{r_i\})$ represents an excluded volume function
$(i')$ $= 1$; if $\{r_i\}$ are unoccupied
$(i')$ $= 0$; if $\{r_i\}$ are occupied
$(i')$

- $p(\{i\}|\{i'\})$ represents the probability of occupying set $\{i\}$ upon moving from set $\{i'\}$;
- $p(\{i'\}|\{i\})$ represents the probability of occupying set $\{i'\}$ upon moving from set $\{i\}$;
and the relationship between $k_f$ and $k_b$ may be expressed as:

$$\frac{K_f}{K_B} = \exp\left\{\frac{-(U(i) - U(i'))}{K_B T}\right\}$$

where
- $U\{i\}$ represents the total energy of the protein in the $i^{th}$ conformation;
- $U\{i'\}$ represents the total energy of the protein in the $i'^{th}$ conformation;
- $k_B$ represents Boltzmann's constant; and
- T represents temperature (in degree Kelvin) of the protein.

A bead represents an amino acid residue comprising a full sidechain (i.e., four lattice sites) and backbone segment (i.e., seven lattice sites). A bead is shown, for example, in FIGS. 5 and 9. In terms of the above equation, the probability of finding a set of vectors $\{i, i+1\}$ at a time t in a two-bond jump-type move of a bead from one coordinate position $(r_i)$ to another coordinate $(r_{i'})$ may be expressed as:

$$\frac{P(\{i, i+1\}, t)}{t} =$$

$$\sum_{i', i'+1} k_f P(i; i+1|i'; i'+1; \Theta) q(r_i) -$$
$$\Theta_{i', i'+1} = \Theta_{i, i+1}$$

$$k_b P(i'; i'+1|i; i+1; \Theta) q(r_{i'})$$

where,
- i and i+1 represents a first pair of vectors;
- i' and i'+1 represents a second pair of vectors; and
- $\Theta$ represents the bond angle between vectors (bonds) i and i+1 and between i' and i'+1.

In addition to the single-bead jump-type move described above, a conformation may be modified by rotational and/or translational motion of one or more beads, as shown for example in FIGS. 10 and 11.

APPENDIX C

Calculation of the Denatured State Free Energy

In this appendix, an expression for the free energy of the unfolded state of a model protein confined to a 210 lattice is calculated. Two cases are examined. The first corresponds to the situation when the torsional potential $\epsilon_\phi$ equals zero, and the second corresponds to the more general case when $\epsilon_\phi$ is non-zero.

With respect to the lattice, each of the twenty-four possible vectors connecting the lattice sites may be given a number one through twenty-four, as follows:

| | | (C-1) |
|---|---|---|
| 1 = (2, 1, 0)  | 13 = (0, −1, −2) | |
| 2 = (2, 0, 1)  | 14 = (0, −2, −1) | |
| 3 = (2, −1, 0) | 15 = (0, 1, −2)  | |
| 4 = (2, 0, −1) | 16 = (0, −2, 1)  | |
| 5 = (1, 2, 0)  | 17 = (−1, 2, 0)  | |
| 6 = (1, 0, 2)  | 18 = (−1, 0, 2)  | |
| 7 = (1, −2, 0) | 19 = (−1, −2, 0) | |
| 8 = (1, 0, −2) | 20 = (−1, 0, −2) | |
| 9 = (0, 1, 2)  | 21 = (−2, 1, 0)  | |
| 10 = (0, 2, 1) | 22 = (−2, 0, 1)  | |
| 11 = (0, −1, 2)| 23 = (−2, −1, 0) | |
| 12 = (0, 2, −1)| 24 = (−2, 0, −1).| |

To specify the conformation of the chain, given the location of the first bead, a sequence of N−1 numbers, ranging from 1 to 24, is specified with the first bond vector (vector 1) chosen arbitrarily as vector (2,1,0), the second vector must satisfy the constraint $6 \leq r^2_\Theta \leq 18$. There are 18 such possibilities, and there are four states such that $r^2_\Theta=6$. The second vector can be $(0,-2,\pm 1)$ and $(-1,0,\pm 2)$. There are two such possibilities when $r^2_\Theta=8$, namely $(0,-1,\pm 2)$. When $r^2_\Theta=10$, there are two possibilities as well, $(-1,2,0)$ and $(1,-2,0)$. If $r^2_\Theta=12$, again, there are two possibilities with the allowed second vectors being $(0,1,\pm 2)$. Turning to the $r^2_\Theta=14$ case, there are a total of four possibilities $(0,2,\pm 1)$ and $(1,0,\pm 2)$. If $r^2_\Theta=16$, there is one possibility, $(2,-1,0)$. Finally, for $r^2_\Theta=18$, there are three possibilities $(2,0,\pm 1)$ and $(1,2,0)$. In general, for a given vector number i, there are eighteen allowed vectors; subsequent allowed vectors vary depending on the particular vector that precedes them.

A pseudo inner product may be defined (by analogy to orthonormal basis sets) as follows:

$$<i,j> = 1 \qquad (C-2)$$

if the two vectors i and j are allowed, and $$<i,j> = 0 \qquad (C-3)$$

if the two vectors i and j are not allowed.

Denatured State Partition Function $\epsilon_\phi=0$

In the absence of a torsional potential that serves to couple adjacent bond angle states (and which, therefore, introduces cooperativity into the model), the internal partition function of the denatured state, $Z^0_D$, may be obtained from $$Z_D^0 = J^* \prod_{i=2}^{N-1} U_{D,i} J. \qquad (C-4)$$

where $J^*$ is a row vector of dimension 24, consisting of a 1 followed by twenty-three zeros, J is a column vector consisting of twenty-four ones, and $U_{D,i}$ is a 24×24 matrix associated with the ith residue, each row of which contains 18 non-zero elements and 6 zero elements. $U_{D,i}$ may be expressed as:

$$U_{D,i}(k,l) = <k,l>\exp(-\epsilon_{\Theta,i}(k,l)/k_BT). \qquad (C-5)$$

As shown below, the configurational partition function can be written as the product of the internal bond angle partition functions associated with each bond angle state $z_{\Theta,i}$:

$$Z_D^0 = \prod_{i=2}^{N-1} Z_{\Theta,i} \qquad (C-6)$$

The matrix product in equation C-4 is of the form:

$$Z_D^0 = \sum_{k=1}^{24}\sum_{l=1}^{24}\cdots\sum_{r=1}^{24}\sum_{s=1}^{24} U_{D,2}(1,k)U_{D,3}(k,l)\cdots \qquad (C-7)$$

$$U_{D,N-2}(u,r)U_{D,N-1}(r,s).$$

Given that the sum of all the elements in the columns is independent of the row index (i.e., each row has the same set of bond angle states that must be summed over), the sum of the products can be expressed as the product of the sums, as follows:

$$Z_D^0 = \prod_{i=2}^{N-1}\sum_{k=1}^{24} U_{D,i}(1,k). \qquad (C-8)$$

which is identical to equation C-6 because $z_{\Theta,i}$ is the same as $$Z_{\Theta,l} = \sum_{k=1}^{24} U_{D,l}(1,k). \qquad (C-9)$$

Thus, the separability of the partition function is established. The free energy of the denatured state is simply $$\epsilon_\phi \neq 0 \qquad A_D^0 = -k_BT\ln(Z_D^0) \qquad (C-10)$$

To include the effect of non-zero $\epsilon_\phi$ into the calculation of the partition function, the chain is divided into statistical weight matrices associated with pairs of bonds. That is, the partition function is calculated as $$Z_D = J^*_{576} \prod_{i=2;\text{even}}^{l_u} U_i^\phi J_{576}. \qquad (C-11)$$

where $J^*_{576}$ is a row vector of dimensionality 576 whose first term is unity and remaining terms are zero. $J_{576}$ is a column vector of dimensionality 576, all of whose elements are unity. $l_u=N$ if N is even, and $l_u=N-1$ if N is odd. $U^\phi_i$ is a 576 by 576 matrix. For convenience in setting up $U^\phi_i$, the torsional angles are labeled from 3 to $N-1$, rather than from 2 to $N-2$ as in the main text. For $i=2$, one merely has to account for the bond angle associated with the second residue. Choosing the first bond as vector 1, the only non-zero elements of $U^\phi_2$ are $$U^\phi_2(1,j) = <1,j>\exp(-\epsilon_{\Theta,2}(1,j)/K_Bt). \qquad (C-12)$$

We next consider the case where $2<i<l_u$. Let the bond vectors associated with residues $i-3$, $i-2$, $i-1$ and i be labelled by j,k,l,m, respectively. The jth bond vector connects residues $i-3$ to $i-2$. The rows of $U^\phi_i$ (row,column) are obtained from j and k by $$\text{row} = (j-1)24 + k \qquad (C-13)$$

$$\text{col} = (l-1)24 + m \qquad (C-14)$$

In defining the statistical weight matrix $U_\phi(j,k,l,i)$ associated with the torsional potential due to the particular sequence of the three bonds j,k,l (where k goes from vertex $i-1$ to i), the distance $r_{i-2,i+1}$ between residues $i-2$ to $i+1$ is considered. If the square of this distance is less than 3, then due to the hard core stearic repulsion, $$U_\phi(j,k,l,i) = 0 \qquad (C-15)$$

If $r^2_{i-2,i+1}=3$, then $$U_\phi(j,k,l,i) = <j,k><k,l>\exp[-(\epsilon_\phi(j,k,l)+3\cdot\epsilon_{rep})/k_BT] \qquad (C-16)$$

If $r^2_{i-2,i+1}=5$, then $$U_\phi(j,k,l,i) = <j,k><k,l>\exp[-(\epsilon_\phi(j,k,l)+\cdot\epsilon_{rep})/k_BT] \qquad (C-17)$$

For all other $r^2_{i-2,i+1}$, $$U_\phi(j,k,l,i) = <j,k><k,l>\exp[-(\epsilon_\phi(j,k,l))/k_BT] \quad \text{(C-18)}$$

Thus, local short range repulsions are accounted for in the treatment as well.

For $2<i<l_u$, if $l_u$ is even, and for $2<i\leq l_u$ is odd, then $$U^\phi(j,k,l,m) = <j,k><k,l><l,m>\exp^{(-(\epsilon\theta,i-1(k,l)+\epsilon\theta,i(l,m))/KBT)}U_\phi(j,k,l,i-1)U_\phi(k,l,m,i) \quad \text{(C-19)}$$

If $i=l_u$, and $l_u$ is even then, since vertex i is at the end of the chain, it is necessary to only account for the last bond angle and torsional angle associated with vertex $N-1$. To make this last matrix conformable with the previous matrices (e.g., vector type 1), an extra bond is appended at the end of the chain, giving:

$$U^\phi_{l_u=N}(j,k,l,N) = \quad \text{(C-20)}$$
$$<j,k><k,l><l,1>\exp^{(-(\epsilon\theta,N-1(k,l)/KBT)}U_\phi(j,k,l,N-1)$$

From the above definitions of U, J and Z, it is seen where the free energy $A_D$ of the denatured state can be determined from the equation:

$$A_D = -k_BT\ln(Z_D).$$

APPENDIX D

```
c     only left handed diamond lattice  vectors can interact
c     revised to include a finer trajectory
c
c     generalized to include other  favoring of torsional potentials
c
c     8/19/89
c     **FIXES THE PROBLEM OF GLYCINES AT POSITIONS 3 AND LENF-2
c     **PRESENT IN ALL PREVIOUS VERSIONS
c
c     ncglyshort.f is a version of ncthermshort.f but which introduces
c     thermalization into the wave displacements
c
c     generates short trajectories
c     like jstherm but it also
c     calculates the number of native contacts
c
c
c     ****************************************************************
c         SIDECHAINS ONLY A DISTANCE OF THE SQUARE ROOT OF TWO CAN INTERACT
c     all other faces of the sidechain are hard core
c     produces equivalent interaction for 12 and 16 states
c         should produce shifted sq(10) for beta barrel like states
c     with hydrophoblic core
c     program uses setind.f and ergd.f
c
c     ****************************************************************
c     *                                                              *
c     *               P R O T E I N    201                           *
c     *                 THE NEXT GENERATION                          *
c        *                                                        *
c     ****************************************************************
c
c     WITH GLYCINE (NO SIDE GROUP) CODED AS := 0 (zero) HYDDROPHOBICITY
c     NO GLYCINE ASSUMED ON THE THREE ENDS SEGMENTS. ALLOWS FOR 6 STATE
c
c         PROGRAM SIMULATES SIMPLIFIED MODELS OF GLOBULAR PROTEINS BASED ON
c     THE   " 2 1 0 " LATTICE ALPHA-CARBON REPRESENTATION. INCLUDES SOME
c     DETAILS OF A SEQUENCE DESCRIPTION.  HAS BUILD-IN CHIRALITY OF THE
c     AMINOACIDS.   ASYMETRIC METROPOLIS SCHEME WITH A VARIETY OF LOCAL
c     REARRANGEMENTS OF MAIN (AND SIDE GROUPS) CHAIN BACKBONE. EDITED BY
c     AK - FEB. 1989 ST. LOUIS.
c
c     REPULSIVE INTERACTIONS SQRT(5)
c     WITH 'WAVE' MOTIONS, HYDROGEN BONDS, COOPERATIVITY, SIDE GROUPS..
c     THREE (+1) SITE SIDE GROUPS
c     NOTE THAT THIS PROGRAM USES EREP5,EHB,setini,REMOVEG,LOOKG,ERGG
c     setind.f allows for interactions between left handed chirality
c     diamond lattice vector
c     vaxran version
```

```
c     ****************************************************************
c     this version of program was created on 5/12/89
c     ****************************************************************
c     4/18/89
c     constructs the torsional potential in the progarm
c     PHISEQ used
c     ah is the 1./temp in the thermalization step of the waves and
c     rotations
c     at the head of the INPUT file
c     ****************************************************************
c
c
c     THE LATERAL TRANSLATION OF A STRING ADDED
c
c     WITH SPECIFFICATION OF THE TORSIONAL POTENTIAL FOR SEQOENCE
c     THIS IS GIVEN IN APH(24,24,24,'LENGTH') ARRAY WHICH HAS TO BE
c     PREPARED AS AN INPUT FILE  FILENAME='PHIPAT' USE AKPHIMAKE
c
c     LIST OF BACKBONE VECTORS - USE FOR ANALYSE OF LOCAL GEOMETRY
c     ................................................................
c
c     VECTOR NR 1        2  1  0           0 -1  1
c               2           2  0  1           0  1 -1
c               3           2 -1  0           0 -1 -1
c     (CODES ALSO 4        2  0 -1           0  1  1
c     FOR DIAMOND
c     LATTICE TL)  5       1  2  0          -1  1  0
c               6       1  0  2           1 -1  0
c               7          1 -2  0          -1  0  1
c               8          1  0 -2           1  0 -1
c
c               9          0  1  2          -1  0 -1
c              10          0  2  1           1  0  1
c              11          0 -1  2          -1 -1  0
c              12          0  2 -1           1  1  0
c
c              13          0 -1 -2          F. C. C.
c              14       0 -2 -1       LATTICE
c              15       0  1 -2                VECTORS
c              16          0 -2  1
c
c              17         -1  2  0
c                    18          -1  0  2
c                    19          -1 -2  0
c              20         -1  0 -2
c
c     VECTOR NR   21      -2  1  0
c     IS          22      -2  0  1
c     THE         23      -2 -1  0
c     CODE        24      -2  0 -1
c
c     ................................................................
c
      IMPLICIT INTEGER (I-Z)
      REAL vaxran
      double precision etot,etot2,cv,anct,ant
      real asumr2,asums2,as2
      LOGICAL GOODC,LOOK
      DIMENSION ASTR(100),IDIS(100),STATN(100)
      DIMENSION astrr(100),RIDIS(100),RSTATN(100),RIHAND(100)
      DIMENSION XYZ(100,100,100), X(100),Y(100),Z(100),ihand(100)
      DIMENSION VECTOR(-2:2,-2:2,-2:2), VX(24),VY(24),VZ(24)
      DIMENSION ICONF(24,24),GOODC(24,24)
      DIMENSION VECT1(24,24,5),VECT2(24,24,5)
      DIMENSION SIDGR1(24,24),SIDGR2(24,24),SIDGR3(24,24)
      DIMENSION ICA(0:100), STLX(13),STLY(13),STLZ(13)
      DIMENSION AC(100,20),AM(100,100),IHYD(100),IC6(100)
      DIMENSION IC9(100),IC10(100),IC12(100),IC14(100),IC16(100),IC18(100)
      DIMENSION PRODV(24,24),ICAO(100), APH(24,24,24,100)
      DIMENSION XNEW(100),YNEW(100),ZNEW(100),INDGL(100)
      dimension iflip(20,5),inc(100,100)
      dimension S1X(24,24)
```

```
      dimension S1Y(24,24)
      dimension S1Z(24,24)
      dimension xt(100),yt(100),zt(100)
c     XYZ - OCCUPANCY LIST WITH SIDE GROUPS (0,-1,INDEX!!!)
c     X, Y, Z - EXPLICITE COORDINATES OF I-LENF BEADS
c     ICONF - R2(VECTOR CODE, VECTOR CODE)
c     ICA - EXPLICITE VECTORS DOWN THE CHAIN
c     APH - ENERGY OF A GIVEN SEQUENCE OF THREE BONDS, DEPENDS
c           ON CONFORMATION AND THE NUMBER OF THE RESIDUE
c
      DATA VX /4*2,4*1,8*0,4*-1,4*-2/
      DATA VY /1,0,-1,0,2,0,-2,0,1,2,-1,2,-1,-2,1,-2,2,0,-2,0,1,0,-1,0/
      DATA VZ /0,1,0,-1,0,2,0,-2,2,1,2,-1,-2,-1,-2,1,0,2,0,-2,0,1,0,-1/
c
c     FCC LATTICE VECTORS (AND 000)
      DATA STLX /4*0,-1,1,-1,1,-1,1,-1,1,0/
      DATA STLY /-1,1,-1,1,1,-1,4*0,-1,1,0/
      DATA STLZ /1,-1,-1,1,2*0,1,-1,-1,1,3*0/
c
c     TETRAHEDRAL LATTICE VECTORS c     DATA TLX /1,-1,1,-1,1,-1,1,-1/
c     DATA TLY /-1,1,-1,1,1,-1,1,-1/
c     DATA TLZ /-1,1,1,-1,-1,1,1,-1/
c
c     CODING THE VECTORS TO THE ARRAY
c
      DO XX=-2,2
      DO YY=-2,2
      DO ZZ=-2,2
      VECTOR(XX,YY,ZZ)=0
      ENDDO
      ENDDO
      ENDDO
            VECTOR(2,1,0)=1
            VECTOR(2,0,1)=2
            VECTOR(2,-1,0)=3
            VECTOR(2,0,-1)=4
      VECTOR(1,2,0)=5
      VECTOR(1,0,2)=6
      VECTOR(1,-2,0)=7
      VECTOR(1,0,-2)=8
            VECTOR(0,1,2)=9
            VECTOR(0,2,1)=10
            VECTOR(0,-1,2)=11
            VECTOR(0,2,-1)=12
      VECTOR(0,-1,-2)=13
      VECTOR(0,-2,-1)=14
      VECTOR(0,1,-2)=15
      VECTOR(0,-2,1)=16
            VECTOR(-1,2,0)=17
            VECTOR(-1,0,2)=18
            VECTOR(-1,-2,0)=19
            VECTOR(-1,0,-2)=20
      VECTOR(-2,1,0)=21
      VECTOR(-2,0,1)=22
      VECTOR(-2,-1,0)=23
      VECTOR(-2,0,-1)=24 c     ..............................................................
c
c     LIST OF CONFORMATIONS - THE SUM OF TWO VECTORS
c     ..............................................................

DO I=1,24
      DO J=1,24
      ICONF(I,J)=(VX(I)+VX(J))**2+(VY(I)+VY(J))**2+(VZ(I)+VZ(J))**2
      IDOTP=IABS(VX(I)*VX(J)+VY(I)*VY(J)+VZ(I)*VZ(J))
      IF(IDOTP.EQ.5) PRODV(I,J)=1
      ENDDO
      ENDDO
c
```

```
C       THE CODE OF A VECTOR READS  AS CODE=VECTOR(X,Y,Z)   (1 TO 24)
C       AND VICE VERSA COORDINATES READ AS X=VX(CODE)...............
C
C       .............................................................
C
C       LIST OF ACCEPTABLE CONFORMATIONS  6-18       (LOGICAL TABLE)
C       .............................................................
C
        DO I=1,24
        DO J=1,24
        IF(ICONF(I,J).LT.6.OR.ICONF(I,J).GT.18) THEN
C               6,8,10,12,14,16, AND R2=18 ALLOWED
            GOODC(I,J)=.FALSE.
            ELSE
            GOODC(I,J)=.TRUE.
            END IF
        ENDDO
        ENDDO

C
C       .............................................................
C
C       FLIP-TWIST ARRAY GIVES A DIRECT PREDICTION OF THE NEW CONF. STATE
C       VECT1(I,J,K) GIVES A FIRST VECTOR AFTER JUMP FROM SEQUENCE OF I-J
C       TO NEW STATES (SOMETIMES DEGENERATED) K=1,..5 < READS AS A CODE >
C       .............................................................
C
        DO I=1,24
        DO J=1,24
        IF(GOODC(I,J)) THEN
            WX=VX(I)
            WY=VY(I)
            WZ=VZ(I)
            NX=VX(J)
            NY=VY(J)
            NZ=VZ(J)
            VECT1(I,J,1)=J
            VECT1(I,J,4)=J
            VECT1(I,J,5)=J
            VECT2(I,J,1)=I
            VECT2(I,J,4)=I
            VECT2(I,J,5)=I
            ICONA=(ICONF(I,J)-4)/2
            GO TO (6,1,2,3,2,5,2) ICONA
C                                       CONFORMATION R2=6
C                                       FOUR POSSIBILE ARRANGEMENTS
6           SX=WX+NX
            SY=WY+NY
            SZ=WZ+NZ
            IF(IABS(SX).EQ.2) THEN
                IF(SY.NE.SZ) THEN
                        WY=-WY
                        WZ=-WZ
                        NZ=-NZ
                        NY=-NY
                        ENDIF
                WX1=WX
                WX2=NX
                WY1=WZ
                WZ1=WY
                    WY2=NZ
                    WZ2=NY
                GO TO 15
                ENDIF
            IF(IABS(SY).EQ.2) THEN
                IF(SX.NE.SZ) THEN
                        WX=-WX
                        WZ=-WZ
                        NX=-NX
                        NZ=-NZ
                        ENDIF
                WY1=WY
                WY2=NY
```

```
                WX1=WZ
                WZ1=WX
                    WX2=NZ
                    WZ2=NX
                GO TO 15
                ENDIF
            IF(IABS(SZ).EQ.2) THEN
                IF(SX.NE.SY) THEN
                        WX=-WX
                        WY=-WY
                        NX=-NX
                        NY=-NY
                        ENDIF
                WZ1=WZ
                WZ2=NZ
                WX1=WY
                WY1=WX
                    WX2=NY
                    WY2=NX
                ENDIF
15          N1=VECTOR(WX1,WY1,WZ1)
            N2=VECTOR(WX2,WY2,WZ2)
            VECT1(I,J,2)=N1
            VECT2(I,J,2)=N2
            VECT1(I,J,3)=N2
            VECT2(I,J,3)=N1
            GO TO 7
C                                       CONFORMATION R2=8
1           MX=1
            MY=1
            MZ=1
            IF(IABS(WX).EQ.1) MX=-1
            IF(IABS(WY).EQ.1) MY=-1
            IF(IABS(WZ).EQ.1) MZ=-1
            PX=WX*MX
            PY=WY*MY
            PZ=WZ*MZ
            I2=VECTOR(PX,PY,PZ)
            LX=NX*MX
            LY=NY*MY
            LZ=NZ*MZ
            J2=VECTOR(LX,LY,LZ)
            VECT1(I,J,2)=I2
            VECT2(I,J,2)=J2
                VECT1(I,J,4)=I2
                VECT2(I,J,4)=J2
                VECT1(I,J,5)=J2
                VECT2(I,J,5)=I2
            VECT1(I,J,3)=J2
            VECT2(I,J,3)=I2
            GO TO 7
C
C                                       CONFORMATION R2=10
C                                       CONFORMATION R2=14
C                                            CONFORMATION R2=18
2           VECT1(I,J,2)=J
            VECT2(I,J,2)=I
            VECT1(I,J,3)=J
            VECT2(I,J,3)=I
            GO TO 7
C                                       CONFORMATION R2=12
3           TEMPCO=3*WX*NX+2*WY*NY+WZ*NZ
            SX=WX+NX
            SY=WY+NY
            SZ=WZ+NZ
C           TEMPCO=3        X AXIS DIRECTION IN THE ORIGINAL STATE
C                 =2        Y
C                 =1        Z       DIRECTION
            GO TO (13,12,11) TEMPCO
11          WX1=SX
            WX2=0
              WZ1=0
```

```
              WZ2=SZ
                WY1=SY/2
                WY2=SY/2
          KX1=SX
          KX2=0
             KY1=0
             KY2=SY
               KZ1=SZ/2
               KZ2=SZ/2
               GO TO 14
12        WY1=SY
          WY2=0
             WZ1=0
             WZ2=SZ
                WX1=SX/2
                WX2=SX/2
          KY1=SY
          KY2=0
             KX1=0
             KX2=SX
               KZ1=SZ/2
               KZ2=SZ/2
               GO TO 14
13        WZ1=SZ
          WZ2=0
             WX1=0
             WX2=SX
                WY1=SY/2
                WY2=SY/2
                   KZ1=SZ
          KZ2=0
             KY1=0
             KY2=SY
               KX1=SX/2
               KX2=SX/2
14        N1=VECTOR(WX1,WY1,WZ1)
              N2=VECTOR(WX2,WY2,WZ2)
          VECT1(I,J,2)=N1
          VECT2(I,J,2)=N2
          M1=VECTOR(KX1,KY1,KZ1)
          M2=VECTOR(KX2,KY2,KZ2)
          VECT1(I,J,3)=M1
          VECT2(I,J,3)=M2
          VECT1(I,J,4)=N2
          VECT2(I,J,4)=N1
          VECT1(I,J,5)=M2
          VECT2(I,J,5)=M1
          GO TO 7
C                                    CONFORMATION R2=16
5         SX=WX+NX
          SY=WY+NY
          SZ=WZ+NZ
          TEMPCO=(3*IABS(SX)+2*IABS(SY)+IABS(SZ))/4
          GO TO (23,22,21) TEMPCO
21        WX1=WX
          WX2=NX
             WY1=WZ
             WY2=NZ
                    WZ1=WY
                WZ2=NY
          KX1=WX
          KX2=NX
             KY1=NZ
             KY2=WZ
               KZ1=NY
               KZ2=WY
               GO TO 24
22        WY1=WY
          WY2=NY
             WX1=WZ
             WX2=NZ
                WZ1=WX
```

```
              WZ2=NX
          KY1=WY
          KY2=NY
             KX1=NZ
             KX2=WZ
                KZ1=NX
                KZ2=WX
                  GO TO 24
23        WZ1=WZ
          WZ2=NZ
             WX1=WY
             WX2=NY
                WY1=WX
                WY2=NX
          KZ1=WZ
          KZ2=NZ
             KX1=NY
             KX2=WY
                KY1=NX
                KY2=WX
24        N1=VECTOR(WX1,WY1,WZ1)
             N2=VECTOR(WX2,WY2,WZ2)
          VECT1(I,J,2)=N1
          VECT2(I,J,2)=N2
          VECT1(I,J,4)=N2
          VECT2(I,J,4)=N1
          M1=VECTOR(KX1,KY1,KZ1)
          M2=VECTOR(KX2,KY2,KZ2)
          VECT1(I,J,3)=M1
          VECT2(I,J,3)=M2
          VECT1(I,J,5)=M2
          VECT2(I,J,5)=M1
7         CONTINUE
C                        CONFORMATION IS NOT ACCETABLE
          ELSE
               DO K=1,5
               VECT1(I,J,K)=0
               VECT2(I,J,K)=0
               ENDDO
               END IF
      ENDDO
      ENDDO
C
C
C     ..............................................................
C
C     SIDE GROUPS - EXPLICITE DEFINITION BASED ON CONFORMATION   R2
C
C     ..............................................................
C
C                SIDGR1(24,24)   -  CONTAINS CODES OF 110 VECTORS
C                SIDGR2(24,24)   -  CONTAINS CODES OF 110 VECTORS
C                SIDGR3(24,24)   -  CONTAINS CODES OF 110 VECTORS
C
      DO I=1,24
      DO J=1,24
          IF(.NOT.GOODC(I,J)) GO TO 40
          X1=VX(I)
          Y1=VY(I)
          Z1=VZ(I)
          X2=VX(J)
          Y2=VY(J)
          Z2=VZ(J)
          ICONA=(ICONF(I,J)-4)/2
          PX=Y1*Z2-Y2*Z1
          PY=X2*Z1-Z2*X1
          PZ=X1*Y2-Y1*X2

PX=-PX
                  PY=-PY
                  PZ=-PZ

WX=X1-X2
             WY=Y1-Y2
```

```
              WZ=Z1-Z2
        GO TO (33,32,33,32,31,32,36) ICONA
C                                   CONFORMATION R2=14
  31  SUMAX=PX
      SUMAY=PY
      SUMAZ=PZ
                GO TO 39
C                                   CONFORMATION R2=8
C                                   CONFORMATION R2=12
C                                   CONFORMATION R2=16
  32    SUMAX=PX-2*X2
        SUMAY=PY-2*Y2
        SUMAZ=PZ-2*Z2
        GO TO 39
C                                   CONFORMATION R2=6
C                                       CONFORMATION R2=10
C
  33  SUMAX=PX+WX
      SUMAY=PY+WY
      SUMAZ=PZ+WZ
      GO TO 39
C                                   CONFORMATION R2=18
C
  36     IF(PX*PY.NE.0) THEN
C                              THE CASE OF DOWN THE AXIS CONFORMATION
      SUMAX=PX
      SUMAY=PY
      SUMAZ=PZ
          GO TO 39
         ENDIF
C                                   THE CASE OF 330 CONFORMATION

SUMAX=PX+WX
      SUMAY=PY+WY
      SUMAZ=PZ+WZ
C
C
  39  SUX=ISIGN(1,SUMAX)
      SUY=ISIGN(1,SUMAY)
      SUZ=ISIGN(1,SUMAZ)
          X1=SUX
          X2=SUX
          X3=0
              Y1=SUY
              Y2=0
              Y3=SUY
                  Z1=0
                  Z2=SUZ
                  Z3=SUZ
C
C              GIVES THE CODE OF (STLX,STLY,STLZ)V, VALUE 1,2,..12
        ICODT=9*X1+3*Y1+Z1
        IF(ICODT.LT.0) ICODT=-1-ICODT
        SIDGR1(I,J)=ICODT
        ICODT=9*X2+3*Y2+Z2
        IF(ICODT.LT.0) ICODT=-1-ICODT
        SIDGR2(I,J)=ICODT
        ICODT=9*X3+3*Y3+Z3
        IF(ICODT.LT.0) ICODT=-1-ICODT
        SIDGR3(I,J)=ICODT
c    insert of check for handedness
      x4=(x1+x2+x3)/2
      y4=(y1+y2+y3)/2
      z4=(z1+z2+z3)/2
      S1X(i,j)=x4
      S1Y(i,j)=y4
      S1Z(i,j)=z4

40  CONTINUE
      ENDDO
      ENDDO
```

```
c      INPUT    INPUT    INPUT    INPUT    INPUT    INPUT    INPUT    INPUT    INPUT
c      ----------------------------------------------------------------
c           SET UP OF THE VECTOR REPRESENTATION OF THE CHAIN
c
       OPEN(UNIT=5,FILE='INPUT',STATUS='OLD')
       OPEN(UNIT=10,FILE='FILEDAT',STATUS='OLD')
       OPEN(UNIT=6,FILE='OUTPUT',STATUS='OLD')
       OPEN(UNIT=1,FILE='SEQUENCE',STATUS='OLD')
       OPEN(UNIT=11,FILE='contact',STATUS='OLD')
       OPEN(UNIT=12,FILE='PHISEQH',STATUS='OLD')
       OPEN(UNIT=14,FILE='PHISEQHR',STATUS='OLD')
       OPEN(UNIT=13,FILE='TRACE',STATUS='OLD')

c
       READ(10,*) LENF
       LENF1=LENF-1
       LENF2=LENF-2
       AL2=LENF2
       LENF3=LENF-3
       AL3=LENF3
       LENF4=LENF-4
       AL4=LENF4
       AL6=LENF-6
       AL9=LENF-9
       MIX=1
       LENHA=LENF/2 do i=1,100
          STATN(i)=0.d0
       IDIS(i)=0.d0
          ASTR(i)=0.d0
       IHAND(i)=0.d0
          RSTATN(i)=0.d0
       RIDIS(i)=0.d0
          astrr(i)=0.d0
       RIHAND(i)=0.d0
       do j=1,100
       do k=1,100 xyz(k,j,i)=0.d0
       end do
       end do
       end do c
c      ******************SEQUENCE READING**********************
c c      *************READING OF TORSIONAL POTENTIALS*************
c
c      EXPLICIT CONSTRUCTION OF  APH
       DO LJ=2,LENF1
       READ(12,*)K,STATN(LJ),IDIS(LJ),ASTR(LJ),IHAND(LJ)
       END DO
c      generalized to include other conformational prefrences
       read(14,*)other
       do lj=1,other
       READ(14,*)K,RSTATN(k),RIDIS(k),ASTRR(k),RIHAND(k)
       END DO c      ******************SEQUENCE READING**********************
c
c
c      CAUTION::: THE REVERSE PATTERN IS NOT ALLOWED +K HAS TO BE
c                 ASSUMED AS A PREFERENCE FOR A GIVEN STATE
c
c
c      STATN - R2(I-1,I+1)
c      IDIS  - R2(I-1,I+2)
```

```
C     ASTR- STRENGTH OF PREFERENCE FOR THE DIHEDRAL ANGLE
C
C     ah plays the role of the thermalization factor
      read(5,*)ah
      WRITE(6,8120)
8120  FORMAT(1X,'  ** THE THREE SIDE GROUP PROGRAM
     *     AND GLI ncglyshortREP.f with picture every iterm steps**',/,
     *          'uses not necessarily native conf in torsions',/)

NBGL=0
      INDGL(1)=0
      INDGL(LENF)=0
      DO I=2,LENF1
      INDGL(I)=1
      READ(1,*) K,IC6(I),
     *    IC8(I),IC10(I),IC12(I),IC14(I),IC16(I),IC18(I),IHYD(I)
      IF(IHYD(I).EQ.0) THEN
           INDGL(I)=0
           NBGL=NBGL+1
           ENDIF
      ENDDO
C
C     *******************INPUT FILE***************************
C
      READ(5,*) RANDOM,NCYCLE, PHOT
      READ(5,*) AC6,AC8,AC10,AC12,AC14,AC16,AC18
      READ(5,*) APLPB,BPLPL,CPBPB,AREP,AHB,APHI
      READ(5,*) ATEMP,WAVEL
C
      WRITE(6,8020) RANDOM,NCYCLE,PHOT,WAVEL

8020    FORMAT(1X,'  ** THE THREE SIDE GROUP PROGRAM  AND GLI.**',/,
     *          'DIAMOND LATTICE SITES INTERACT ',/,
     *          '**           JSDIA.F        **',/,
     *    1X,' RANDOM SEED =',I6,'   NUMBER OF CYCLES',2I5,/,
     *    1X, ' MAXIMUM WAVE LENGTH =',I4,/ )
      write(6,8999)ah
8999    format(1x,' temp/tempthermal =',1f8.4)
      WRITE(6,8021) AC6,AC8,AC10,AC12,AC14,AC16,AC18
 8021    FORMAT(5X,/,3X,' ENERGY OF STATE  6 =',F6.2,/,
     *    3X,' ENERGY OF STATE  8 =',F6.2,/,
     *    3X,' ENERGY OF STATE 10=',F6.2,/,
     *    3X,' ENERGY OF STATE 12=',F6.2,/,
     *    3X,' ENERGY OF STATE 14=',F6.2,/,
     *    3X,' ENERGY OF STATE 16=',F6.2,/,
     *    3X,' ENERGY OF STATE 18=',F6.2,/)
      WRITE(6,8022) APLPB,BPLPL,CPBPB
 8022    FORMAT(3X,' PHIL-PHOB, PHIL-PHIL, PHOB-PHOB   ',4F8.3,/)
      WRITE(6,8024) AREP,AHB,APHI
 8024    FORMAT(3X,' REPULSIVE INT. AND  COOPER.+H-BOND',2F8.3,/
     *      ,3X,' SCALING FACTOR FOR DIHEDRAL ANGLE POTENTIAL',F8.3,/)
      WRITE(6,8023) ATEMP
 8023    FORMAT(1X,/,3X,' TEMPERATURE OF THE SYSTEM =',F8.3,/)
C
C     construction of native contact map
      do i=1,lenf2
      do j=i,lenf1
      inc(i,j)=0.d0
      inc(j,i)=0.d0
      end do
      end do read(11,*)ntot
      write(6,2039)ntot
2039  format(1x,'not=',i3,/,'the native contact pairs are' )
      do i=1,ntot
      read(11,*)j,k
      inc(j,k)=1
      write(6,*)j,k
      end do
```

```
C
C    **********  SET THE CURRENT FORCE OF INTERACTIONS  **********
C
     APHI=APHI/ATEMP
     AHB=AHB/ATEMP
     AC6=AC6/ATEMP
     AC8=AC8/ATEMP
     AC10=AC10/ATEMP
     AC12=AC12/ATEMP
     AC14=AC14/ATEMP
     AC16=AC16/ATEMP
     AC18=AC18/ATEMP
     APLPB=APLPB/ATEMP
     BPLPL=BPLPL/ATEMP
     CPBPB=CPBPB/ATEMP
     AREP=AREP/ATEMP
          DO I=2,LENF1
          DO J=2,LENF1
          IF(IABS(I-J).GT.2) THEN

CROSS=FLOAT(IHYD(I)*IHYD(J))
          AM(I,J)=-CROSS*APLPB
          IF(IHYD(I).GT.0.AND.IHYD(J).GT.0) AM(I,J)=CROSS*BPLPL
          IF(IHYD(I).LT.0.AND.IHYD(J).LT.0) AM(I,J)=CROSS*CPBPB
          ELSE
          AM(I,J)=0.
C         A PRIORI NO INTERACTIONS OF SIDE GROUPS WHEN/I-J/<3
          ENDIF
          ENDDO
          ENDDO
C
          DO I=2,LENF1
          AC(I,6)=IC6(I)*AC6
          AC(I,8)=IC8(I)*AC8
          AC(I,10)=IC10(I)*AC10
          AC(I,12)=IC12(I)*AC12
          AC(I,14)=IC14(I)*AC14
          AC(I,16)=IC16(I)*AC16
          AC(I,18)=IC18(I)*AC18
          ENDDO

C
C    ***************READING OF TORSIONAL POTENTIALS***************
C
     DO 100 I=1,24
          X1=VX(I)
          Y1=VY(I)
          Z1=VZ(I)
     DO 1200 J=1,24
     IF(GOODC(I,J)) THEN
          X2=VX(J)
          Y2=VY(J)
          Z2=VZ(J)
C              CROSS PRODUCT OF THE TWO FIRST VECTORS
          PX=Y1*Z2-Y2*Z1
          PY=Z1*X2-Z2*X1
          PZ=X1*Y2-Y1*X2
     st1=iconf(i,j)
     DO 300 K=1,24
     IF(.NOT.GOODC(J,K)) GO TO 300
          X3=VX(K)
          Y3=VY(K)
          Z3=VZ(K)
          IHAN=PX*X3+PY*Y3+PZ*Z3
     IHAN=SIGN(1,IHAN)
     st2=iconf(j,k)
C..............................................................
C
     DO 401 INDEX=2,LENF2
```

```
      B=0.
      aph(i,j,k,index)=0.
      IF(STATN(INDEX).EQ.ST1.AND.STATN(INDEX+1).EQ.ST2) THEN
              KX=X1+X2+X3
              KY=Y1+Y2+Y3
              KZ=Z1+Z2+Z3
              R2=KX*KX+KY*KY+KZ*KZ
      IF(R2.EQ.IDIS(INDEX).and. ihan .eq. ihand(index))B=ASTR(INDEX)
              ENDIF
      APH(I,J,K,INDEX)=(B)*APHI
      IF(RSTATN(INDEX).EQ.ST1.AND.RSTATN(INDEX+1).EQ.ST2) THEN
              KX=X1+X2+X3
              KY=Y1+Y2+Y3
              KZ=Z1+Z2+Z3
              R2=KX*KX+KY*KY+KZ*KZ
      IF(R2.EQ.RIDIS(INDEX).and.ihan.eq.Rihand(index))B=astrR(INDEX)
              ENDIF
      APH(I,J,K,INDEX)=(B)*APHI
 401  CONTINUE
C............................................................
C
 300  CONTINUE
          END IF
 1200     CONTINUE
 100  CONTINUE ICA(0)=1
C     this is because the simplicity of APH reading, value irrelevant
      ICA(LENF)=1
C
C     ******************INITIAL CONFORMATION*********************
C
C
C
C             caution (zero initialization assumed)
      MAX=100
      MID=MAX/2
      SX=0
      SY=0
      SZ=0
      DO I=1,LENF
      READ(10,*) X(I),Y(I),Z(I)
      SX=SX+X(I)
      SY=SY+Y(I)
      SZ=SZ+Z(I)
      ENDDO
          SX=SX/LENF
          SY=SY/LENF
          SZ=SZ/LENF
          XSHIFT=MID-SX
          YSHIFT=MID-SY
          ZSHIFT=MID-SZ
      DO I=1,LENF
      X(I)=X(I)+XSHIFT
      Y(I)=Y(I)+YSHIFT
      Z(I)=Z(I)+ZSHIFT
      ENDDO
          DO I=1,LENF1
          J=I+1
          WX=X(J)-X(I)
          WY=Y(J)-Y(I)
          WZ=Z(J)-Z(I)
          ICA(I)=VECTOR(WX,WY,WZ)
          ENDDO
      CALL setin(XYZ,INDGL(1),X(1),Y(1),Z(1),13,13,13,1)
      CALL setin(XYZ,INDGL(LENF),X(LENF),Y(LENF),Z(LENF),13,13,13,1)
      DO J=2,LENF1
      I=J-1
      II=ICA(I)
      JJ=ICA(J)
      IF(GOODC(II,JJ)) THEN
          S1=SIDGR1(II,JJ)
          S2=SIDGR2(II,JJ)
```

```
              S3=SIDGR3(II,JJ)
              CALL setin(XYZ,INDGL(J),X(J),Y(J),Z(J),S1,S2,S3,J)
              ELSE
              WRITE(6,8001) I,J
 8001             FORMAT(5X,'WRONG INPUT CHAIN - VECTORS ',2I4)
              GO TO 9000
              END IF
          ENDDO
C
C........CALCULATION OF THE ENERGY OF INITIAL STATE
C
      E=0.
      ENERG=0.
      DO J=2,LENF1
      I=J-1
      II=ICA(I)
      JJ=ICA(J)
C                        ROTATIONAL CONTRIBUTION
      JCONF=ICONF(II,JJ)
      ENERG=ENERG+AC(J,JCONF)
C                        INTERACTIONS OF SIDE GROUPS IX=X(J)+S1X(ii,jj)
          IY=Y(J)+S1Y(ii,jj)
          IZ=Z(J)+S1Z(ii,jj)
          E=E+ERG(XYZ,INDGL(J),AM,IX,IY,IZ,J)
 4501 continue
      ENDDO
      ENERG=ENERG+E/2.
C                        COOPERATIVE AND HYDROGEN BOND
      E=0.
      DO I=2,LENF1
      E=E+EHB(XYZ,ICA,PRODV,X(I),Y(I),Z(I),I,AHB)
      ENDDO
      ENERG=ENERG+E/2

C                        REPULSIVE INTERACTIONS
      E=0.
      DO I=2,LENF1
      E=E+EREPUL(XYZ,X(I),Y(I),Z(I),1.)
      ENDDO
C     this is because the implicite symmetry of repulsive interactions
C     which is taken into account in the remainder of the program.

E=(E-AL3*2.)/2.
      ENERG=ENERG+E*AREP
C
C                        DIHEDRAL POTENTIAL
      DO J=2,LENF2
      II=ICA(J-1)
      JJ=ICA(J)
      KK=ICA(J+1)
      ENERG=ENERG+APH(II,JJ,KK,J)
      ENDDO

C/////////////////////////////////////////////////
      RN1=RANDOM*2+7531
      RN2=RANDOM*2+8883
      RN3=RANDOM*6+7907

C     ****************************************************************
C     *                                                              *
C     *                DYNAMICS OF THE CHAIN                         *
C     *                                                              *
C     ****************************************************************
C
C
C     MAIN CLOCK OF THE ALGORITHM
C
      ICLOCK=1
```

```
c
      QROT=0
      QWAVE=0
      QKINK=0
      QEND=0
c
      asumr2=0.
      asums2=0.
      etot=0.d0
      etot2=0.d0
      sxd=0.d0
      syd=0.d0
      szd=0.d0 anct=0.d0
      ant=0.d0
      write(6,931)
931     format(1x,'iterm=  R2=   AS2=   ENERGY=    native  any contacts')

DO 7777   ITERM=1,NCYCLE
                  iclock=iclock+1
c
      DO 7700 IDUMI=1,100
                  iclock=iclock+1
c
      DO 7770 IPHCO=1,PHOT
c
      IF(ICLOCK.GT.2000) ICLOCK=ICLOCK-vaxran(rn2)*1000
c
c ............LATERAL WAVE DISPLACEMENT........................
c
c     set up of the thermalization move
      if(vaxran(rn2) .gt. .01) then
            af=1.d0
      else
            af=ah
      end if
      IVA=MOD(ICLOCK,WAVEL)+3
      I=INT(vaxran(rn1)*AL6)+3
      IF(I.GT.LENH.) THEN
            IFIRST=I-IVA
            ILAST=I
            ELSE
            IFIRST=I
            ILAST=I+IVA
            ENDIF
      WI=ICA(IFIRST)
      JL=ILAST-1
      WJ=ICA(JL)
      JCONF=ICONF(WI,WJ)
      IF(JCONF.LT.14.OR.JCONF.GT.18) GO TO 7001
      IF(.NOT.GOODC(ICA(IFIRST-1),WJ)) GO TO 7001
      IF(.NOT.GOODC(WJ,ICA(IFIRST+1))) GO TO 7001
      IF(.NOT.GOODC(ICA(ILAST-2),WI)) GO TO 7001
      IF(.NOT.GOODC(WI,ICA(ILAST))) GO TO 7001 c                       REMOVE THE STRING
      DO K=IFIRST,ILAST
      II=ICA(K-1)
      KK=ICA(K)
      IKS1=SIDGR1(II,KK)
      IKS2=SIDGR2(II,KK)
      IKS3=SIDGR3(II,KK)
      XJ=X(K)
      YJ=Y(K)
      ZJ=Z(K)
      CALL REMOVE(XYZ,INDGL(K),XJ,YJ,ZJ,IKS1,IKS2,IKS3)
      ENDDO
c                       SETIN AND EXCLUDED
```

```
C                         VOLUME TEST
C                    THE NEW VECTORS
                     ICA(IFIRST)=WJ
                     ICA(JL)=WI

IFA=IFIRST-1
           XJ=X(IFA)
           YJ=Y(IFA)
           ZJ=Z(IFA)
      DO J=IFIRST,ILAST
      II=ICA(J-1)

JJJ=ICA(J)
           XJ=XJ+VX(II)
           YJ=YJ+VY(II)
           ZJ=ZJ+VZ(II)
           XNEW(J)=XJ
           YNEW(J)=YJ
           ZNEW(J)=ZJ
           S1=SIDGR1(II,JJJ)
           S2=SIDGR2(II,JJJ)
           S3=SIDGR3(II,JJJ)
           IF(LOOK(XYZ,INDGL(J),XJ,YJ,ZJ,S1,S2,S3)) THEN
C                              THEN REMOVE AND TERMINATE
               IF(J.EQ.IFIRST) GO TO 2004
               DO K=IFIRST,J-1
               KK=ICA(K-1)
               KKK=ICA(K)
           S1=SIDGR1(KK,KKK)
           S2=SIDGR2(KK,KKK)
           S3=SIDGR3(KK,KKK)
           CALL REMOVE(XYZ,INDGL(K),XNEW(K),YNEW(K),ZNEW(K),S1,S2,S3)
               ENDDO
 2004                 ICA(IFIRST)=WI
                     ICA(JL)=WJ

DO I=IFIRST,ILAST
               II=ICA(I-1)
               JJJ=ICA(I)

S1=SIDGR1(II,JJJ)
           S2=SIDGR2(II,JJJ)
           S3=SIDGR3(II,JJJ)

CALL setin(XYZ,INDGL(I),X(I),Y(I),Z(I),S1,S2,S3,I)
               ENDDO
               GO TO 7001
               ELSE
C                                   SET NEW BEAD
           CALL setin(XYZ,INDGL(J),XJ,YJ,ZJ,S1,S2,S3,J)
               ENDIF
      ENDDO
C                 THE NEW STRING KEEPS EXCLUDED VOLUME
C
C
C
C     COMPUTATION OF ENERGY OF THE NEW CONFORMATION AND REMOVE STRING
C ENEW=0.
      ER=0.
      E=0.
      DO J=IFIRST,ILAST
      I=J-1
      II=ICA(I)
      JJ=ICA(J)
           XJ=XNEW(J)
           YJ=YNEW(J)
           ZJ=ZNEW(J)
           S1=SIDGR1(II,JJ)
           S2=SIDGR2(II,JJ)
           S3=SIDGR3(II,JJ)
      JCONF=ICONF(II,JJ)
      ENEW=ENEW+AC(J,JCONF)+APH(II,JJ,ICA(J+1),J)
```

```
c                       INTERACTIONS OF SIDE GROUPS
        IX=XJ+S1X(ii,jj)
        IY=YJ+S1y(ii,jj)
        IZ=ZJ+S1z(ii,jj)
        E=E+ERG(XYZ,INDGL(J),AM,IX,IY,IZ,J)

c                       COOPERATIVE AND HYDROGEN BOND
    E=E+EHB(XYZ,ICA,PRODV,XJ,YJ,ZJ,J,AHB)
c                       REPULSIVE INTERACTIONS
    ER=ER+EREPUL(XYZ,XJ,YJ,ZJ,AREP)
        CALL REMOVE(XYZ,INDGL(J),XJ,YJ,ZJ,S1,S2,S3)
    ENDDO
    ENEW=ENEW+APH(ICA(IFIRST-2),ICA(IFA),ICA(IFIRST),IFA)
    ENEW=ENEW+E+ER
c
c
c
c   COMPUTATION OF THE OLD ENERGY AND   SETIN OF THE CHAIN PIECE
c c       THE OLD VECTORS
        ICA(IFIRST)=WI
        ICA(JL)=WJ
    EOLD=0.
    ER=0.
    E=0.
    DO J=IFIRST,ILAST
    XJ=X(J)
    YJ=Y(J)
    ZJ=Z(J)
    II=ICA(J-1)
    JJJ=ICA(J)
        S1=sIDGR1(II,JJJ)
        S2=SIDGR2(II,JJJ)
        S3=SIDGR3(II,JJJ)
c       s4=sidgr4(ii,jjj)
c   tx=tlx(s4)
c   ty=tly(s4)
c   tz=tlz(s4)
        CALL setin(XYZ,INDGL(J),XJ,YJ,ZJ,S1,S2,S3,J)
c
    JCONF=ICONF(II,JJJ)
    EOLD=EOLD+AC(J,JCONF)+APH(II,JJJ,ICA(J+1),J)
c                       INTERACTIONS OF SIDE GROUPS IX=XJ+S1x(ii,jjj)
        IY=YJ+S1y(ii,jjj)
        IZ=ZJ+S1z(ii,jjj)
        E=E+ERG(XYZ,INDGL(J),AM,IX,IY,IZ,J)

c                       COOPERATIVE AND HYDROGEN BOND
    E=E+EHB(XYZ,ICA,PRODV,XJ,YJ,ZJ,J,AHB)
c                       REPULSIVE INTERACTIONS
    ER=ER+EREPUL(XYZ,XJ,YJ,ZJ,AREP)
    ENDDO
    EOLD=EOLD+APH(ICA(IFIRST-2),ICA(IFA),ICA(IFIRST),IFA)
    EOLD=EOLD+E+ER c
c   METROPOLIS CRITERION
c
    DE=ENEW-EOLD
    IF(EXP(-DE*af).GT.vaxran(rn3)) THEN
c                                       ACCEPTED
        QROT=QROT+1
        ENERG=ENERG+DE
            DO J=IFIRST, ILAST
            II=ICA(J-1)
            JJ=ICA(J)
        S1=SIDGR1(II,JJ)
        S2=SIDGR2(II,JJ)
        S3=SIDGR3(II,JJ)
```

```
              CALL REMOVE(XYZ,INDGL(J),X(J),Y(J),Z(J),S1,S2,S3)
              ENDDO
C                 THE NEW VECTORS
                  ICA(IFIRST)=WJ
                  ICA(JL)=WI
         DO J=IFIRST,ILAST
         XJ=XNEW(J)
         YJ=YNEW(J)
         ZJ=ZNEW(J)
         X(J)=XJ
         Y(J)=YJ
         Z(J)=ZJ
         II=ICA(J-1)
         JJ=ICA(J)
         S1=SIDGR1(II,JJ)
         S2=SIDGR2(II,JJ)
         S3=SIDGR3(II,JJ)
         CALL setin(XYZ,INDGL(J),XJ,YJ,ZJ,S1,S2,S3,J)
         ENDDO
      ENDIF 7001     DO 7000 IDUMA=1,LENF4
      ICLOCK=ICLOCK+1
C
      I=INT(vaxran(rn1)*AL4)+2
C        RUNS FROM 2 TO LENF-3 (VECTOR INDEX  RUNS FROM 1 TO LENF-1)
      J=I+1
      KINK=MOD(ICLOCK,5)+1
C        DEFINES KIND OF KINK OF THE  VECTORS I-J
      IV=ICA(I)
      JV=ICA(J)
      IIV=VECT1(IV,JV,KINK)
      IP=I-1
      IPV=ICA(IP)
      IF(.NOT.GOODC(IPV,IIV)) GO TO 7000
      JN=J+1
      JNV=ICA(JN)
      JJV=VECT2(IV,JV,KINK)
      IF(.NOT.GOODC(JJV,JNV)) GO TO 7000
C
C        CONFORMATION IS OK   - CHECK THE EXCLUDE VOLUME C                         REMOVE THE STRING
      JL=J
      ifirst=i
      ilast=jn
      DO K=IFIRST,ILAST
      II=ICA(K-1)
      KK=ICA(K)
      IKS1=SIDGR1(II,KK)
      IKS2=SIDGR2(II,KK)
      IKS3=SIDGR3(II,KK)
      XJ=X(K)
      YJ=Y(K)
      ZJ=Z(K)
      CALL REMOVE(XYZ,INDGL(K),XJ,YJ,ZJ,IKS1,IKS2,IKS3)
      ENDDO
C                      SETIN AND EXCLUDED
C                      VOLUME TEST
C             THE NEW VECTORS
              ICA(IFIRST)=iiv
              ICA(JL)=jjv
         IFA=IFIRST-1
         XJ=X(IFA)
         YJ=Y(IFA)
         ZJ=Z(IFA)
      DO J=IFIRST,ILAST
      II=ICA(J-1)
      JJJ=ICA(J)
         XJ=XJ+VX(II)
         YJ=YJ+VY(II)
```

```
              ZJ=ZJ+VZ(II)
              XNEW(J)=XJ
              YNEW(J)=YJ
              ZNEW(J)=ZJ
              S1=SIDGR1(II,JJJ)
              S2=SIDGR2(II,JJJ)
              S3=SIDGR3(II,JJJ)
              IF(LOOK(XYZ,INDGL(J),XJ,YJ,ZJ,S1,S2,S3)) THEN
c                             THEN REMOVE AND TERMINATE
              IF(J.EQ.IFIRST) GO TO 2204
              DO K=IFIRST,J-1
              KK=ICA(K-1)
              KKK=ICA(K)
              S1=SIDGR1(KK,KKK)
              S2=SIDGR2(KK,KKK)
              S3=SIDGR3(KK,KKK)
              CALL REMOVE(XYZ,INDGL(K),XNEW(K),YNEW(K),ZNEW(K),S1,S2,S3)
              ENDDO
2204                    ICA(IFIRST)=IV
                   ICA(JL)=JV

DO I=IFIRST,ILAST
              II=ICA(I-1)
              JJJ=ICA(I)

S1=SIDGR1(II,JJJ)
              S2=SIDGR2(II,JJJ)
              S3=SIDGR3(II,JJJ)

CALL setin(XYZ,INDGL(I),X(I),Y(I),Z(I),S1,S2,S3,I)
              ENDDO
                  GO TO 7000
                  ELSE
c                                  SET NEW BEAD
              CALL setin(XYZ,INDGL(J),XJ,YJ,ZJ,S1,S2,S3,J)
                  ENDIF
       ENDDO
c            THE NEW STRING KEEPS EXCLUDED VOLUME
c
c
c
c      COMPUTATION OF ENERGY OF THE NEW CONFORMATION AND REMOVE STRING
c
       ENEW=0.
       ER=0.
       E=0.
       DO J=IFIRST,ILAST
       I=J-1
       II=ICA(I)
       JJ=ICA(J)
              XJ=XNEW(J)
              YJ=YNEW(J)
              ZJ=ZNEW(J)
              S1=SIDGR1(II,JJ)
              S2=SIDGR2(II,JJ)
              S3=SIDGR3(II,JJ)

c                       ROTATIONAL CONTRIBUTION
       JCONF=ICONF(II,JJ)
       ENEW=ENEW+AC(J,JCONF)+APH(II,JJ,ICA(J+1),J)
c                       INTERACTIONS OF SIDE GROUPS
              IX=XJ+S1x(ii,jj)
              IY=YJ+S1Y(ii,jj)
              IZ=ZJ+S1z(ii,jj)
              E=E+ERG(XYZ,INDGL(J),AM,IX,IY,IZ,J)

c                       COOPERATIVE AND HYDROGEN BOND
       E=E+EHB(XYZ,ICA,PRODV,XJ,YJ,ZJ,J,AHB)
c                       REPULSIVE INTERACTIONS
       ER=ER+EREPUL(XYZ,XJ,YJ,ZJ,AREP)
              CALL REMOVE(XYZ,INDGL(J),XJ,YJ,ZJ,S1,S2,S3)
       ENDDO
       ENEW=ENEW+APH(ICA(IFIRST-2),ICA(IFA),ICA(IFIRST),IFA)
```

```
      ENEW=ENEW+E+ER
c
c
c
c     COMPUTATION OF THE OLD ENERGY AND SETIN OF THE CHAIN PIECE
c c          THE OLD VECTORS
           ICA(IFIRST)=IV
           ICA(JL)=JV
      EOLD=0.
      ER=0.
      E=0.
      DO J=IFIRST,ILAST
      XJ=X(J)
      YJ=Y(J)
      ZJ=Z(J)
      II=ICA(J-1)
      JJJ=ICA(J)
           S1=SIDGR1(II,JJJ)
           S2=SIDGR2(II,JJJ)
           S3=SIDGR3(II,JJJ)
c          s4=sidgr4(ii,jjj)
c     tx=tlx(s4)
c     ty=tly(s4)
c     tz=tlz(s4)
           CALL setin(XYZ,INDGL(J),XJ,YJ,ZJ,S1,S2,S3,J)
c
      JCONF=ICONF(II,JJJ)
      EOLD=EOLD+AC(J,JCONF)+APH(II,JJJ,ICA(J+1),J)
c                          INTERACTIONS OF SIDE GROUPS IX=XJ+S1x(ii,jjj)
           IY=YJ+S1Y(ii,jjj)
           IZ=ZJ+S1z(ii,jjj)
           E=E+ERG(XYZ,INDGL(J),AM,IX,IY,IZ,J)

c                          COOPERATIVE AND HYDROGEN BOND
      E=E+EHB(XYZ,ICA,PRODV,XJ,YJ,ZJ,J,AHB)
c                          REPULSIVE INTERACTIONS
      ER=ER+EREPUL(XYZ,XJ,YJ,ZJ,AREP)
      ENDDO
      EOLD=EOLD+APh(ICA(IFIRST-2),ICA(IFA),ICA(IFIRST),IFA)
      EOLD=EOLD+E+ER c
c     METROPOLIS CRITERION
c
      DE=ENEW-EOLD
      IF(EXP(-DE).GT.vaxran(rn3)) THEN
c                                 ACCEPTED
           iflip(iconf(iv,jv),kink)=iflip(iconf(iv,jv),kink)+1
           QKINK=QKINK+1
           ENERG=ENERG+DE
               DO J=IFIRST, ILAST
               II=ICA(J-1)
               JJ=ICA(J)
           S1=SIDGR1(II,JJ)
           S2=SIDGR2(II,JJ)
           S3=SIDGR3(II,JJ)

CALL REMOVE(XYZ,INDGL(J),X(J),Y(J),Z(J),S1,S2,S3)
           ENDDO
c               THE NEW VECTORS
                ICA(IFIRST)=IIV
                ICA(JL)=JJV
      DO J=IFIRST,ILAST
      XJ=XNEW(J)
      YJ=YNEW(J)
      ZJ=ZNEW(J)
      X(J)=XJ
      Y(J)=YJ
```

```fortran
              Z(J)=ZJ
              II=ICA(J-1)
              JJ=ICA(J)
              S1=SIDGR1(II,JJ)
              S2=SIDGR2(II,JJ)
              S3=SIDGR3(II,JJ)
              CALL setin(XYZ,INDGL(J),XJ,YJ,ZJ,S1,S2,S3,J)
          ENDDO
      ENDIF
c
 7000     CONTINUE
c     idummy=1
c     if(idummy .eq. 1) go to 7770
c
c                         END FLIPS (TWO BONDS REARANGEMENTS)
c
c         N-TERMINUS (TAIL)
c
      JV3=ICA(3)
 60   NV2=INT(vaxran(rn1)*24.)+1
      IF(.NOT.GOODC(NV2,JV3)) GO TO 60
 61   NV1=INT(vaxran(rn3)*24.)+1
      IF(.NOT.GOODC(NV1,NV2)) GO TO 61
c         CONFORMATION IS OK.  CHECK  THE EXCLUDED VOLUME
      CALL REMOVE(XYZ,INDGL(1),X(1),Y(1),Z(1),13,13,13)
      ICA1=ICA(1)
      ICA2=ICA(2)
      PK21=SIDGR1(ICA1,ICA2)
      PK22=SIDGR2(ICA1,ICA2)
      PK23=SIDGR3(ICA1,ICA2)

c     **************************
      CALL REMOVE(XYZ,INDGL(2),X(2),Y(2),Z(2),PK21,PK22,PK23)
c         CHECK THE ROTATION OF SIDE GROUP ON THIRD BEAD
c         8/19/89
c     oninvoke if no glycines are here
c
      if(indgl(3) .eq.0) go to 3040
      PK31=SIDGR1(ICA2,JV3)
      PK32=SIDGR2(ICA2,JV3)
      PK33=SIDGR3(ICA2,JV3)
c     ****************************************************
c     **************************

SX1=X(3)+STLX(PK31)
      SX2=X(3)+STLX(PK32)
      SX3=X(3)+STLX(PK33)
      SY1=Y(3)+STLY(PK31)
      SY2=Y(3)+STLY(PK32)
      SY3=Y(3)+STLY(PK33)
      SZ1=Z(3)+STLZ(PK31)
      SZ2=Z(3)+STLZ(PK32)
      SZ3=Z(3)+STLZ(PK33)
      XYZ(SX1,SY1,SZ1)=0
      XYZ(SX2,SY2,SZ2)=0
      XYZ(SX3,SY3,SZ3)=0
              xone=(sx1+sx2+sx3-x(3))/2
              yone=(sy1+sy2+sy3-y(3))/2
              zone=(sz1+sz2+sz3-z(3))/2
              xyz(xone,yone,zone)=0

NK31=SIDGR1(NV2,JV3)
      NK32=SIDGR2(NV2,JV3)
      NK33=SIDGR3(NV2,JV3)
c     s4=sidgr4(nv2,jv3)
c     tx=tlx(s4)
c     ty=tly(s4)
c     tz=tlz(s4)
c     *******************
      MX1=X(3)+STLX(NK31)
      MX2=X(3)+STLX(NK32)
```

```
      MX3=X(3)+STLX(NK33)
      MY1=Y(3)+STLY(NK31)
      MY2=Y(3)+STLY(NK32)
      MY3=Y(3)+STLY(NK33)
      MZ1=Z(3)+STLZ(NK31)
      MZ2=Z(3)+STLZ(NK32)
      MZ3=Z(3)+STLZ(NK33)
      IF(XYZ(MX1,MY1,MZ1).NE.0) GO TO 64
      IF(XYZ(MX2,MY2,MZ2).NE.0) GO TO 64
      IF(XYZ(MX3,MY3,MZ3).NE.0) GO TO 64
            mxone=(mx1+mx2+mx3-x(3))/2
            myone=(my1+my2+my3-y(3))/2
            mzone=(mz1+mz2+mz3-z(3))/2
            if(xyz(mxone,myone,mzone).ne.0) go to 64

XYZ(MX1,MY1,MZ1)=-1
      XYZ(MX2,MY2,MZ2)=-1
      XYZ(MX3,MY3,MZ3)=-1
      xyz(mxone,myone,mzone)=3
c...
c     end of check of sidechain conformation if sidechain there is not
c     a glycine.
3040      continue
      NK21=SIDGR1(NV1,NV2)
      NK22=SIDGR2(NV1,NV2)
      NK23=SIDGR3(NV1,NV2)
c     **************************
            WX2=VX(NV2)
            WY2=VY(NV2)
            WZ2=VZ(NV2)
      X2=X(3)-WX2
      Y2=Y(3)-WY2
      Z2=Z(3)-WZ2
            IF(LOOK(XYZ,INDGL(2),X2,Y2,Z2,NK21,NK22,NK23)) GO TO 63
      WX1=VX(NV1)
      WY1=VY(NV1)
      WZ1=VZ(NV1)
            X1=X2-WX1
            Y1=Y2-WY1
            Z1=Z2-WZ1
            IF(LOOK(XYZ,INDGL(1),X1,Y1,Z1,13,13,13)) GO TO 63
c
c........OLD CONFORMATIONAL ENERGY (LOCAL)
c
      IC3=ICONF(ICA2,JV3)
      IC2=ICONF(ICA1,ICA2)
      COLD=AC(2,IC2)+AC(3,IC3)
c     s4=sidgr4(ica1,ica2)
c     tx=tlx(s4)
c     ty=tly(s4)
c     tz=tlz(s4)
c     PK23=SIDGR3(ICA1,ICA2)
c     ipk21=ihan1(ica1,ica2)
      QX1=X(2)+slx(ica1,ica2)
      Qy1=y(2)+sly(ica1,ica2)
      Qz1=z(2)+slz(ica1,ica2)

SuX1=X(3)+S1X(ica2,jv3)
      Suy1=y(3)+S1y(ica2,jv3)
      Suz1=z(3)+S1z(ica2,jv3)

EOLD=COLD
     *           +ERG(XYZ,INDGL(3),AM,SuX1,SuY1,SuZ1,3)

c    *           +ERG(XYZ,INDGL(3),AM,SuX3,SuY3,SuZ3,3)
     *           +ERG(XYZ,INDGL(2),AM,QX1,QY1,QZ1,2)

*           +APH(ICA1,ICA2,JV3,2)+APH(ICA2,JV3,ICA(4),3)
     *             +EREPUL(XYZ,X(2),Y(2),Z(2),AREP)
     *              +EHB(XYZ,ICA,PRODV,X(3),Y(3),Z(3),3,AHB)
     *           +EHB(XYZ,ICA,PRODV,X(2),Y(2),Z(2),2,AHB)
```

```
C
C........NEW CONFORMATIONAL ENERGY (LOCAL)
C
          ICA(1)=NV1
          ICA(2)=NV2

IC3=ICONF(NV2,JV3)
      IC2=ICONF(NV1,NV2)
      CNEW=AC(2,IC2)+AC(3,IC3)
C     **************************
C     s4=sidgr4(nv1,nv2)
C     tx=tlx(s4)
C     ty=tly(s4)
C     tz=tlz(s4)

LX1=X2+S1x(nv1,nv2)
      Ly1=y2+S1y(nv1,nv2)
      Lz1=z2+S1z(nv1,nv2)

MuX1=X(3)+S1X(nv2,jv3)
      Muy1=y(3)+S1y(nv2,jv3)
      Muz1=z(3)+S1z(nv2,jv3)

ENEW=CNEW
     *          +ERG(XYZ,INDGL(3),AM,muX1,muY1,MuZ1,3)

*          +ERG(XYZ,INDGL(2),AM,LX1,LY1,LZ1,2)

*          +APH(NV1,NV2,JV3,2)+APH(NV2,JV3,ICA(4),3)
     *          +EREPUL(XYZ,X2,Y2,Z2,AREP)
     *             +EHB(XYZ,ICA,PRODV,X(3),Y(3),Z(3),3,AHB)
     *          +EHB(XYZ,ICA,PRODV,X2,Y2,Z2,2,AHB)
C..........METROPOLIS CRITERION
C
          DE=ENEW-EOLD
          IF(EXP(-DE).LT.vaxran(rn3)) GO TO 63
          ENERG=ENERG+DE
C
C         SET-IN THE NEW CONFORMATION OF THE TAIL
      X(1)=X1
      Y(1)=Y1
      Z(1)=Z1
      X(2)=X2
      Y(2)=Y2
      Z(2)=Z2
          CALL setin(XYZ,INDGL(1),X1,Y1,Z1,13,13,13,1)
      CALL SETIN(XYZ,INDGL(2),X2,Y2,Z2,NK21,NK22,NK23,2)
          QEND=QEND+1
          GO TO 79
C
C         SET-IN THE OLD CONFORMATION OF THE TAIL
 63   if(indgl(3) .eq. 0) go to 641
      XYZ(MX1,MY1,MZ1)=0
      XYZ(MX2,MY2,MZ2)=0
      XYZ(MX3,MY3,MZ3)=0
      xyz(mxone,myone,mzone)=0

64   XYZ(SX1,SY1,SZ1)=-1
      XYZ(SX2,SY2,SZ2)=-1
      XYZ(SX3,SY3,SZ3)=-1
      xyz(xone,yone,zone)=3
 641    continue
          ICA(1)=ICA1
          ICA(2)=ICA2
          CALL setin(XYZ,INDGL(1),X(1),Y(1),Z(1),13,13,13,1)
      CALL SETIN(XYZ,INDGL(2),X(2),Y(2),Z(2),PK21,PK22,PK23,2)
C
C   .      C-TERMINUS (HEAD)
C
 79   JV3=ICA(LENF3)
 80   NV2=INT(vaxran(rn1)*24.)+1
      IF(.NOT.GOODC(JV3,NV2)) GO TO 80
```

```
81   NV1=INT(vaxran(rn2)*24.)+1
     IF(.NOT.GOODC(NV2,NV1)) GO TO 81
C         CONFORMATION IS OK.  CHECK  THE EXCLUDED VOLUME
     CALL REMOVE(XYZ,INDGL(LENF),X(LENF),Y(LENF),Z(LENF),13,13,13)
     ICA2=ICA(LENF2)
     ICA1=ICA(LENF1)
     PK21=SIDGR1(ICA2,ICA1)
     PK22=SIDGR2(ICA2,ICA1)
     PK23=SIDGR3(ICA2,ICA1)
C
     IIII=INDGL(LENF1)
     CALL REMOVE(XYZ,IIII,X(LENF1),Y(LENF1),Z(LENF1),PK21,PK22,PK23)
C         CHECK THE ROTATION OF SIDE GROUP ON THIRD BEAD
     if(indgl(lenf2) .eq. 0) go to 6045
     PK31=SIDGR1(JV3,ICA2)
     PK32=SIDGR2(JV3,ICA2)
     PK33=SIDGR3(JV3,ICA2)

SX1=X(LENF2)+STLX(PK31)
     SY1=Y(LENF2)+STLY(PK31)
     SZ1=Z(LENF2)+STLZ(PK31)
     SX2=X(LENF2)+STLX(PK32)
     SY2=Y(LENF2)+STLY(PK32)
     SZ2=Z(LENF2)+STLZ(PK32)
     SX3=X(LENF2)+STLX(PK33)
     SY3=Y(LENF2)+STLY(PK33)
     SZ3=Z(LENF2)+STLZ(PK33)
     XYZ(SX1,SY1,SZ1)=0
     XYZ(SX2,SY2,SZ2)=0
     XYZ(SX3,SY3,SZ3)=0
          xone=(sx1+sx2+sx3-x(lenf2))/2
          yone=(sy1+sy2+sy3-y(lenf2))/2
          zone=(sz1+sz2+sz3-z(lenf2))/2
          xyz(xone,yone,zone)=0

NK31=SIDGR1(JV3,NV2)
     NK32=SIDGR2(JV3,NV2)
     NK33=SIDGR3(JV3,NV2)

MX1=X(LENF2)+STLX(NK31)
     MY1=Y(LENF2)+STLY(NK31)
     MZ1=Z(LENF2)+STLZ(NK31)
     MX2=X(LENF2)+STLX(NK32)
     MY2=Y(LENF2)+STLY(NK32)
     MZ2=Z(LENF2)+STLZ(NK32)
     MX3=X(LENF2)+STLX(NK33)
     MY3=Y(LENF2)+STLY(NK33)
     MZ3=Z(LENF2)+STLZ(NK33)

IF(XYZ(MX1,MY1,MZ1).NE.0) GO TO 84
     IF(XYZ(MX2,MY2,MZ2).NE.0) GO TO 84
     IF(XYZ(MX3,MY3,MZ3).NE.0) GO TO 84
          mxone=(mx1+mx2+mx3-x(lenf2))/2
          myone=(my1+my2+my3-y(lenf2))/2
          mzone=(mz1+mz2+mz3-z(lenf2))/2
          if(xyz(mxone,myone,mzone).ne.0) go to 84
     XYZ(MX1,MY1,MZ1)=-1
     XYZ(MX2,MY2,MZ2)=-1
     XYZ(MX3,MY3,MZ3)=-1
     xyz(mxone,myone,mzone)=lenf2
C....
6045    continue
     NK21=SIDGR1(NV2,NV1)
     NK22=SIDGR2(NV2,NV1)
     NK23=SIDGR3(NV2,NV1)
          WX2=VX(NV2)
          WY2=VY(NV2)
          WZ2=VZ(NV2)
     X2=X(LENF2)+WX2
     Y2=Y(LENF2)+WY2
     Z2=Z(LENF2)+WZ2
          IF(LOOK(XYZ,IIII,X2,Y2,Z2,NK21,NK22,NK23)) GO TO 83
```

```
      WX1=VX(NV1)
      WY1=VY(NV1)
      WZ1=VZ(NV1)
         X1=X2+WX1
         Y1=Y2+WY1
         Z1=Z2+WZ1
         IF(LOOK(XYZ,INDGL(LENF),X1,Y1,Z1,13,13,13)) GO TO 83
C
C........OLD CONFORMATIONAL ENERGY (LOCAL)
C
      IC3=ICONF(JV3,ICA2)
      IC2=ICONF(ICA2,ICA1)
      COLD=AC(LENF1,IC2)+AC(LENF2,IC3)
c     s4=sidgr4(ica2,ica1)
c     tx=tlx(s4)
c     ty=tly(s4)
c     tz=tlz(s4)
      QX1=X(lenf1)+S1X(ica2,ica1)
      Qy1=y(lenf1)+S1y(ica2,ica1)
      Qz1=z(lenf1)+S1z(ica2,ica1)

SuX1=X(LENF2)+S1X(jv3,ica2)
      Suy1=y(LENF2)+S1y(jv3,ica2)
      Suz1=z(LENF2)+S1z(jv3,ica2)

c     QX1=X(LENF1)+STLX(PK21)*
c     QY1=Y(LENF1)+STLY(PK21)
c     QZ1=Z(LENF1)+STLZ(PK21)
c     QX2=X(LENF1)+STLX(PK22)
c     QY2=Y(LENF1)+STLY(PK22)
c     QZ2=Z(LENF1)+STLZ(PK22)
c     QX3=X(LENF1)+STLX(PK23)
c     QY3=Y(LENF1)+STLY(PK23)
c     QZ3=Z(LENF1)+STLZ(PK23)
      EOLD=COLD
     *          +ERG(XYZ,INDGL(LENF2),AM,SuX1,suY1,suZ1,LENF2)

*           +APH(ICA(LENF4),JV3,ICA2,LENF3)
     *          +APH(JV3,ICA2,ICA1,LENF2)
     *          +ERG(XYZ,IIII,AM,QX1,QY1,QZ1,LENF1)

*          +EREPUL(XYZ,X(LENF1),Y(LENF1),Z(LENF1),AREP)
     *          +EHB(XYZ,ICA,PRODV,X(LENF2),Y(LENF2),Z(LENF2),LENF2,AHB)
     *          +EHB(XYZ,ICA,PRODV,X(LENF1),Y(LENF1),Z(LENF1),LENF1,AHB)

C........NEW CONFORMATIONAL ENERGY (LOCAL)
C
         ICA(LENF1)=NV1
         ICA(LENF2)=NV2

IC3=ICONF(JV3,NV2)
      IC2=ICONF(NV2,NV1)
      CNEW=AC(LENF1,IC2)+AC(LENF2,IC3)

LX1=X2+s1x(nv2,nv1)
      Ly1=y2+s1y(nv2,nv1)
      Lz1=z2+s1z(nv2,nv1)

MuX1=X(lenf2)+S1x(jv3,nv2)
      Muy1=y(lenf2)+S1y(jv3,nv2)
      Muz1=z(lenf2)+S1z(jv3,nv2)

c     LX1=X2+STLX(NK21)
c     LY1=Y2+STLY(NK21)
```

```
c       LZ1=Z2+STLZ(NK21)
c       LX2=X2+STLX(NK22)
c       LY2=Y2+STLY(NK22)
c       LZ2=Z2+STLZ(NK22)
c       LX3=X2+STLX(NK23)
c       LY3=Y2+STLY(NK23)
c       LZ3=Z2+STLZ(NK23)
        ENEW=CNEW
     *            +ERG(XYZ,INDGL(LENF2),AM,muX1,muY1,muZ1,LENF2)

*            +APH(ICA(LENF4),JV3,NV2,LENF3)

*            +APH(JV3,NV2,NV1,LENF2)
     *            +ERG(XYZ,IIII,AM,LX1,LY1,LZ1,LENF1)

*            +EREPUL(XYZ,X2,Y2,Z2,AREP)
     *            +EHB(XYZ,ICA,PRODV,X(LENF2),Y(LENF2),Z(LENF2),LENF2,AHB)
     *            +EHB(XYZ,ICA,PRODV,X2,Y2,Z2,LENF1,AHB)

c
c.........METROPOLIS CRITERION
c
        DE=ENEW-EOLD
        IF(EXP(-DE).LT.vaxran(rn3)) GO TO 83
        ENERG=ENERG+DE
c
c       SET-IN THE NEW CONFORMATION OF THE HEAD
    X(LENF)=X1
    Y(LENF)=Y1
    Z(LENF)=Z1
    X(LENF1)=X2
    Y(LENF1)=Y2
    Z(LENF1)=Z2
        CALL setin(XYZ,INDGL(LENF),X1,Y1,Z1,13,13,13,1)
    CALL SETIN(XYZ,IIII,X2,Y2,Z2,NK21,NK22,NK23,LENF1)
        QEND=QEND+1
        GO TO 7007
c
c       SET-IN THE OLD CONFORMATION OF THE TAIL
 83     if(indgl(lenf2) .eq. 0) go to 675
    XYZ(MX1,MY1,MZ1)=0
    XYZ(MX2,MY2,MZ2)=0
    XYZ(MX3,MY3,MZ3)=0
    xyz(mxone,myone,mzone)=0

84     XYZ(SX1,SY1,SZ1)=-1
    XYZ(SX2,SY2,SZ2)=-1
    XYZ(SX3,SY3,SZ3)=-1
    xyz(xone,yone,zone)=lenf2
675      continue
        ICA(LENF1)=ICA1
        ICA(LENF2)=ICA2
    CALL setin(XYZ,INDGL(LENF),X(LENF),Y(LENF),Z(LENF),13,13,13,1)
    CALL SETIN(XYZ,IIII,X(LENF1),Y(LENF1),Z(LENF1),PK21,PK22,PK23,LENF1)

c
c    WAVE LIKE MOTION OF THE CHAIN FRAGMENT, VARIOUS CONFORMATIONS
c
 7007     I=INT(AL9*vaxran(rn2))+3
      if( vaxran(rn3) .gt. .01) then
      af=1.10
      else
      af =a1
      end if
c
c    I+2 IS THE CENTRAL BEAD OF THE PIECE TO BE CUT-OFF
c    JJ - IS THE CENTRAL ONE OF THE PIECE TO BE CONSTRUCTED
c    SEARCH FOR U-SHAPED (OF VARIOUS WIDTH) CONFORMATIONS
```

```
C
      IV2=ICA(I)
      IV5=ICA(I+3)
      VX2=VX(IV2)
      VX5=VX(IV5)
      IF(VX2.NE.-VX5) GO TO 7770
      VY2=VY(IV2)
      VY5=VY(IV5)
      IF(VY2.NE.-VY5) GO TO 7770
      VZ2=VZ(IV2)
      VZ5=VZ(IV5)
      IF(VZ2.NE.-VZ5) GO TO 7770
C                           LOOK FOR THE SECOND END
      IVA=MOD(ICLOCK,WAVEL)
      MIX=-MIX
      JJ=I+2+MIX*(5+IVA)
      IF(JJ.LT.4.OR.JJ.GT.LENF3) GO TO 7770
C                           ACCEPTED DOWN THE CHAIN CHOICE
C                           I-END CONSTRUCTION    (CUT-OFF)
      IV3=ICA(I+2)
      IV4=ICA(I+1)
C                           KINK PERFORMEEED (KINK==1)
      IV1=ICA(I-1)
      I4=I+4
      IV6=ICA(I4)
      IF(GOODC(IV1,IV3).AND.GOODC(IV4,IV6)) GO TO 200
C                           ELSE TRY KINK FLIP OF THE TOP

INV3=VECT1(IV3,IV4,KINK)
         IV4=VECT2(IV3,IV4,KINK)
         IV3=INV3
         IF(.NOT.GOODC(IV1,IV3)) GO TO 7770
         IF(.NOT.GOODC(IV4,IV6)) GO TO 7770

C                           CONSTRUCT THE NEW JJ- END
  200 J1=JJ-1
      JV1=ICA(J1)
      JV2=ICA(JJ)
      JVL=ICA(JJ-2)
      J3=JJ+1
      JVP=ICA(J3)
  201 V=INT(vaxran(rn1)*24.)+1
      IF(.NOT.GOODC(JVL,V)) GO TO 201
      WVX=VX(V)
      WVY=VY(V)
      WVZ=VZ(V)
      VM=VECTOR(-WVX,-WVY,-WVZ)
      IF(.NOT.GOODC(VM,JVP)) GO TO 201
C                           TOP OF THE JJ-END CNCTRUCTED
         DO KINK=1,5
         JN1=VECT1(JV1,JV2,KINK)
         IF(GOODC(V,JN1)) THEN
              JN2=VECT2(JV1,JV2,KINK)
              IF(GOODC(JN2,VM)) GO TO 202
              END IF
         ENDDO
      GO TO 7770
C
C     MODIFFICATION OF THE BOND STRING ARRAY ICA, STORE THE OLD ONE
C
  202 IF(MIX.GT.0) THEN
         IFIRST=I
         ILAST=J3
         ELSE
         IFIRST=J1
         ILAST=I4
         ENDIF

DO J=IFIRST-1,ILAST
      ICAO(J)=ICA(J)
      ENDDO
```

```
C
      IF(MIX.GT.0) THEN
         ICA(I)=IV3
         ICA(I+1)=IV4
         DO J=I4,JJ-2
         ICA(J-2)=ICAO(J)
         ENDDO
         ICA(JJ)=VM
         ICA(J1)=JN2
         ICA(J1-1)=JN1
         ICA(J1-2)=V
      ELSE
         ICA(I4-1)=IV4
         ICA(I4-2)=IV3
         DO J=J3,I-1
         ICA(J+2)=ICAO(J)
         ENDDO
         ICA(J1)=V
         ICA(JJ)=JN1
         ICA(J3)=JN2
         ICA(J3+1)=VM
      END IF
C                        REMOVE THE STRING
      DO K=IFIRST,ILAST
      II=ICAO(K-1)
      KK=ICAO(K)
      IKS1=SIDGR1(II,KK)
      IKS2=SIDGR2(II,KK)
      IKS3=SIDGR3(II,KK)
      XJ=X(K)
      YJ=Y(K)
      ZJ=Z(K)
      CALL REMOVE(XYZ,INDGL(K),XJ,YJ,ZJ,IKS1,IKS2,IKS3)
      ENDDO
C                        SETIN AND EXCLUDED
C                        VOLUME TEST
      IFA=IFIRST-1

XJ=X(IFA)
      YJ=Y(IFA)
      ZJ=Z(IFA)
      DO J=IFIRST,ILAST
      II=ICA(J-1)
      JJJ=ICA(J)
      XJ=XJ+VX(II)
      YJ=YJ+VY(II)
      ZJ=ZJ+VZ(II)
      XNEW(J)=XJ
      YNEW(J)=YJ
      ZNEW(J)=ZJ
      IKS1=SIDGR1(II,JJJ)
      IKS2=SIDGR2(II,JJJ)
      IKS3=SIDGR3(II,JJJ)

IF(LOOK(XYZ,INDGL(J),XJ,YJ,ZJ,IKS1,IKS2,IKS3)) THEN
C                        THEN REMOVE AND TERMINATE
          IF(J.EQ.IFIRST) GO TO 204
          DO K=IFIRST,J-1
          KK=ICA(K-1)
          KKK=ICA(K)
      IKS1=SIDGR1(KK,KKK)
      IKS2=SIDGR2(KK,KKK)
      IKS3=SIDGR3(KK,KKK)
      CALL REMOVE(XYZ,INDGL(K),XNEW(K),YNEW(K),ZNEW(K),IKS1,IKS2,IKS3)
      ENDDO

204       DO I=IFIRST,ILAST
          ICA(I)=ICAO(I)
          II=ICA(I-1)
```

```
            JJJ=ICA(I)
            IKS1=SIDGR1(II,JJJ)
            IKS2=SIDGR2(II,JJJ)
            IKS3=SIDGR3(II,JJJ)
      CALL setin(XYZ,INDGL(I),X(I),Y(I),Z(I),IKS1,IKS2,IKS3,I)
            ENDDO
            GO TO 7770
            ELSE
C                              SET NEW BEAD
        CALL SETIN(XYZ,INDGL(J),XJ,YJ,ZJ,IKS1,IKS2,IKS3,J)
            ENDIF
      ENDDO
C                  THE NEW STRING KEEPS EXCLUDED VOLUME
C
C
C     COMPUTATION OF ENERGY OF THE NEW CONFORMATION AND REMOVE STRING
C ENEW=0.
      ER=0.
      E=0.
      DO J=IFIRST,ILAST
      I=J-1
      II=ICA(I)
      JJ=ICA(J)
            XJ=XNEW(J)
            YJ=YNEW(J)
            ZJ=ZNEW(J)
      IKS1=SIDGR1(II,JJ)
      IKS2=SIDGR2(II,JJ)
      IKS3=SIDGR3(II,JJ)

C                         ROTATIONAL CONTRIBUTION
      JCONF=ICONF(II,JJ)
      ENEW=ENEW+AC(J,JCONF)+APH(II,JJ,ICA(J+1),J)
C                         INTERACTIONS OF SIDE GROUPS
            IX1=XJ+S1x(ii,jj)
            Iy1=yJ+S1y(ii,jj)
            Iz1=zJ+S1z(ii,jj)

E=E+ERG(XYZ,INDGL(J),AM,IX1,IY1,IZ1,J)

C                         COOPERATIVE AND HYDROGEN BOND
      E=E+EHB(XYZ,ICA,PRODV,XJ,YJ,ZJ,J,AHB)
C                         REPULSIVE INTERACTIONS

ER=ER+EREPUL(XYZ,XJ,YJ,ZJ,AREP)
              CALL REMOVE(XYZ,INDGL(J),XJ,YJ,ZJ,IKS1,IKS2,IKS3)
      ENDDO
      ENEW=ENEW+APH(ICA(IFIRST-2),ICA(IFA),ICA(IFIRST),IFA)
      ENEW=ENEW+E+ER
C
C
C
C     COMPUTATION OF THE OLD ENERGY AND SETIN OF THE CHAIN PIECE
C
              DO J=IFIRST,ILAST
              I=ICA(J)
              ICA(J)=ICAO(J)
              ICAO(J)=I
              ENDDO
C             NEW ICA STORED IN ICAO AT THIS POINT
      EOLD=0.
      ER=0.
      E=0.
      DO J=IFIRST,ILAST
      XJ=X(J)
      YJ=Y(J)
      ZJ=Z(J)
      II=ICA(J-1)
      JJJ=ICA(J)
            IKS1=SIDGR1(II,JJJ)
            IKS2=SIDGR2(II,JJJ)
            IKS3=SIDGR3(II,JJJ)
```

```
c       s4=sidgr4(ii,jjj)
c       tx=tlx(s4)
c       ty=tly(s4)
c       tz=tlz(s4)
        CALL setin(XYZ,INDGL(J),XJ,YJ,ZJ,IKS1,IKS2,IKS3,J)
c
        JCONF=ICONF(II,JJJ)
        EOLD=EOLD+AC(J,JCONF)+APH(II,JJJ,ICA(J+1),J)
c                       INTERACTIONS OF SIDE GROUPS
        IX1=XJ+S1x(ii,jjj)
        Iy1=yJ+S1y(ii,jjj)
        Iz1=zJ+S1z(ii,jjj)
        E=E+ERG(XYZ,INDGL(J),AM,IX1,IY1,IZ1,J)

c                       COOPERATIVE AND HYDROGEN BOND
        E=E+EHB(XYZ,ICA,PRODV,XJ,YJ,ZJ,J,AHB)
c                       REPULSIVE INTERACTIONS
        ER=ER+EREPUL(XYZ,XJ,YJ,ZJ,AREP)
        ENDDO
        EOLD=EOLD+APH(ICA(IFIRST-2),ICA(IFA),ICA(IFIRST),IFA)
        EOLD=EOLD+E+ER c
c       METROPOLIS CRITERION
c
        DE=ENEW-EOLD
        IF(EXP(-DE*af).GT.vaxran(rn3)) THEN
c                       ACCEPTED
        QWAVE=QWAVE+1
        ENERG=ENERG+DE
            DO J=IFIRST, ILAST
            II=ICA(J-1)
            JJ=ICA(J)
            IKS1=SIDGR1(II,JJ)
            IKS2=SIDGR2(II,JJ)
            IKS3=SIDGR3(II,JJ)
        CALL REMOVE(XYZ,INDGL(J),X(J),Y(J),Z(J),IKS1,IKS2,IKS3)
            ENDDO
        DO J=IFIRST,ILAST
        XJ=XNEW(J)
        YJ=YNEW(J)
        ZJ=ZNEW(J)
        X(J)=XJ
        Y(J)=YJ
        Z(J)=ZJ
        II=ICAO(J-1)
        JJ=ICAO(J)
            IKS1=SIDGR1(II,JJ)
            IKS2=SIDGR2(II,JJ)
            IKS3=SIDGR3(II,JJ)
        CALL setin(XYZ,INDGL(J),XJ,YJ,ZJ,IKS1,IKS2,IKS3,J)
        ICA(J)=ICAO(J)
        ENDDO
        ENDIF
c
 7770   CONTINUE
c
c                       OPTIONAL NORMALISATION OF THE COORDINATES
        SX=0
        SY=0
        SZ=0
        DO I=1,LENF
        SX=SX+X(I)
        SY=SY+Y(I)
        SZ=SZ+Z(I)
        ENDDO
c                       CENTRE OF GRAVITY COORDINATES
        ASX=FLOAT(SX)/LENF
        ASY=FLOAT(SY)/LENF
        ASZ=FLOAT(SZ)/LENF
        XSHIFT=MID-ASX
        YSHIFT=MID-ASY
        ZSHIFT=MID-ASZ
```

```
       IF((XSHIFT**2+YSHIFT**2+ZSHIFT**2).GT.30) THEN
C                                  NORMALISATION
       CALL REMOVE(XYZ,INDGL(1),X(1),Y(1),Z(1),13,13,13)
       CALL REMOVE(XYZ,INDGL(LENF),X(LENF),Y(LENF),Z(LENF),13,13,13)
       DO I=2,LENF1
       II=ICA(I-1)
       JJ=ICA(I)
       SID1=SIDGR1(II,JJ)
       SID2=SIDGR2(II,JJ)
       SID3=SIDGR3(II,JJ)
       CALL REMOVE(XYZ,INDGL(I),X(I),Y(I),Z(I),SID1,SID2,SID3)
       ENDDO
       DO I=1,LENF
       X(I)=X(I)+XSHIFT
       Y(I)=Y(I)+YSHIFT
       Z(I)=Z(I)+ZSHIFT
       ENDDO
       sxd=sxd-xshift
            syd=syd-yshift
       szd=szd-zshift CALL setin(XYZ,INDGL(1),X(1),Y(1),Z(1),13,13,13,1)
       CALL setin(XYZ,INDGL(LENF),X(LENF),Y(LENF),Z(LENF),13,13,13,1)
       DO I=2,LENF1
       II=ICA(I-1)
       JJ=ICA(I)
       SID1=SIDGR1(II,JJ)
       SID2=SIDGR2(II,JJ)
       SID3=SIDGR3(II,JJ)

CALL setin(XYZ,INDGL(I),X(I),Y(I),Z(I),SID1,SID2,SID3,I)
       ENDDO
       END IF
C
7700 CONTINUE
C write(13,*)iterm,energ,sxd,syd,szd
       do i=1,lenf
       xt(i)=x(i)+sxd
       yt(i)=y(i)+syd
       zt(i)=z(i)+szd
       end do
       write(13,*)(xt(i),yt(i),zt(i),i=1,lenf)

R2=(X(LENF)-X(1))**2+(Y(LENF)-Y(1))**2+(Z(LENF)-Z(1))**2
       asumr2=asumr2+r2
       etot2=etot2+energ*energ
       etot=etot+energ
       AS2=0.
       SX=0
       SY=0
       SZ=0
       DO I=1,LENF
       SX=SX+X(I)
       SY=SY+Y(I)
       SZ=SZ+Z(I)
       ENDDO
C                          CENTRE OF GRAVITY COORDINATES
       ASX=FLOAT(SX)/LENF
       ASY=FLOAT(SY)/LENF
       ASZ=FLOAT(SZ)/LENF

DO I=1,LENF

BX=(ASX-X(I))**2
       BY=(ASY-Y(I))**2
       BZ=(ASZ-Z(I))**2
       AS2=AS2+BX+BY+BZ
       ENDDO
       AS2=AS2/LENF
       asums2=asums2+as2
```

```
c      insertion of the native contact pairs nt=0.d0
       nct=0.
       do 1400 i=2,lenf2
       k=i+1
       ii=ica(i-1)
       iii=ica(i)
       SX1=s1x(ii,iii)+x(i)
       Sy1=s1y(ii,iii)+y(i)
       Sz1=s1z(ii,iii)+z(i)
           DO 1400 J=K,LENF1
c it is not counting the nearest1 down-the-chain neighbours, which may be
c usefull for some purposes ............................................
           if(iabs(i-j).eq.1) go to 1400
           iR2=(X(J)-X(I))**2+(Y(J)-Y(I))**2+(Z(J)-Z(I))**2
           IF(iR2.GT.18) GO TO 1400
           II=ICA(J-1)
           III=ICA(J)
           Kx1=s1X(II,III)+X(J)
           KY1=S1Y(II,III)+Y(J)
           KZ1=S1Z(II,III)+Z(J)
           R11=(SX1-KX1)**2+(SY1-KY1)**2+(SZ1-KZ1)**2
           IF(R11.EQ.2) then
           nct=nct+inc(i,j)
           nt=nt+1
           end if
1400   CONTINUE
       ant=ant+nt
       anct=anct+nct
       WRITE(6,8009) ITERM, R2, AS2, ENERG,nct,nt
8009   FORMAT(2X,2I5,F8.2,F10.4,3x,i3,2x,i3)
c
 7777      CONTINUE
c
 9000                      CONTINUE
       REWIND(UNIT=10)
       WRITE(10,8000) LENF
       DO I=1,LENF
       WRITE(10,8000) X(I),Y(I),Z(I)
       ENDDO c      DO I=2,LENF1
c      WRITE(6,8000) I,X(I),Y(I),Z(I),ICA(I),ICONF(ICA(I-1),ICA(I))
c      ENDDO c      ACCEPTANCE RATIOS FOR VARIOUS MOVES
       FKINK=FLOAT(QKINK)/FLOAT(NCYCLE*PHOT)/AL4/100.
       FWAVE=FLOAT(QWAVE)/FLOAT(NCYCLE*PHOT)/100.
       FROT=FLOAT(QROT)/FLOAT(NCYCLE*PHOT)/100.
       FEND=FLOAT(QEND)/FLOAT(NCYCLE*PHOT)/200.
       etot=etot/ncycle
       etot2=etot2/ncycle
       cv=etot2-etot*etot
       asumr2=asumr2/ncycle
           asums2=asums2/ncycle anct=anct/ncycle
       ant=ant/ncycle
       write(6,9942)etot,etot2,cv,asumr2,asums2,anct,ant
9942   format(1x,'<E>=',1F10.4,5X,'<E2>=',1Pd15.8,5X,'CV=',1pd15.8,/,
      *      'mean-square-end to end vector=',1pd15.8,/,
      *            '<S2>=',1pd15.8,/, 'native contacts=',1pd15.8,/,
      *         ' number of contacts=',1pd15.8,/)

write(6,8012)
8012   format(1x,'     fkink=     fend =      fwave=       frot=')
       WRITE(6,8002) FKINK,FEND,FWAVE,FROT
c
c_     DETAILED ANALYSE OF THE CHAIN STRUCTURE
```

```
c
      WRITE(6,8004)
 8004    FORMAT(1X,//,8X,'VECTOR1    VECTOR2',8x,'SIDE 1/2/3',6x,'HANDENES',/)

DO I=2,LENF1
      II=ICA(I-1)
      JJ=ICA(I)
      KK=ICA(I+1)

Icj=ICONF(II,JJ)
         SID1=SIDGR1(II,JJ)
         SID2=SIDGR2(II,JJ)
         SID3=SIDGR3(II,JJ)

WX1=VX(II)
      WY1=VY(II)
      WZ1=VZ(II)
      WX2=VX(JJ)
      WY2=VY(JJ)
      WZ2=VZ(JJ)
      WX3=VX(KK)
      WY3=VY(KK)
      WZ3=VZ(KK)
      R3=(WX1+WX2+WX3)**2+(WY1+WY2+WY3)**2+(WZ1+WZ2+WZ3)**2
      W1X=(S1X(ii,jj))*INDGL(I)
      W1y=(S1y(ii,jj))*INDGL(I)
      W1z=(S1z(ii,jj))*INDGL(I)
c     specification of the non interactiong fcc sites W2X=stlx(sid1)*INDGL(I)
      W2y=stly(sid1)*INDGL(I)
      W2z=stlz(sid1)*INDGL(I)

W3X=stlx(sid2)*INDGL(I)
      W3y=stly(sid2)*INDGL(I)
      W3z=stlz(sid2)*INDGL(I)

W4X=stlx(sid3)*INDGL(I)
      W4y=stly(sid3)*INDGL(I)
      W4z=stlz(sid3)*INDGL(I)

IHX=(WY1*WZ2-WY2*WZ1)*INDGL(I)
      IHY=(WX2*WZ1-WZ2*WX1)*INDGL(I)
      IHZ=(WX1*WY2-WY1*WX2)*INDGL(I)
      IH1=ISIGN(1,(IHX*W1X+IHY*W1Y+IHZ*W1Z))

WRITE(6,8003) I,WX1,WY1,WZ1,WX2,WY2,WZ2,
     *    W1X,W1Y,W1Z,W2X,W2Y,W2Z,W3X,W3Y,W3Z,IH1,icj,r3
      ENDDO
 8003    FORMAT(1X,I4,X,3I3,X,3I3,2X,3I2,X,3I2,X,3I2,2X,I2,x,i3,x,i3)
 8002    FORMAT(1X,//,5X,5F10.6)
      write(6,8010)
 8010    format(1x,/,5x,50(1h-),/)
 8000    FORMAT(3X,5I4,I6)
      do i=6,18,2
      write(6,8005) i,iflip(i,1),iflip(i,2),iflip(i,3),iflip(i,4),
     *   iflip(i,5)
      enddo
 8005    format(1x,i5,5i8)
c
c     testl of occupancy - a direct one
      lenfo7=lenf*7
      lenf23=lenf2-NBGL
      write(6,8006) lenf, lenfo7, lenf23,nbgl
 8006    format(1x,/,5x,'lenf  7*lenf  lenf-2 -nbgl  ngbl',4i6,/)
      isi=0
      ione=0
```

```
            ioc=0
      do xx=1,max
      do yy=1,max
      do zz=1,max
      point=xyz(xx,yy,zz)
      if(point.ne.0) then if(point.gt.0) then
                  isi=isi+1
            else
                  if(point.eq.-1) ione=ione+1
                     ioc=ioc+1
            endif
      endif
      enddo
      enddo
      enddo
c writing of the backbone and side groups coordinates - without the
c central (inert) bead
c
c     do   i=2,lenf2
c     ii=ica(i-1)
c     iii=ica(i)
c     SX1=stlLX(SIDGR1(II,III))+X(I)
c     SY1=stlLY(SIDGR1(II,III))+Y(I)
c     SZ1=stlLZ(SIDGR1(II,III))+Z(I)
c     SX2=stlLX(SIDGR2(II,III))+X(I)
c     SY2=stlLY(SIDGR2(II,III))+Y(I)
c     SZ2=stlLZ(SIDGR2(II,III))+Z(I)
c     SX3=stlLX(SIDGR3(II,III))+X(I)
c     SY3=stlLY(SIDGR3(II,III))+Y(I)

c     SZ3=stlLZ(SIDGR3(II,III))+Z(I)
c     write(6,420) x(i),y(i),z(i),sx1,sy1,sz1,sx2,sy2,sz2,
c    *  sx3,sy3,sz3
c 420     format(5x,4(2x,3i4))
c     enddo
      ioc=ioc-3*(lenf2-nbgl)
      ione=(ione-14)/3 +2
c     there are 3 -1 per side chain that is not a glycine
c     let us count the number of excess minus ones write(6,8007) ione, ioc,isi
 8007       format(1x,//,1X,'L-GLY, occupancy and side groups ',3i6,//,
     *  5x,'***********  contact map ************',/)
      do 400 i=2,lenf2
      k=i+1
      ii=ica(i-1)
      iii=ica(i)
c     s4=sidgr4(ii,iii)
c     tx=tlx(s4)
c     ty=tly(s4)
c     tz=tlz(s4)
c     ih1=ihan1(ii,iii)
c     ih2=ihan2(ii,iii)
c     ih3=ihan3(ii,iii)

SX1=slx(ii,iii)+x(i)
      Sy1=sly(ii,iii)+y(i)
      Sz1=slz(ii,iii)+z(i)

DO 400 J=K,LENF1
c it is not counting the nearestl down-the-chain neighbours, which may be
c usefull for some purposes .................................
         if(iabs(i-j).eq.1) go to 400
         R2=(X(J)-X(I))**2+(Y(J)-Y(I))**2+(Z(J)-Z(I))**2
         IF(R2.GT.18) GO TO 400
         II=ICA(J-1)
         III=ICA(J)
         KX1=slX(II,III)+X(J)
         KY1=S1Y(II,III)+Y(J)
         KZ1=S1Z(II,III)+Z(J)
```

```
      R11=(SX1-KX1)**2+(SY1-KY1)**2+(SZ1-KZ1)**2
      mult=0

IF(R11.EQ.2) MULT=MULT+1
          IF(MULT.EQ.0) GO TO 400
          IF(IHYD(I).GT.0.AND.IHYD(J).GT.0) THEN
          WRITE(6,410) I,J,MULT
          go to 400
          endif
          IF(IHYD(I).LT.0.AND.IHYD(J).LT.0) THEN
              WRITE(6,411) I,J,MULT
              ELSE
              WRITE(6,412) I,J,MULT
              ENDIF
400   CONTINUE
410   FORMAT(5X,I3,' and',I3,' phil-phil   multiplicity',i3)
411   FORMAT(3X,'**',I3, ' and',I3,' PHOB-PHOB   multiplicity',i3)
412   FORMAT(5X,I3,' and',I3,' phil-PHOB   multiplicity',i3)

CLOSE(UNIT=1)
      CLOSE(UNIT=2)
      CLOSE(UNIT=5)
      CLOSE(UNIT=6)
      CLOSE(UNIT=10)

stOP

END function vaxran(iseed)
              equivalence (iyfl,yfl2)
              data mask,mask2/x'3f000000',x'3f800000'/
              iseed=iseed*69069 + 1
              nseed=rshift(iseed,8)
              if(iseed.lt.0) then
                iyfl= mask2+nseed
                vaxran=yfl2
              else
                iyfl=mask+nseed
                vaxran=yfl2-.5
              endif
              return
              end C
C           .............SIDE *3 ...GLYCINE......................
C      REMOVES THE CLUSTER (RESIDUE + SIDE GROUP)
       SUBROUTINE REMOVE (XYZ,INDGL,JX,JY,JZ,ID1,ID2,ID3)
       INTEGER XYZ(150,150,150),STLX(13),STLY(13),STLZ(13)
C      FCC LATTICE VECTORS (AND 000)
       DATA STLX /4*0,-1,1,-1,1,-1,1,-1,1,0/
       DATA STLY /-1,1,-1,1,1,1,-1,4*0,-1,1,0/
       DATA STLZ /1,-1,-1,1,2*0,1,-1,-1,1,3*0/
C
              IF(INDGL.EQ.0) GO TO 88
       IX=JX+STLX(ID1)
       IY=JY+STLY(ID1)
       IZ=JZ+STLZ(ID1)
       XYZ(IX,IY,IZ)=0
       IIX=JX+STLX(ID2)
       IIY=JY+STLY(ID2)
       IIZ=JZ+STLZ(ID2)
       XYZ(IIX,IIY,IIZ)=0
       IIIX=JX+STLX(ID3)
       IIIY=JY+STLY(ID3)
       IIIZ=JZ+STLZ(ID3)
       XYZ(IIIX,IIIY,IIIZ)=0
              LX=(IX+IIX+IIIX-JX)/2
              LY=(IY+IIY+IIIY-JY)/2
              LZ=(IZ+IIZ+IIIZ-JZ)/2
              XYZ(LX,LY,LZ)=0
```

```
 88     XYZ(JX,JY,JZ)=0
        IXL=JX-1
        XYZ(IXL,JY,JZ)=0
        IXP=JX+1
        XYZ(IXP,JY,JZ)=0
        IYL=JY-1
        XYZ(JX,IYL,JZ)=0
        IYP=JY+1
        XYZ(JX,IYP,JZ)=0
        IZL=JZ-1
        XYZ(JX,JY,IZL)=0
        IZP=JZ+1
        XYZ(JX,JY,IZP)=0
        RETURN
        END

C       ................SIDE *3 ..glycine.....................
C       THIS SUBROUTINE SETS -INDEX TO THE EXCLUDED VOLUME ENVELOPE
C       AND INDEX=2,.... LENF1 AT THE SIDE GROUP POSITION. BOTH THE
C       TERMINUSES ARE CODED -1 (IT IS USED IN ENERGY CALCULATIONS)
C
c       ...................................................
c
c       ONLY THE FCC LATTICE VECTORS ARE ALLOWED TO INTERACT
c       subroutine setind.f
c       includes check for handedness so that all interacting points
c       are left handed
        SUBROUTINE SETIN (XYZ,INDGL,JX,JY,JZ,ID1,ID2,ID3,IND)
        INTEGER XYZ(150,150,150),STLX(13),STLY(13),STLZ(13),INDGL
.C      FCC LATTICE VECTORS (AND 000)
        DATA STLX /4*0,-1,1,-1,1,-1,1,-1,1,0/
        DATA STLY /-1,1,-1,1,1,-1,4*0,-1,1,0/
        DATA STLZ /1,-1,-1,1,2*0,1,-1,-1,1,3*0/
                if(indgl.eq.0) go to 88
        IX=JX+STLX(ID1)
        IY=JY+STLY(ID1)
        IZ=JZ+STLZ(ID1)
        XYZ(IX,IY,IZ)=-1
        IIX=JX+STLX(ID2)
        IIY=JY+STLY(ID2)
        IIZ=JZ+STLZ(ID2)
        XYZ(IIX,IIY,IIZ)=-1
        IIIX=JX+STLX(ID3)
        IIIY=JY+STLY(ID3)
        IIIZ=JZ+STLZ(ID3)
        XYZ(IIIX,IIIY,IIIZ)=-1
                LX=(IX+IIX+IIIX-JX)/2
                LY=(IY+IIY+IIIY-JY)/2
                LZ=(IZ+IIZ+IIIZ-JZ)/2
                XYZ(LX,LY,LZ)=ind
 88     XYZ(JX,JY,JZ)=-IND
        IXL=JX-1
        XYZ(IXL,JY,JZ)=-IND
        IXP=JY+1
        XYZ(IXP,JY,JZ)=-IND
        IYL=JY-1
        XYZ(JX,IYL,JZ)=-IND
        IYP=JY+1
        XYZ(JX,IYP,JZ)=-IND
        IZL=JZ-1
        XYZ(JX,JY,IZL)=-IND
        IZP=JZ+1
        XYZ(JX,JY,IZP)=-IND
        RETURN
        END C       ...................SIDE *3 ...glycine.....................
C       CHECK OF OCCUPANCY - ENTIRE CLUSTER (RESIDUE+SIDE GROUP)
        FUNCTION LOOK(XYZ,INDGL,JX,JY,JZ,ID1,ID2,ID3)
        LOGICAL LOOK
        INTEGER XYZ(150,150,150),STLX(13),STLY(13),STLZ(13)
C       FCC LATTICE VECTORS (AND 000)
        DATA STLX /4*0,-1,1,-1,1,-1,1,-1,1,0/
        DATA STLY /-1,1,-1,1,1,-1,4*0,-1,1,0/
        DATA STLZ /1,-1,-1,1,2*0,1,-1,-1,1,3*0/
                LOOK=.FALSE.
```

```
C
              IF(INDGL.EQ.0) GO TO 88
       IX=JX+STLX(ID1)
       IY=JY+STLY(ID1)
       IZ=JZ+STLZ(ID1)
       IF(XYZ(IX,IY,IZ).NE.0) THEN
              LOOK=.TRUE.
              RETURN
              ENDIF
       IIX=JX+STLX(ID2)
       IIY=JY+STLY(ID2)
       IIZ=JZ+STLZ(ID2)
       IF(XYZ(IIX,IIY,IIZ).NE.0) THEN
              LOOK=.TRUE.
              RETURN
              ENDIF
       IIIX=JX+STLX(ID3)
       IIIY=JY+STLY(ID3)
       IIIZ=JZ+STLZ(ID3)
       IF(XYZ(IIIX,IIIY,IIIZ).NE.0) THEN
              LOOK=.TRUE.
              RETURN
              ENDIF
       LX=(IX+IIX+IIIX-JX)/2
       LY=(IY+IIY+IIIY-JY)/2
       LZ=(IZ+IIZ+IIIZ-JZ)/2
       IF(XYZ(LX,LY,LZ).NE.0) THEN
              LOOK=.TRUE.
              RETURN
              ENDIF
C
88     IF(XYZ(JX,JY,JZ).NE.0) THEN
              LOOK=.TRUE.
              RETURN
              ENDIF
       IXL=JX-1
       IF(XYZ(IXL,JY,JZ).NE.0) THEN
              LOOK=.TRUE.
              RETURN
              ENDIF
       IXP=JX+1
       IF(XYZ(IXP,JY,JZ).NE.0) THEN
              LOOK=.TRUE.
              RETURN
       IYL=JY-1
       IF(XYZ(JX,IYL,JZ).NE.0) THEN
              LOOK=.TRUE.
              RETURN
              ENDIF
       IYP=JY+1
       IF(XYZ(JX,IYP,JZ).NE.0) THEN
              LOOK=.TRUE.
              RETURN
              ENDIF
       IZL=JZ-1
       IF(XYZ(JX,JY,IZL).NE.0) THEN
              LOOK=.TRUE.
              RETURN
              ENDIF
       IZP=JZ+1
       IF(XYZ(JX,JY,IZP).NE.0) LOOK=.TRUE.
       RETURN
       END

C     ............... side 3 ........glycine.........................
C     THIS FUNCTION COMPUTES THE STRENGTH OF INTERACTIONS BETWEEN THE
C     SIDE GROUPS - only the nearest neighbours r=1, for ak102gly.f
c     all interactions are at a distance 2
c
c     program setind.f 5/12/89
       FUNCTION ERG(XYZ,INDGL,AM,KSX,KSY,KSZ,J)
       DIMENSION AM(150,150)
       INTEGER XYZ(150,150,150),P1,P2,P3,P4,P5,P6,p7,p8,p9
       integer p10,p11,p12
```

```
      ERG=0.
      IF(INDGL.EQ.0) RETURN

IX=KSX-1
      JX=KSX+1
      IY=KSY-1
      JY=KSY+1
      IZ=KSZ-1
      JZ=KSZ+1
C
c     vectors in the z plane
      P1=XYZ(JX,jy,KSZ)
      IF(P1.GT.0) ERG=ERG+AM(P1,J)
      P2=XYZ(jX,iY,KSZ)
      IF(P2.GT.0) ERG=ERG+AM(P2,J)
      P3=XYZ(iX,jy,KSZ)
      IF(P3.GT.0) ERG=ERG+AM(P3,J)
      p4=XYZ(iX,iY,KSZ)
      IF(p4.GT.0) ERG=ERG+AM(p4,J)

c     vectors in the x plane
      p5=XYZ(KSX,JY,jZ)
      IF(p5.GT.0) ERG=ERG+AM(p5,J)
      p6=XYZ(KSX,IY,jZ)
      IF(p6.GT.0) ERG=ERG+AM(p6,J)
      p7=XYZ(KSX,JY,iZ)
      IF(p7.GT.0) ERG=ERG+AM(p7,J)
      p8=XYZ(KSX,IY,iz)
      IF(p8.GT.0) ERG=ERG+AM(p8,J)

C     VECTORS IN THE Y PLANE
      P9=XYZ(IX,KSY,JZ)
      IF(P9.GT.0) ERG=ERG+AM(P9,J)
      P10=XYZ(IX,KSY,IZ)
      IF(P10.GT.0) ERG=ERG+AM(P10,J)
      P11=XYZ(JX,KSY,JZ)
      IF(P11.GT.0) ERG=ERG+AM(P11,J)
      P12=XYZ(JX,KSY,IZ)
      IF(P12.GT.0) ERG=ERG+AM(P12,J)
      RETURN
      END

C     repulsion only to r2=5
C
C     THIS FUNCTION COMPUTES THE STRENGTH OF REPULSIVE INTERACTIONS
c
      FUNCTION EREPUL(XYZ,X,Y,Z,AREF)
      INTEGER XYZ(150,150,150),X,Y,Z
      DATA L0 /-1/
      I=0
      IX=X-1
      JX=X+1
      IY=Y-1
      JY=Y+1
      IZ=Z-1
      JZ=Z+1
c                                    fcc lattice
      IF(XYZ(IX,IY,Z).LT.L0) I=I+1
      IF(XYZ(IX,JY,Z).LT.L0) I=I+1
      IF(XYZ(JX,IY,Z).LT.L0) I=I+1
      IF(XYZ(JX,JY,Z).LT.L0) I=I+1
            IF(XYZ(X,IY,IZ).LT.L0) I=I+1
            IF(XYZ(X,IY,JZ).LT.L0) I=I+1
            IF(XYZ(X,JY,IZ).LT.L0) I=I+1
            IF(XYZ(X,JY,JZ).LT.L0) I=I+1
      IF(XYZ(IX,Y,IZ).LT.L0) I=I+1
      IF(XYZ(IX,Y,JZ).LT.L0) I=I+1
      IF(XYZ(JX,Y,IZ).LT.L0) I=I+1
      IF(XYZ(JX,Y,JZ).LT.L0) I=I+1
      EREPUL=I*AREP
      RETURN
      END
```

```
C
C       HYDROGEN BONDING AND "COOPERATIVITY" (BETA AND ALPHA MOTIFFS)
        FUNCTION EHB(XYZ,ICA,PRODV,IX,IY,IZ,ID,AHB)
        INTEGER XYZ(150,150,150),ICA(0:150),PRODV(24,24)
        DATA L0 /-1/
        I=0
        IXL=IX-3
        IXP=IX+3
        IYL=IY-3
        IYP=IY+3
        IZL=IZ-3
        IZP=IZ+3
        IC1=ICA(ID-1)
        IC2=ICA(ID)
        IF(XYZ(IXL,IY,IZ).LT.L0) THEN
                IDD=-XYZ(IXL,IY,IZ)
                IN1=ICA(IDD-1)
                IN2=ICA(IDD)
        I=I+PRODV(IC1,IN1)+PRODV(IC1,IN2)+PRODV(IC2,IN1)+PRODV(IC2,IN2)
                ENDIF
C
        IF(XYZ(IXP,IY,IZ).LT.L0) THEN
                IDD=-XYZ(IXP,IY,IZ)
                IN1=ICA(IDD-1)
                IN2=ICA(IDD)
        I=I+PRODV(IC1,IN1)+PRODV(IC1,IN2)+PRODV(IC2,IN1)+PRODV(IC2,IN2)
                ENDIF
C
        IF(XYZ(IX,IYL,IZ).LT.L0) THEN
                IDD=-XYZ(IX,IYL,IZ)
                IN1=ICA(IDD-1)
                IN2=ICA(IDD)
        I=I+PRODV(IC1,IN1)+PRODV(IC1,IN2)+PRODV(IC2,IN1)+PRODV(IC2,IN2)
                ENDIF
C
        IF(XYZ(IX,IYP,IZ).LT.L0) THEN
                IDD=-XYZ(IX,IYP,IZ)
                IN1=ICA(IDD-1)
                IN2=ICA(IDD)
        I=I+PRODV(IC1,IN1)+PRODV(IC1,IN2)+PRODV(IC2,IN1)+PRODV(IC2,IN2)
                ENDIF
C
        IF(XYZ(IX,IY,IZL).LT.L0) THEN
                IDD=-XYZ(IX,IY,IZL)
                IN1=ICA(IDD-1)
                IN2=ICA(IDD)
        I=I+PRODV(IC1,IN1)+PRODV(IC1,IN2)+PRODV(IC2,IN1)+PRODV(IC2,IN2)
                ENDIF
C
        IF(XYZ(IX,IY,IZP).LT.L0) THEN
                IDD=-XYZ(IX,IY,IZP)
                IN1=ICA(IDD-1)
                IN2=ICA(IDD)
        I=I+PRODV(IC1,IN1)+PRODV(IC1,IN2)+PRODV(IC2,IN1)+PRODV(IC2,IN2)
                ENDIF
```

APPENDIX E

SAMPLE INPUT

```
.25  0.25  0.25  0.34  0.25  0.34  0.25    ← Weights for states
                                              6,8,10,12,14,16,18
1.   0.25  0.75  6.0  -0.15  -0.6          ← Repulsive potential
                                              weight.
                                            ← Dihedral (tortional/
                                              rotational) angle
                                              weight.
                                            ← Hydrogen bond (bond
                                              angle) parameter.

0.35   4    Size of kink jump
```

States

| Residue | 6 | 8 | 10 | 12 | 14 | 16 | 18 | Hydrophobicity | |
|---------|---|---|----|----|----|----|----|----------------|---|
| 2       | 1 | 1 | 1  | 0  | 1  | 1  | 1  | -1             | ⎫ Bond angle |
| 3       | 1 | 1 | 1  | 0  | 1  | 1  | 1  | -1             | ⎬ preferences for |
| 4       | 1 | 1 | 1  | 0  | 1  | 1  | 1  | -1             | ⎭ various states. |
| ⋮       |   |   |    |    |    |    |    |                |   |
| 10      | 1 | 1 | 0  | 1  | 1  | 1  | -1 |                |   |
| 11      | 1 | 1 | 1  | 1  | 0  | 1  | 1  |                |   |
| ⋮       |   |   |    |    |    |    |    |                |   |
| 31      | 1 | 1 | 1  | 1  | 0  | 1  | 1  | 0              | ← Glycine |
| ⋮       |   |   |    |    |    |    |    |                |   |
| 43      | 1 | 1 | 1  | 1  | 0  | 1  | 1  | 1              |   |
| ⋮       |   |   |    |    |    |    |    |                |   |
| n       |   |   |    |    |    |    |    |                |   |

| | | | | | |
|----|----|----|-----|----|---|
| 2  | 16 | 37 | 1   | 1  | ⎫ Dihedral |
| 3  | 16 | 37 | 1   | 1  | ⎬ (tortional/ rotational) angles for sequence. |
| ⋮  |    |    |     |    |   |
| 10 | 10 | 21 | 1.5 | 1  | |
| ⋮  |    |    |     |    | |
| 31 | 14 | 11 | 1.5 | -1 | |
| ⋮  |    |    |     |    | |
| 43 | 14 | 29 | 1.5 | -1 | |
| ⋮  |    |    |     |    | |
| n  |    |    |     |    | |

```
PHIL-PHOB, PHIL-PHIL, PHOB-PHOB          1.000    0.250   -0.750
REPULSIVE INT. AND COOPER. +H-BOND       6.000   -0.150
SCALING FACTOR FOR DIHEDRAL ANGLE POTENTIAL     -0.600
```

APPENDIX E

SAMPLE TERTIARY INTERACTION TABLE

| | | | |
|---|---|---|---|
| 1 = cys | 6 = val | 11 = thr | 16 = asp |
| 2 = met | 7 = tryp | 12 = ser | 17 = his |
| 3 = phe | 8 = tyr | 13 = gln (glutamine) | 18 = arg |
| 4 = ile | 9 = ala | 14 = asn | 19 = lys |
| 5 = leu | 10 = gly | 15 = glu (glutonic acid) | 20 = pro | cys interactions ahyd(1,1)=-5.44
ahyd(1,2)=-5.05
ahyd(1,3)=-5.63
ahyd(1,4)=-5.03
ahyd(1,5)=-5.03
ahyd(1,6)=-4.46
ahyd(1,7)=-4.76
ahyd(1,8)=-3.89
ahyd(1,9)=-3.38
ahyd(1,10)=-3.16
ahyd(1,11)=-2.88
ahyd(1,12)=-2.86
ahyd(1,13)=-2.73
ahyd(1,14)=-2.59
ahyd(1,15)=-2.08
ahyd(1,16)=-2.66
ahyd(1,17)=-3.63
ahyd(1,18)=-2.70
ahyd(1,19)=-1.54
ahyd(1,20)=-2.92 phe interactions
ahyd(3,3)=-6.85
ahyd(3,4)=-6.39
ahyd(3,5)=-6.26
ahyd(3,6)=-5.75
ahyd(3,7)=-6.02
ahyd(3,8)=-4.95
ahyd(3,9)=-4.36
ahyd(3,10)=-3.72
ahyd(3,11)=-3.76
ahyd(3,12)=-3.56
ahyd(3,13)=-3.30
ahyd(3,14)=-3.55
ahyd(3,15)=-3.51
ahyd(3,16)=-3.31
ahyd(3,17)=-4.61
ahyd(3,18)=-3.54
ahyd(3,19)=-2.83
ahyd(3,20)=-3.73 leu
ahyd(5,5)=-5.79
ahyd(5,6)=-5.38
ahyd(5,7)=-5.50
ahyd(5,8)=-4.26
ahyd(5,9)=-3.96
ahyd(5,10)=-3.43
ahyd(5,11)=-3.43
ahyd(5,12)=-3.16
ahyd(5,13)=-3.09
ahyd(5,14)=-2.99
ahyd(5,15)=-2.91
ahyd(5,16)=-2.59
ahyd(5,17)=-3.84
ahyd(5,18)=-3.15
ahyd(5,19)=-2.63
ahyd(5,20)=-3.06 valine
ahyd(6,6)=-4.94
ahyd(6,7)=-5.05
ahyd(6,8)=-4.05
ahyd(6,9)=-3.62
ahyd(6,10)=-3.06
ahyd(6,11)=-2.95
ahyd(6,12)=-2.79
ahyd(6,13)=-2.67
ahyd(6,14)=-2.36
ahyd(6,15)=-2.56
ahyd(6,16)=-2.25
ahyd(6,17)=-3.38
ahyd(6,18)=-2.78
ahyd(6,19)=-1.95
ahyd(6,20)=-2.96 met interactions
ahyd(2,2)=-6.06
ahyd(2,3)=-6.68
ahyd(2,4)=-6.33
ahyd(2,5)=-6.01
ahyd(2,6)=-5.52
ahyd(2,7)=-6.37
ahyd(2,8)=-4.92
ahyd(2,9)=-3.99
ahyd(2,10)=-3.75
ahyd(2,11)=-3.73
ahyd(2,12)=-3.55
ahyd(2,13)=-3.17
ahyd(2,14)=-3.50
ahyd(2,15)=-3.19
ahyd(2,16)=-2.90
ahyd(2,17)=-3.31
ahyd(2,18)=-3.49
ahyd(2,19)=-3.11
ahyd(2,20)=-4.11 ile interactions
ahyd(4,4)=-6.22
ahyd(4,5)=-6.17
ahyd(4,6)=-5.58
ahyd(4,7)=-5.64
ahyd(4,8)=-4.63
ahyd(4,9)=-4.41
ahyd(4,10)=-3.65
ahyd(4,11)=-3.74
ahyd(4,12)=-3.43
ahyd(4,13)=-3.22
ahyd(4,14)=-2.99
ahyd(4,15)=-3.23
ahyd(4,16)=-2.91
ahyd(4,17)=-3.76
ahyd(4,18)=-3.33
ahyd(4,19)=-2.70
ahyd(4,20)=-3.47 tryp
ahyd(7,7)=-5.42
ahyd(7,8)=-4.44
ahyd(7,9)=-3.93
ahyd(7,10)=-3.37
ahyd(7,11)=-3.31
ahyd(7,12)=-2.95
ahyd(7,13)=-3.16
ahyd(7,14)=-3.11
ahyd(7,15)=-2.94
ahyd(7,16)=-2.91
ahyd(7,17)=-4.02
ahyd(7,18)=-3.56
ahyd(7,19)=-2.49
ahyd(7,20)=-3.66 tyr
ahyd(8,8)=-3.55
ahyd(8,9)=-2.85
ahyd(8,10)=-2.50
ahyd(8,11)=-2.48
ahyd(8,12)=-2.30
ahyd(8,13)=-2.53
ahyd(8,14)=-2.47
ahyd(8,15)=-2.42
ahyd(8,16)=-2.25
ahyd(8,17)=-3.33
ahyd(8,18)=-2.75
ahyd(8,19)=-2.01
ahyd(8,20)=-2.80 ala
ahyd(9,9)=-2.51 thr
ahyd(11,11)=-1.72
ahyd(11,12)=-1.59
ahyd(11,13)=-1.59
ahyd(11,14)=-1.51
ahyd(11,15)=-1.45
ahyd(11,16)=-1.66
ahyd(11,17)=-2.31
ahyd(11,18)=-1.97
ahyd(11,19)=-1.02
ahyd(11,20)=-1.66 serine
ahyd(12,12)=-1.48
ahyd(12,13)=-1.37
ahyd(12,14)=-1.31
ahyd(12,15)=-1.48 glu
ahyd(15,15)=-1.18
ahyd(15,16)=-1.23
ahyd(15,17)=-2.27
ahyd(15,18)=-2.07
ahyd(15,19)=-1.60
ahyd(15,20)=-1.40 asp
ahyd(16,16)=-0.96
ahyd(16,17)=-2.14
ahyd(16,18)=-1.98
ahyd(16,19)=-1.32
ahyd(16,20)=-1.19 his
ahyd(17,17)=-2.78

```
ahyd(9,10)=-2.15    ahyd(12,16)=-1.46    ahyd(17,18)=-2.12
ahyd(9,11)=-2.15    ahyd(12,17)=-1.94    ahyd(17,19)=-1.09
ahyd(9,12)=-1.89    ahyd(12,18)=-1.22    ahyd(17,20)=-2.17
ahyd(9,13)=-1.70    ahyd(12,19)=-0.83    +++++++++++++++++
ahyd(9,14)=-1.44    ahyd(12,20)=-1.35    arg
                    +++++++++++++++++    ahyd(18,18)=-1.39
                    glutamine            ahyd(18,19)=-0.06
                    ahyd(13,13)=-0.89    ahyd(18,20)=-1.85
ahyd(9,15)=-1.51    ahyd(13,14)=-1.36    +++++++++++++++++
ahyd(9,16)=-1.57    ahyd(13,15)=-1.33    lys
ahyd(9,17)=-2.09    ahyd(13,16)=-1.26    ahyd(19,19)=-0.13
ahyd(9,18)=-1.50    ahyd(13,17)=-1.85    ahyd(19,20)=-0.67
ahyd(9,19)=-1.10    ahyd(13,18)=-1.85    +++++++++++++++++
ahyd(9,20)=-1.81    ahyd(13,19)=-1.02    pro
+++++++++++++++++   ahyd(13,20)=-1.73    ahyd(20,20)=-1.18
ahyd(10,10)=-2.17   +++++++++++++++++
ahyd(10,11)=-2.03   asn
ahyd(10,12)=-1.70   ahyd(14,14)=-1.59
ahyd(10,13)=-1.54   ahyd(14,15)=-1.43
ahyd(10,14)=-1.56   ahyd(14,16)=-1.33
ahyd(10,15)=-1.22
ahyd(10,16)=-1.62
ahyd(10,17)=-1.94   ahyd(14,17)=-2.01
ahyd(10,18)=-1.68   ahyd(14,18)=-1.41
ahyd(10,19)=-0.84   ahyd(14,19)=-0.91
ahyd(10,20)=-1.72   ahyd(14,20)=-1.43
+++++++++++++++++   +++++++++++++++++
```

SAMPLE OUTPUT

The native contact pairs are:

```
    2     18
   25     53
   57    163
```

Snapshot (interim report) every 5000 Monte Carlo timesteps.

TEMPERATURE OF THE SYSTEM = 0.340

- Square of distance between adjacent α-carbons. → R2
- Radius of gyration squared. → AS2
- Number of contacts between sidechains. → any contacts

```
iterm=  R2=   AS2=   ENERGY=    native  any contacts
   1    225   50.23  -302.2651    0      30
   2    203   48.55  -294.1492    0      30
   3    257   49.63  -298.5013    0      30
   4    227   49.07  -301.3834    0      30
   5    275   50.14  -306.7366    0      30
   6    299   50.46  -304.1194    0      30
   7    221   49.85  -303.1781    0      30
   8    331   48.67  -294.3552    0      28
   9    329   47.93  -294.4433    0      28
  10    257   49.45  -291.8564    0      27
  11    297   49.12  -299.2383    0      29
  12    299   49.15  -299.5342    0      29
  13    297   48.81  -298.7695    0      29
```

```
 14  261   48.46  -294.4760    0   29
 15  297   50.30  -300.5060    0   30
 16  201   48.37  -292.5648    0   28
 17  269   48.30  -293.5644    0   28
 18  269   49.49  -298.5347    0   29
 19  275   50.13  -305.4173    0   30
 20  237   50.13  -285.0356    0   27
 21  237   46.07  -288.0940    0   27
 22  363   49.26  -298.0356    0   30
 23  227   49.21  -293.2128    0   29
 24  241   50.60  -297.5958    0   30
```

FINAL CONFORMATION

```
        VECTOR1      VECTOR2        SIDE 1/2/3         HANDENES 2   0  2  1     1  0  2    -1-1 1 -1-1 0 -1 0 1    -1   14  21
 3   1  0  2    -2  0  1     1 1 1  1 1 0  1 0 1    -1   10  25
 4  -2  0  1     1  0  2    -1-1-1 -1-1 0 -1 0-1    -1   10  11

5   1  0  2     2 -1  0    -1-1 1 -1-1 0 -1 0 1    -1   14  27
 6   2 -1  0     2  0 -1    -1-1-1 -1-1 0 -1 0-1    -1   18  37
 7   2  0 -1     2  0  1    -1 1-1 -1 1 0 -1 0-1    -1   16  37
 8   2  0  1     2  1  0     1-1-1  1-1 0  1 0-1    -1   18  25
 9   2  1  0     0 -1  2    -1 1-1 -1 1 0 -1 0-1    -1    8   9
10   0 -1  2    -2  0  1     1 1 1  1 1 0  1 0 1    -1   14  17
11  -2  0  1     0 -2 -1     0 0 0  0 0 0  0 0 0     1    8  17

12   0 -2 -1    -2  1  0     1-1 1  1-1 0  1 0 1    -1    6  21
13  -2  1  0    -2  1  0     1 1-1  1 1 0  1 0-1    -1   16  37
14  -2 -1  0    -2  0 -1    -1 1 1 -1 1 0 -1 0 1    -1   18  35
15  -2  0 -1    -1  0 -2    -1 1 1 -1 1 0 -1 0 1    -1   18  29
16  -1  0 -2    -2  0  1     1-1-1  1-1 0  1 0-1    -1   10  21
17  -2  0  1    -1  2  0     1 1 1  1 1 0  1 0 1    -1   14  21
18  -1  2  0     1  2  0    -1-1 1 -1-1 0 -1 0 1    -1   16  21
19   1  2  0    -1  0 -2     1-1 1  1-1 0  1 0 1    -1    8  17
20  -1  0 -2     0  2  1    -1-1-1 -1-1 0 -1 0-1    -1    6   9
21   0  2  1    -1  0  2    -1-1-1 -1-1 0 -1 0-1    -1   14  27
22  -1  0  2     0 -1  2    -1-1-1 -1-1 0 -1 0-1    -1   18  27
23   0 -1  2     2  0  1    -1-1 1 -1-1 0  1 0-1    -1   14  17
24   2  0  1     0 -2 -1    -1 1 1 -1 1 0 -1 0 1    -1    8  17
25   0 -2 -1     1  0  2     1-1 1  1-1 0  1 0-1    -1    6  11
26   1  0  2     0  1  2     1 1-1  1 1 0  1 0-1    -1   18  21
27   0  1  2     1 -2  0    -1-1 1 -1-1 0 -1 0 1    -1    6  13
28   1 -2  0    -1 -2  0     1 1 1  1 1 0  1 0 1    -1   16  21
29  -1 -2  0     1  0 -2    -1-1-1 -1-1 0 -1 0 1    -1    8   9
30   1  0 -2     2  1  0    -1-1-1 -1-1 0 -1 0-1    -1   14  17
31   2  1  0     1  0  2    -1 1 1 -1 1 0 -1 0 1    -1   14   9
32   1  0  2    -1 -2  0     1 1 1  1 1 0 -1 0 1    -1    8  25
33  -1 -2  0     0 -1  2     1-1-1  1-1 0  1 0-1    -1   14  25
34   0 -1  2     1  0  2     1-1-1  1-1 0  1 0-1    -1   18  17
35   1  0  2    -1  2  0     1-1-1  1-1 0  1 0-1    -1    8  25
36  -1  2  0     0  2  1     0 0 0  0 0 0  0 0 0     1   18  27
37   0  2  1     0  1 -2     1 1 1  1 1 0  1 0 1    -1   10  29
38   0  1 -2     0  2 -1    -1-1-1 -1-1 0 -1 0-1    -1   18  17
39   0  2 -1     2 -1  0    -1 1 1 -1 1 0 -1 0 1    -1    6  19
40   2 -1  0     1  0 -2    -1-1-1 -1-1 0 -1 0-1    -1   14  25
```

•
  •
  •

```
       375  249   46.81  -292.8082    0   28
       376  269   45.55  -287.4545    0   30
       377  205   45.26  -290.7192    0   28
       378  299   49.93  -295.7486    0   27
       379  251   48.87  -292.7481    0   28
       380  285   48.30  -295.7492    0   29
       381  305   49.53  -295.7792    0   27
       382  275   47.54  -297.3956    0   27
```

```
383  305   47.66 -296.4246   0  30
384  285   48.34 -296.7784   0  26
385  275   49.99 -305.2485   0  30
386  117   48.92 -297.6013   0  30
387  241   49.43 -299.3969   0  30
388  299   49.99 -303.4559   0  30
389  257   49.15 -298.2790   0  30
390  275   49.46 -303.6329   0  30
391  145   48.75 -300.4864   0  30
392  373   48.91 -287.5453   0  29
393  275   50.86 -301.0170   0  28
394  275   50.16 -304.6649   0  30
395  275   50.25 -302.6943   0  30
396  293   50.86 -296.6948   0  28
397  297   49.58 -298.8719   0  29
398  299   49.58 -300.4898   0  28
399  341   50.76 -296.8724   0  31
400  269   49.22 -295.0204   0  28
```

<E>= -295.6850    <E2>= 8.74568216D+04    CV= 2.71777422D+01
mean-square-end to end vector= 2.56595001D+02
<S2>= 4.85322037D+01
native contacts= 0.00000000D+00
number of contacts= 2.84550000D+01

```
    fkink=      fend =      fwave=      frot=

0.029328   0.133321    0.000000    0.001293
```

---

```
 6   10797  140136   11818   10619   10528
 8   27659  102491   31519  101909   31348
10   42315   42630   42626   42620   42721
12   19949   45247   38505   40334   47439
14  344543  344363  343647  345273  344759
16  407038   70689   64827   63643   70601
18  211817  211240  211463  211478  211935
``` lenf  7*lenf  lenf-2  -nbgl  ngbl   .78   546   70   6

L-GLY, occupancy and side groups    72   546   70

********** contact map **********

```
      2and  4are inert       0.0000
 **   3 and  7 are attractive   -12.5588
 **   3 and 69 are attractive    -3.8824
 **   5 and 15 are attractive   -11.2059
 **   5 and 17 are attractive   -11.0588
 **   5 and 19 are attractive    -9.3235
 **   5 and 25 are attractive   -11.2059
 **   7 and 69 are attractive    -8.7353
 **   9 and 73 are attractive    -3.0000
 ** 10 and 72 are attractive    -9.9412
     11and 13are inert       0.0000
 ** 11 and 71 are attractive    -3.0000
     15and 17are inert       0.0000
 ** 17 and 25 are attractive    -3.0000
 ** 19 and 25 are attractive    -9.3235
 ** 28 and 32 are attractive    -9.3235
 ** 28 and 38 are attractive    -9.3235
 ** 32 and 38 are attractive   -11.2059
 ** 32 and 40 are attractive    -3.1176
 ** 45 and 53 are attractive    -9.9412

** 46 and 58 are attractive   -11.0588
 ** 47 and 61 are attractive    -7.4706
 ** 47 and 63 are attractive   -11.7059
 ** 52 and 70 are attractive    -9.9412
 ** 52 and 74 are attractive    -9.9412
 ** 55 and 75 are attractive    -3.0000
     61and 63are inert       0.0000
     70 and 74 residues are repulsive    0.8529
```

What is claimed is:

1. Method of determining a three-dimensional conformation of a globular protein utilizing Monte Carlo dynamics technique with asymmetric Metropolis sampling criterion, the method comprising the steps of:

specifying a sequence of amino acid residues of the protein;

creating a 210 lattice structure for each amino acid of said globular protein;

spatially representing an unfolded conformation of said globular protein consisting of an $\alpha$-carbon backbone and sidechains corresponding to the specified sequence;

selecting from the unfolded conformation, using said technique, successive likely tertiary conformations at a predetermined temperature, each said conformation having a different total-free-energy;

selecting from the successive likely conformations, each said conformation represented by spacial coordinates, the lowest total-free-energy tertiary conformation which satisfies said criterion; and creating a coordinate set of the selected tertiary conformation for display.

2. The method of claim 1 wherein the step of selecting includes the step of determining local conformational energetic preferences of the $\alpha$-carbons comprising said $\alpha$-carbon backbone.

3. The method of claim 2 wherein the step of determining the local conformation energetic preferences includes the step of identifying spatially close pairs of sidechains in each local conformation.

4. The method of claim 3 wherein the step of identifying spatially close pairs of sidechains includes the step of simulating tertiary interactions between said spatially close pairs.

5. The method of claim 4 wherein the step of simulating tertiary interactions includes the step of determining the sum of the effective interaction contact energy between respective close pairs based on a predetermined frequency of contact between said pairs.

6. The method according to claim 5 wherein the step of determining the effective interaction contact energy includes the step of scaling said contact energy to a selected lowest level by referencing average interaction contact energies of non-polar residues to a hydrophobicity scale.

7. A computer-based system for determining a three-dimensional structure of a protein including sidechains or portion thereof including sidechains, the system comprising:

input means for specifying a sequence of amino acid residues whose native tertiary structure is to be determined, and for specifying a temperature and local conformation preferences for respective residues of the sequence;

a first memory for storing the specified sequence, temperature, and conformation preferences;

a second memory having a stored program with routines for creating a 210 lattice structure for each amino acid of said sequence and spatially representing the tertiary interactions between all pairs of the sidechains;

a processor coupled to the input means, and first and second memories, and utilizing the specified sequence, temperature, and conformation preferences for spatially representing a conformation of an unfolded chain of the residues in three dimensions, selecting from the unfolded conformation, successive likely tertiary conformations at a predetermined temperature, each conformation having a different total free energy, and selecting the lowest free energy tertiary conformation in agreement with said conformation preferences and total interaction energy, and creating a second set of coordinates representing a native tertiary structure; and display means coupled to the processing means for displaying the second set of coordinates representing the native tertiary structure in three dimensions.

8. An apparatus for determining a three-dimensional structure of a selected protein, said protein including a plurality of $\alpha$-carbons comprising:

a memory for storing a representation of a selected sequence of amino acid residues of the protein and an initial starting temperature value;

a processor for generating a representation of a 210 lattice, for positioning adjacent sites a unit distance from one another and for positioning a plurality of $\alpha$-carbons on selected lattice sites, each $\alpha$-carbon located a distance on the order of $\sqrt{5}$ from an adjacent $\alpha$-carbon;

instructions memory for combining said generated representation of said cubic arrangement with said representation of said selected stored sequence and for producing, in response to said temperature and in agreement with said cubic arrangement, a representation of one or more folded, three-dimensional protein structures; and means for comparing said produced representation of three-dimensional protein structure to a predetermined criterion and for selecting one of said produced representation for display only in response to a predetermined comparison result.

9. An apparatus as in claim 8 including an interrupt controller for interrupting said instructions, storing a new temperature value and re-initiating said instructions.

10. The apparatus of claim 8 wherein said protein comprises a portion of a protein.

11. A computer apparatus for determining the three-dimensional structure of a protein including sidechains or portion thereof, comprising:

a processor means comprising:

a computer memory for storing a specific sequence of amino acid residues, a temperature, and local conformational preferences;

first computer software stored in said computer memory for creating a 210 lattice structure for each amino acid in said sequence, and representing tertiary interactions between all pairs of said sidechains;

second computer software stored in said computer memory for utilizing the specified sequence, temperature, processor, and conformation preferences to generate a first set of coordinates representing a conformation of an unfolded chain of the residues in three dimensions, determining a total free interaction energy from tertiary interactions between all pairs of the sidechains, simulating folding of the chain at the specified temperature utilizing said conformation preferences and total interaction energy;

means responsive to said instructions for producing a second set of coordinates representing a native tertiary structure of said protein; and display means, connected to said processor for visually displaying to a user on command, a second set of coordinates representing the native tertiary structure of said sequence in three dimensions.

12. A computer-assisted method for determining the three dimensional structure of a protein comprising the steps of:
   inputting a sequence of amino acids whose three dimensional conformation is to be determined;
   creating a 210 lattice structure for each amino acid of said protein;
   spatially representing the centers of said amino acids in a linear order;
   specifying a temperature;
   selecting, through trial and error, the lowest free energy state of said polypeptide chain in its native conformation; and
   visually displaying, using computer graphics, computer designed protein molecules representing said sequence of amino acids in its lowest free energy state.

13. The method of claim 12 wherein said selecting step utilizes Monte Carlo dynamics with as asymmetric Metropolis sampling criterion.

14. The method of claim 12 wherein the selecting step includes the option of stopping the selection at an intermediate stage, specifying another temperature, and resuming the selection.

15. The method of claim 12 wherein said selecting step includes the step of determining the effective tertiary local free energies between respective close amino acid pairs based on a predetermined frequency.

16. The method of claim 12 wherein prior to the step of selecting the lowest free energy state, the method further comprises the step of specifying any known local conformation preferences of said polypeptide chain.

17. The method of claim 12 wherein said lattice is a 24-nearest neighbor lattice.

18. The method of claim 12 wherein said selecting step further includes the step of determining the sum of the effective tertiary local free energy between respective close pairs based on a predetermined frequency of contact between said pairs.

19. The method according to claim 18 wherein said selecting step includes, prior to said summation step, the step of scaling said tertiary local free energy to a selected lowest level by comparing average interaction contact energies of non-polar residues to a hydrophobicity scale.

20. The method of claim 12 wherein said lattice structure comprises a cubic arrangement represented by unit vectors $(\pm 1,0,0)$, $(0,\pm 1,0)$, $(0,0\pm 1)$, and where the distance between adjacent lattice sites on the polypeptide chain is unity.

21. The method of claim 20 wherein the $\alpha$-carbon of each amino acid on said lattice site occupies a position located at a distance of $\sqrt{5}$ units from its adjacent $\alpha$-carbon along a $(\pm 2,\pm 1,0)$ vector or cyclic permutation thereof.

22. The method of claim 12 wherein said mapping step further comprises representing each $\alpha$-carbon of said amino acids as a central cubic lattice site plus six adjacent cubic lattice sites defining a surface interaction of finite size.

23. The method of claim 22 further comprising the step of representing each sidechain of said amino acids as being embedded in the said lattice and occupying a selected number of lattice sites located relative to said central cubic lattice site, the number of sites occupied by the sidechain being proportional to the number of sites defining said surface of interaction.

24. A computer-assisted method for making a synthetic protein comprising the steps of:
   inputting a sequence of amino acids whose three dimensional conformation is to be determined;
   creating a 210 lattice structure for each amino acid of said protein;
   spatially representing the centers of said amino acids in a linear order;
   specifying a temperature;
   selecting, through trial and error, the lowest free energy state of said sequence of amino acids in its native conformation;
   visually displaying, using computer graphics, computer designed protein molecules representing said polypeptide chain in its lowest free energy state; and
   making a synthetic protein corresponding to said amino acid sequence.

* * * * *